United States Patent [19]

Henzi

[11] 4,048,151

[45] Sept. 13, 1977

[54] CATIONIC DYES CONTAINING AN OPTIONALLY SUBSTITUTED BICYCLIC OR POLYCYCLIC ARYLOXYALKYL GROUP

[75] Inventor: Beat Henzi, Neuallschwil, Switzerland

[73] Assignee: Sandoz Ltd., Basel, Switzerland

[21] Appl. No.: 383,781

[22] Filed: July 30, 1973

[30] Foreign Application Priority Data

July 31, 1972 Switzerland .................. 11354/72
Feb. 21, 1973 Switzerland .................. 2523/73

[51] Int. Cl.² .............. C09B 1/32; C09B 23/10; C09B 23/12; C09B 29/08
[52] U.S. Cl. .............. 260/156; 260/155; 260/157; 260/158; 260/165; 260/314; 260/315; 260/329.3; 260/332.1; 260/379; 260/380; 260/571; 260/346.71; 260/330.5; 542/400
[58] Field of Search .............. 260/156, 157, 158, 196, 260/199, 240 R, 240 D, 240 E, 240 G, 165

[56] References Cited

U.S. PATENT DOCUMENTS

| 2,175,803 | 10/1939 | Honold et al. ............ 260/157 |
| 2,392,181 | 1/1946 | Parker et al. ............ 260/152 |
| 2,399,026 | 4/1946 | Henzi ............ 260/158 X |
| 2,967,887 | 1/1961 | Hanford et al. ............ 260/196 X |
| 3,078,137 | 2/1963 | Baumann et al. ............ 260/157 X |
| 3,102,878 | 9/1963 | Baumann et al. ............ 260/157 X |
| 3,133,052 | 5/1964 | Merian et al. ............ 260/158 |
| 3,177,198 | 4/1965 | Weis et al. ............ 260/152 |
| 3,271,383 | 9/1966 | Yamaya et al. ............ 260/158 |
| 3,513,153 | 5/1970 | Horstmann et al. ............ 260/152 |
| 3,542,758 | 11/1970 | Hegar ............ 260/156 |
| 3,709,871 | 1/1973 | Ditzer et al. ............ 260/199 |
| 3,770,716 | 11/1973 | Ozutsumi et al. ............ 260/146 R |
| 3,847,983 | 11/1974 | Kobayashi et al. ............ 260/152 X |

FOREIGN PATENT DOCUMENTS

| 2,059,096 | 1/1972 | Germany |
| 1,943,800 | 4/1970 | Germany ............ 260/157 |
| 2,044,823 | 3/1972 | Germany ............ 260/162 |
| 71-08029 | 12/1971 | Netherlands ............ 260/158 |
| 1,276,686 | 6/1972 | United Kingdom ............ 260/158 |
| 1,288,718 | 9/1972 | United Kingdom ............ 260/158 |
| 1,094,309 | 12/1967 | United Kingdom ............ 260/155 |
| 1,117,734 | 6/1968 | United Kingdom ............ 260/157 |
| 1,220,852 | 1/1971 | United Kingdom ............ 260/158 |
| 1,117,734 | 6/1968 | United Kingdom ............ 260/157 |

*Primary Examiner*—Floyd D. Higel
*Attorney, Agent, or Firm*—Gerald D. Sharkin; Richard E. Vila; Melvyn M. Kassenoff

[57] ABSTRACT

Disclosed are basic dyes free from sulphonic acid groups of the formula

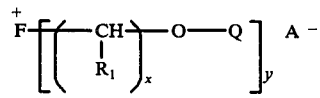

in which
F+ signifies a cationic group-containing residue of a dye such as an azo, styryl, azomethine, methine, anthraquinone, nitro or triphenylmethyl dye,
x signifies 1, 2 or 3,
y signifies 1, 2, 3 or 4,
A+ signifies an anion, and
Q signifies an optionally substituted biphenylyl, dibenzofuranyl, carbazolyl, dibenzothiophenyl, dibenzothiophendioxydyl, dibenzothiophenmonoxydyl, fluorenyl or fluorenonyl radical, and
$R_1$ signifies hydrogen, phenyl, cycloalkyl, unsubstituted $C_{1-4}$ alkyl or $C_{1-4}$ alkyl substituted by halogen, $C_{1-4}$ alkoxy or phenoxy.

These dyes are useful for dyeing and printing polyacrylonitrile and poly-asymmetrical dicyanoethylene and copolymers thereof as well as modified polyesters and polyamides containing acid groups. The dyes build-up well and exhibit good pH stability and stability to boiling. The obtained dyeings are level and possess good fastness to light, wet treatments, solvents, heat treatments and cross-dyeing.

23 Claims, No Drawings

CATIONIC DYES CONTAINING AN OPTIONALLY SUBSTITUTED BICYCLIC OR POLYCYCLIC ARYLOXYALKYL GROUP

The invention relates to basic dyes free from sulphonic acid groups.

The invention provides compounds of formula I,

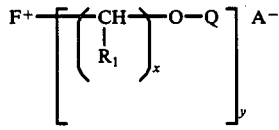

in which
F+ signifies a dye residue containing a cationic group,
x signifies 1, 2 or 3,
y signifies 1, 2, 3 or 4
A⁻ signifies an anion, and
Q signifies an optionally substituted biphenylyl, dibenzofuranyl, carbazolyl, dibenzothiophenyl, dibenzothiophendioxydyl, dibenzothiophenmonoxydyl, fluorenyl or fluorenonyl radical, and
R₁ signifies hydrogen, phenyl, $C_{5-6}$ cycloalkyl, unsubstituted $C_{1-4}$ alkyl or $C_{1-4}$ alkyl substituted by halogen, $C_{1-4}$ alkoxy or phenoxy.

In the compounds of formula I, x preferably signifies 1 or 2, and y preferably signifies 1 or 2, more preferably 1.

As examples of A⁻ may be given the halides, such as chloride, bromide or iodide, sulphate, disulphate, methylsulphate, aminosulphate perchlorate, carbonate, bicarbonate, phosphate, phosphormolybdate, phosphortungstenate, phosphortungstenmolybdate, formate, benzenesulphonate, naphthalenesulphonate, 4-chlorobenzenesulphonate, oxalate, maleinate, acetate, propionate, lactate, succinate, chloroacetate, tartrate, malate, methanesulphonate or benzoate ions, or complex anions such as zinc chloride double salts, e.g. $ZnCl_3^-$. The preferred anions are chloride, methylsulphate, $ZnCl_3^-$ and acetate.

The significance given above for Q may, for example, be substituted, preferably by 1 or 2 substituents, more preferably by 1 substituent, selected from hydroxy; halogen; alkyl or alkoxy of 1 to 4 carbon atoms, unsubstituted or substituted by halogen, hydroxy, cyano, phenyl or phenoxy; cycloalkyl of 5 or 6 carbon atoms, unsubstituted or substituted by alkyl of 1 to 4 carbon atoms; cyano; nitro; benzoyl trifluoromethyl; phenoxy; phenylazo; or a radical of the formula —CORo,

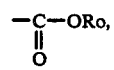

—SO₂—Ro, —SO₂—NH—Ro,

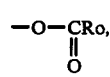

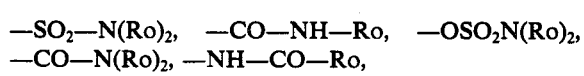

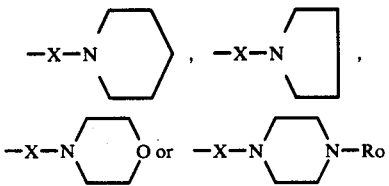

in which the Ro's, independently, signify $C_{1-4}$ alkyl or phenyl, and X signifies —CO— or —SO₂—.

The significances given above for Q are preferably unsubstituted. Q more preferably signifies a biphenylyl, e.g. o-or p-biphenylyl, radical or a dibenzofuranyl radical, e.g. 1-, 2- or 3-dibenzofuranyl, preferably 3-dibenzofuranyl, most preferably an unsubstituted such radical.

R₁ preferably signifies hydrogen, $C_{1-4}$ alkyl or phenyl, more preferably hydrogen or methyl.

The cationic group contained in F⁺ is preferably a quaternary ammonium radical, a protonated amine radical, a

radical, a hydrazinium, cycloimmonium or an etherified hydroxylammonium ion, most preferably a quaternary ammonium radical. As examples of dye residues F⁺ may be given azo, styryl, hydrazone (azomethine), methine, anthraquinone, nitro and triphenylmethane dye residues.

The azo dyes provided by the invention may be represented by the formula Ia,

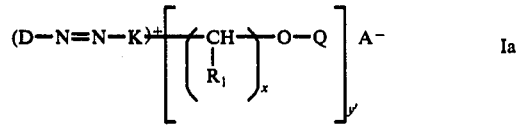

in which
R₁, Q, x and A⁻ are as defined above,
y' signifies 1 to 3, preferably 1 or 2, more preferably 1,
D signifies the radical of a diazo component,
K signifies the radical of a coupling component, the group(s) +CHR₁)ₓ—O—Q being attached to D and/or K; D and/or K containing a quaternary ammonium group.

In the compounds of formula Ia, the preferred significances of R₁, x, Q and A⁻ are as given above for the compounds of formula I. The quaternary ammonium group is preferably in D.

Representative of the compounds of formula Ia, are the compounds of formula Iaa,

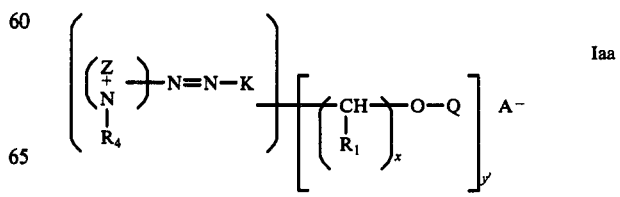

in which

K, $R_1$, $x$, $y'$, Q and $A^-$ are as defined above,

Z signifies a residue which, together with the nitrogen atom, forms an unsaturated heterocyclic ring containing at least five ring atoms, which may be carbon, oxygen, sulphur or further nitrogen atoms, which ring optionally has an aromatic carbocyclic or heterocyclic ring fused thereto and is, along with any ring fused thereto, optionally substituted by substituents selected from alkyl of 1 to 4 carbon atoms and alkoxy of 1 to 4 carbon atoms, each unsubstituted or substituted by phenyl, hydroxy, —CONH$_2$, cycloalkyl of 5 or 6 carbon atoms, cyano or halogen; cycloalkyl of 5 or 6 carbon atoms, unsubstituted or substituted by $C_{1-4}$ alkyl, $C_{1-4}$ alkoxy or halogen; phenyl or phenoxy, each unsubstituted or substituted by cyano, nitro, $C_{1-4}$ alkyl, $C_{1-4}$ alkoxy or halogen; halogen; nitro: cyano a radical of the formula —CO—Ro, $$-\underset{\underset{O}{\|}}{C}-O-Ro,$$

—NH—SO$_2$—Ro, —CO—NHRo, —CO—N(Ro)$_2$, —NH—CO—Ro, —SO$_2$—Ro, —SO$_2$—N(Ro)$_2$ or —SO$_2$—NHRo, in which Ro is as defined above; or phenylazo; the $$\widehat{Z + N} - R_4$$

group being free from water-solubilizing groups and containing at least one quaternary nitrogen atom, and being bound to the azo group through a carbon atom, and $R_4$ signifies a $C_{1-8}$ alkyl, $C_{2-8}$ alkenyl a or a $C_{1-4}$ alkoxy radical, each unsubstituted or substituted by halogen, hydroxy, phenyl, cyano, phenoxy, cycloalkyl or 5 or 6 carbon atoms, alkoxy of 1 to 4 carbon atoms or the group —CONH$_2$; a cycloalkyl radical of 5 or 6 carbon atoms, unsubstituted or substituted by $C_{1-4}$ alkyl, or radical of the formula —(CHR$_1$)$_x$—O—Q, in which $R_1$, $x$ and Q are as defined above. Any heterocyclic ring in $$\widehat{Z + N}$$

is preferably of 5 or 6 ring atoms and preferably contains 1, 2 or 3 heteroatoms.

As examples of radicals $$\widehat{Z + N}$$

may be given thiazolyl, isothiazolyl, thiadiazolyl, triazolyl, imidazolyl, indazolyl, oxazolyl, pyridinyl, pyrimidinyl, pyridazinyl, pyrazinyl, benzothiazolyl, oxadiazolyl, quinoxalinyl, cinnolinyl, phthalazinyl, pyrazolyl, naphthothiazolyl benzoxazolyl and benzimidazolyl derivatives.

Preferred examples of $$\widehat{Z + N}$$

are the triazolyl, pyridinyl and benzothiazolyl derivatives, more preferably the triazolyl derivatives.

In the compounds of formula Iaa, the preferred significances of $R_1$, $x$, Q and $A^-$ are as given above for compounds of formula I and Ia.

Preferred compounds of formula Iaa are the compounds of the formula Iaa', $$P - N = N - K' \quad A^- \qquad \text{Iaa}'$$

in which P signifies a radical of formula in which $R'_8$ signifies $R_8$ or V,
$R'_9$ signifies $R_9$ or V,
$R'_{10}$ signifies $R_{10}$ or V,
$R'_{11}$ signifies $R_{11}$ or V,
$R'_{12}$ signifies $R_{12}$ or V,
$R'_{16}$ signifies $R_{16}$ or V,
$R'_{17}$ signifies $R_{17}$ or V,
$R_8$ signifies an alkyl radical Z 1 to 4 carbon atoms or alkenyl radical of 2 to 4 carbon atoms, unsubstituted or substituted by hydroxy, halogen, cyano, phenyl or —CONH$_2$; or a cyclohexyl radical, unsubstituted or substituted by $C_{1-4}$ alkyl,
$R_9$ signifies an alkyl radical of 1 to 4 carbon atoms, unsubstituted or substituted by hydroxy, halogen, cyano, phenyl or —CONH$_2$; a cyclohexyl radical unsubstituted or substituted by $C_{1-4}$ alkyl; or a phenyl radical, unsubstituted or substituted by halogen, $C_{1-4}$ alkyl or $C_{1-4}$ alkoxy,
$R_{10}$ signifies hydrogen or one of the significances of $R_9$, above,
$R_{11}$ signifies $C_{1-4}$ alkoxy, $C_{1-4}$ alkyl or $C_{2-4}$ alkenyl, each unsubstituted or substituted by hydroxy, halogen, cyano, phenyl or —CONH$_2$,
$R_{12}$ signifies phenyl; halogen; nitro; cyano; $C_{1-4}$ alkyl or $C_{1-4}$ alkoxy;
$q$ signifies 0, 1 or 2, and when $q$ signifies 2, the $R_{12}$'s and $R'_{12}$'s may be the same or different,
either
$R_{16}$ and $R_{17}$, which may be the same or different, each signifies hydrogen; halogen; $C_{1-4}$ alkyl or $C_{1-4}$ alkoxy, unsubstituted or substituted by phenyl, hydroxy, —CONH$_2$, cycloalkyl of 5 or 6 carbon atoms, cyano or halogen; phenoxy; or a radical of the formula —CO—Ro, $$-\underset{\underset{O}{\|}}{C}-O-Ro,$$

—NH—SO₂—Ro, —CO—NH—Ro, —CON(Ro)₂,
—NH—CO—Ro, —SO₂—Ro, —SO₂—NH—Ro
or —SO₂—N(Ro)₂;

in which Ro is as defined above, or R₁₆ and R₁₇ are on adjacent carbon atoms and are linked to form a —CH=CH—CH=CH— linkage;

V signifies

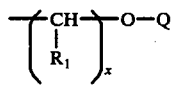

in which R₁, Q and x are as defined above,

A⁻ is as defined above, and

K' signifies a coupling component optionally substituted by V, where V is as defined above, with the proviso that the compounds contain from 1 to 3 V groups.

The compounds preferably contain 1 or 2 V groups, more preferably 1 V group.

In the compounds of the formulae Iaa and Iaa', K and K', respectively, may be, for example, of the benzene, naphthalene, heterocyclic or aliphatic series of coupling components. Suitable significances of K and K' will suggest themselves to those skilled in the art, and, as will be appreciated, the particular significance of K and K' is of minor consequence in the invention, provided that, where required, it can bear the V group.

In the compounds of formula Iaa', K may, for example, be a radical of formula,

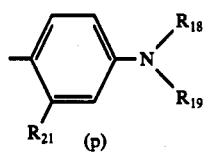 (p)   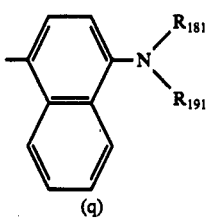 (q)

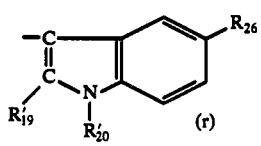 (r)   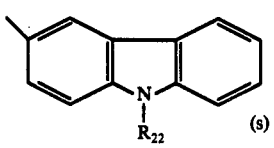 (s)

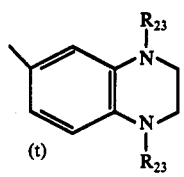 (t)   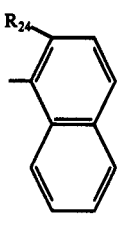 (u)

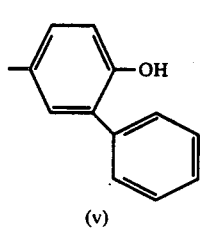 (v)   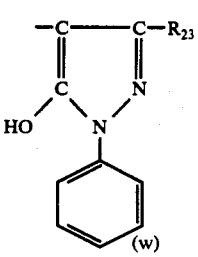 (w)

-continued

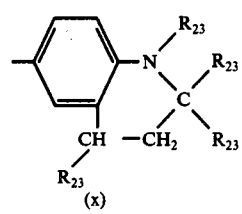 (x)   or   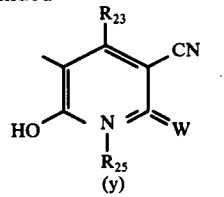 (y)

in which

R₁₈ and R₁₉, which may be the same or different, each signify hydrogen, or an alkyl radical of 1 to 4 carbon atoms unsubstituted or substituted by $C_{1-4}$ alkoxycarbonyl, benzoyloxy, phenoxy, halogen, preferably chlorine, hydroxy, phenyl, cyano, $C_{1-4}$ alkoxy, $C_{1-4}$ alkylcarbonyloxy, N,N—di($C_{1-4}$) alkylamino, or by the group V, or one of R₁₈ and R₁₉ signifies phenyl or cyclohexyl, the other having a significance as defined above, or R₁₈ and R₁₉, together with the nitrogen atom to which they are attached, signify

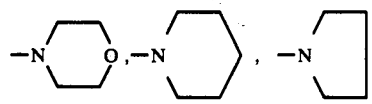

or

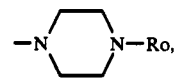

R₂₁ signifies a hydrogen atom, a $C_{1-4}$ alkyl or alkoxy radical or a halogen atom, R₁₉' signifies phenyl, $C_{1-4}$ alkyl, preferably methyl, unsubstituted or substituted by phenyl, e.g. benzyl, R₂₀' signifies hydrogen, phenyl or $C_{1-4}$ alkyl, preferably methyl, R₂₂ signifies $C_{1-4}$ alkyl, preferably methyl, the R₂₃'s which may be the same or different, each signifies $C_{1-4}$ alkyl, preferably methyl, R₂₄ signifies hydroxy, amino or monophenylamino, R₂₅ signifies hydrogen or an alkyl radical of 1 to 4 carbon atoms, unsubstituted or substituted by $C_{1-4}$ alkoxy, preferably methoxy, R₂₆ signifies hydrogen or halogen, e.g. chlorine, or $C_{1-4}$ alkyl or alkoxy, preferably hydrogen, R₁₈₁ and R₁₉₁, independently signify hydrogen or $C_{1-4}$ alkyl, or one of R₁₈₁ and R₁₉₁ signifies H or $C_{1-4}$ alkyl, and the other has one of the above significances of R₁₈ or R₁₉, and W signifies O or NH.

Preferred significances of K are (p) and (r) above, (p) being most preferred.

In the compounds of formula Iaa', V preferably is of formula V',

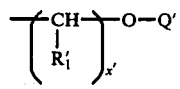  V' in which

R₁' signifies hydrogen or $C_{1-4}$ alkyl, x' signifies 1 or 2, and

Q' signifies an unsubstituted biphenylyl or dibenzofuranyl radical, preferably an o- or p-biphenylyl or a 3-dibenzofuranyl radical.

$R_1'$ is preferably hydrogen or methyl, more preferably hydrogen.

In the compounds of formula Iaa', P is preferably a radical of formula (a) or an isomer (b) or (c) thereof.

As will be appreciated, formulae (b) and (c) above, are isomeric forms of formula (a). For convenience, only one formula will be given hereinafter, it being understood to embrace the isomers thereof. Mixtures of the isomers are obtained when producing the compounds.

In the radical (a) or isomer (b) or (c) thereof, $R_8'$ preferably signifies $R_8$. $R_8'$ more preferably signifies an alkyl radical of 1 to 4, particularly 1 or 2, carbon atoms, unsubstituted or substituted by phenyl, e.g. a benzyl radical, hydroxy, e.g. 2-hydroxyethyl and 2-hydroxypropyl, or the group —$CONH_2$, e.g. $R_8$ most preferably signifies a methyl radical. $R_9'$ preferably signifies a radical of formula V', an unsubstituted $C_{1-4}$, more preferably $C_{1-2}$, alkyl radical, or a $C_{1-4}$, more preferably $C_{1-2}$, alkyl radical substituted by phenyl, e.g. a benzyl or phenylethyl radical, hydroxy, e.g. 2-hydroxyethyl and 2-hydroxypropyl, or the group —$CONH_2$, e.g. Most preferably $R_9$ signifies a methyl radical. $R_{10}'$ preferably signifies a radical of formula V', a hydrogen atom, a phenyl radical, a cyclohexyl radical, an unsubstituted $C_{1-4}$, more preferably $C_{1-2}$, alkyl radical, or a $C_{1-4}$ alkyl, more preferably $C_{1-2}$, alkyl radical substituted by phenyl, e.g. a benzyl radical. $R_{10}'$ most preferably signifies a hydrogen atom or a radical of formula V'.

K' preferably signifies radical (p) in which $R_{18}$ and $R_{19}$, independently, each signify an alkyl radical of 1 to 4 carbon atoms, unsubstituted or substituted by a radical of formula V', phenoxy, e.g. 2-phenoxyethyl, phenyl, e.g. benzyl, $C_{1-4}$ alkoxycarbonyl, e.g. 2-ethoxycarbonylethyl, or phenylcarbonyloxy, e.g. 2-phenylcarbonyloxyethyl. $R_{18}$ and $R_{19}$ more preferably signify, independently, a $C_{1-4}$ alkyl, particularly a methyl or ethyl, radical, unsubstituted or substituted by a radical V'. Most preferably, one of $R_{18}$ and $R_{19}$ signifies an ethyl radical, the other an ethyl radical, or a methyl radical substituted by a radical V'.

$R_{21}$ preferably signifies a hydrogen atom, a $C_{1-4}$ alkyl radical or a $C_{1-4}$ alkoxy radical. More preferably $R_{21}$ signifies a hydrogen atom or a methyl radical and, most preferably, signifies a hydrogen atom.

Where P signifies a radical of formula (d), $R_{11}$ preferably signifies an alkyl radical of 1 to 4, preferably 1 to 2, carbon atoms or an alkoxy radical of 1 to 4 carbon atoms, preferably a methoxy radical. $R_{11}$ most preferably signifies a methyl radical. $R_{12}$ preferably signifies a radical V', a $C_{1-4}$ alkyl radical, preferably a methyl radical, $C_{1-4}$ alkoxy radical, preferably a methoxy radical, or a halogen atom, preferably chlorine. q preferably signifies 0 or 1, most preferably 0.

Where P signifies a radical of formula (e), $R_8$ preferably signifies an alkyl radical of 1 to 4, preferably 1 to 2, carbon atoms, unsubstituted or substituted by —$CONH_2$, e.g. 2-carboxyamidoethyl. $R_{15}$ preferably signifies a methyl or ethyl radical, most preferably a methyl radical. $R_{16}'$ and $R_{17}'$ each preferably signify, independently, a radical V', hydrogen, chlorine, $C_{1-4}$ alkoxy, preferably methoxy, unsubstituted or substituted by phenyl, e.g. benzyloxy; $C_{1-4}$ alkylcarbonyl, preferably methylcarbonyl; $C_{1-4}$ alkylaminocarbonyl, perferably methylaminocarbonyl; phenylcarbonylamino; $C_{1-4}$ alkylsulphonylamino, preferably methylsulphonylamino; phenoxy; di-$C_{1-4}$ alkylaminosulfonyl (di-$C_{1-4}$ alkylsulfamoyl), preferably dimethylaminosulphonyl; or phenylsulphonyl, or $R_{16}$ and $R_{17}$ are on adjacent carbon atoms and form a —CH=CH—CH=CH— linkage. Most preferably one of $R_{16}$ and $R_{17}$ signifies hydrogen, the other methoxy.

Further preferred compounds of formula Iaa are the compounds of formula Iaa",

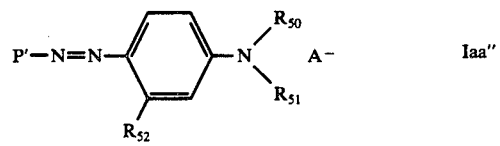

in which
P' signifies a radical of the formula

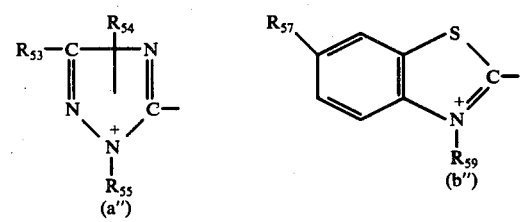

in which
$R_{53}$ signifies a hydrogen atom, a methyl radical, a phenyl radical, a benzyl radical or a radical of formula V",

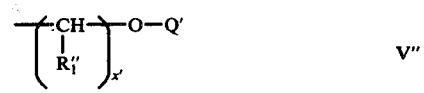

in which
$R_1''$ signifies a hydrogen atom or a methyl radical,
x' signifies 1 or 2, and
Q' signifies an o- or p-bisphenysyl radical or a 3-dibenzofuranyl radical,
$R_{54}$ and $R_{55}$, independently, signify an unsubstituted alkyl radical of 1 to 4 carbon atoms, preferably a methyl or ethyl radical, or an alkyl radical of 1 to 4 carbon atoms substituted by a hydroxy radical or $CONH_2$,
$R_{57}$ signifies a hydrogen atom or an alkoxy radical of 1 to 4 carbon atoms, preferably a methoxy radical,
$R_{59}$ signifies an alkyl radical of 1 to 4 carbon atoms, preferably a methyl or ethyl radical, unsubstituted or substituted by —$CONH_2$,
$R_{60}$ signifies an alkyl or alkoxy radical of 1 to 4 carbon atoms, preferably methyl or ethyl or methoxy,
$R_{50}$ signifies an alkyl radical of 1 to 4 carbon atoms, unsubstituted or substituted by phenyl, preferably an unsubstituted methyl or ethyl radical,
$R_{51}$ signifies an alkyl radical of 1 to 4 carbon atoms, preferably a methyl or ethyl radical, or a methyl radical substituted by a radical of formula V'", above, $R_{52}$ signifies a hydrogen atom or a methyl radical, preferably a hydrogen atom, and $A^-$ is as defined above, preferably a $Cl^-$, $ZnCl_3^-$, methylsulphate or acetate ion, with the proviso that the compound contains a radical of formula V'.

The compounds preferably contain only one radical of formula V''', most preferably on $R_{51}$.

Still further preferred compounds are the compounds of formula Iaa''',

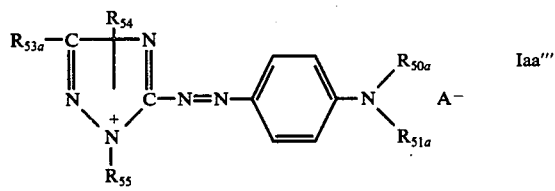

in which $R_{53a}$ signifies a hydrogen atom or a radical of formula V''', above, $R_{54}$ and $R_{55}$ are as defined above, $R_{50a}$ signifies an unsubstituted alkyl radical of 1 to 4 carbon atoms, preferably a methyl, ethyl or butyl radical, more preferably an ethyl radical, $R_{51a}$ signifies an unsubstituted alkyl radical of 1 to 4 carbon atoms, e.g. a methyl, ethyl or butyl radical, or a methyl radical substituted by a radical V''', above, $A^-$ is as defined above, preferably a $Cl^-$, $ZnCl_3^-$, methylsulphate or acetate ion, with the proviso that the compound contains one radical of formula V'.

$R_{53a}$ preferably signifies hydrogen.

The styryl dyes provided by the invention may, for example, be represented by the formula Ib,

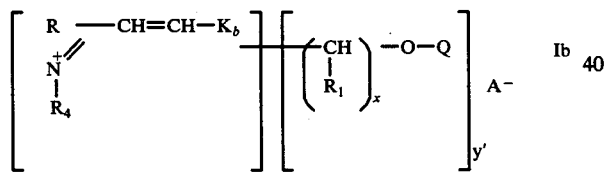

in which $R_4$, $R_1$, x, Q, y' and $A^-$ are as defined above,

R signifies a residue which, together with the nitrogen atom, forms an unsaturated heterocyclic ring of 5 to 7 ring atoms, which ring optionally has an aromatic carbocyclic or heterocyclic ring fused thereto and is, along with any ring fused thereto, optionally substituted by substituents selected from alkyl of 1 to 4 carbon atoms and alkoxy of 1 to 4 carbon atoms, each unsubstituted or substituted by phenyl, hydroxy, -$CONH_2$, cycloalkyl of 5 or 6 carbon atoms, cyano or halogen; cycloalkyl of 5 or 6 carbon atoms, unsubstituted or substituted by $C_{1-4}$ alkyl, $C_{1-4}$ alkoxy or halogen; phenyl or phenoxy, each unsubstituted or substituted by cyano, nitro, $C_{1-4}$ alkyl, $C_{1-4}$ alkoxy or halogen; a radical of the formula -CO-Ro,

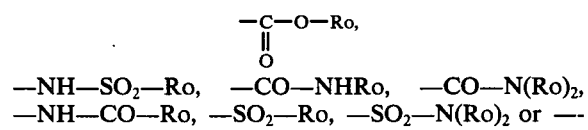

—NH—$SO_2$—Ro, —CO—NHRo, —CO—N(Ro)$_2$, —NH—CO—Ro, —$SO_2$—Ro, —$SO_2$—N(Ro)$_2$ or —$SO_2$—NHRo, in which Ro is as defined above; or phenylazo; the

group being free from water-solubilizing groups and being bound to the azo group through a carbon atom, and $K_b$ signifies an aromatic residue of the benzene, naphthalene or heterocyclic series, the $+CHR_1)_xO$—Q group(s) being bound to the residue $K_b$ and/or to the radical

In the compounds of formula Ib, the preferred significances of $R_1$, x, Q and $A^-$ are as given above for the compounds of formulae I and Ia. R preferably forms an unsaturated heterocyclic ring of 5 ring atoms, which may have a carbocyclic ring fused thereto, preferably to form a 6-membered ring therewith.

Suitable significances of $K_b$ will suggest themselves to those skilled in the art, and, as will be appreciated, the particular significance of $K_b$ is of minor consequence in the invention, provided that, where required, it can bear the group $+CHR_1)_xO$—Q.

Preferred compounds of formula Ib are the compounds of formula Ib',

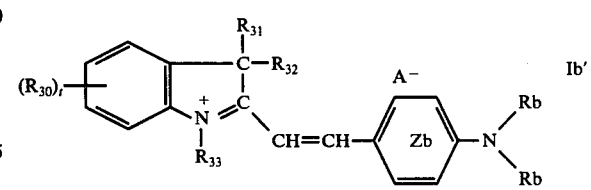

in which $R_{30}$ signifies hydroxy; halogen; preferably chlorine; unsubstituted alkyl of 1 to 4 carbon atoms, preferably methyl; unsubstituted $C_{1-4}$ alkoxy, preferably methoxy; $C_{1-4}$ alkyl or alkoxy substituted by a radical V, above, phenyl, $C_{5-6}$ cycloalkyl; nitro; trifluoromethyl; phenoxy; a radical of the formula —CO—Ro,

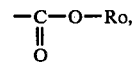

—NH—$SO_2$—Ro, —CO—NH—Ro, —CON(Ro)$_2$, —NH—CO—Ro, —$SO_2$—Ro, —$SO_2$—NH—Ro or —$SO_2$—N(Ro)$_2$; in which Ro is as defined above, $R_{31}$ and $R_{32}$, which may be the same or different, each signify an alkyl radical of 1 to 4 carbon atoms, e.g. methyl, ethyl, propyl or butyl, preferably methyl, $R_{33}$ signifies an alkyl radical of 1 to 4 carbon atoms or alkenyl radical of 2 to 4 carbon atoms, unsubstituted or substituted by hydroxy, cyano, phenyl or the group —$CONH_2$; a cyclohexyl radical unsubstituted or substituted by $C_{1-4}$ alkyl; or the radical V, ring Zb is further unsubstituted or further substituted by up to 2 substituents selected from $C_{1-4}$ alkoxy, $C_{1-4}$ alkyl or halogen, either the Rb's, which are the same or different, each signify $C_{1-4}$ alkyl, unsubstituted or substituted by $C_{1-4}$ alkoxycarbonyl, phenylcarbonyloxy, phenoxy, halogen, preferably chlorine, hydroxy, phenyl, cyano, C$_{1-4}$ alkoxy, C$_{1-4}$ alkylcarbonyloxy, N,N-di(C$_{1-4}$)alkylamino, or by the group V, or one of the Rb's signifies phenyl or cyclohexyl, the other signifying one of the above significances of Rb, above, or the Rb's are joined to form, with the nitrogen atom, a group

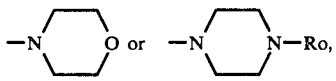

in which Ro is as defined above, preferably methyl,
A$^-$ is as defined above, preferably Cl$^-$, ZnCl$_3^-$, methylsulphate or acetate,
t signifies o, 1 or 2 and, where t signifies 2, the R$_{30}$'s may be the same or different,
with the proviso that the compounds contain 1 to 2 V groups, preferably 1 V group.

Further preferred compounds of formula Ib are the compounds of formula Ib'',

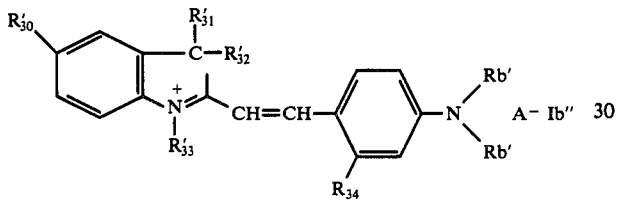

in which
R'$_{30}$ signifies hydrogen, halogen, preferably chlorine, unsubstituted alkyl of 1 to 4 carbon atoms, preferably methyl, alkoxy of 1 to 4 carbon atoms, preferably methoxy, phenoxy, benzyloxy, phenyl, cyano, nitro, phenylcarbonyl, phenylsulphonyl, methoxycarbonyl, dimethylaminosulfonyl (dimethylsulfamoyl), trifluoromethyl or a radical of formula Vb, i.e. -(-CHRb-)$_{\overline{u}}$Qb, in which Rb signifies methyl or hydrogen, u signifies 1 or 2 and Qb signifies an unsubstituted o- or p-biphenylyl or 3-dibenzofuranyl radical,
R'$_{31}$ signifies a methyl radical,
R'$_{32}$ signifies a methyl radical,
R'$_{33}$ signifies an alkyl radical of 1 to 4 carbon atoms, unsubstituted or substituted by hydroxy, preferably a methyl or ethyl radical or a 2-hydroxypropyl radical,
R$_{34}$ signifies hydrogen or a methyl radical,
the
Rb's, which are the same or different, each signify an alkyl radical of 1 to 4 carbon atoms, unsubstituted or substituted by cyano or by a radical of formula Vb, above,
A$^-$ is as defined above, preferably a Cl$^-$, ZnCl$_3^-$, methylsulphate or acetate ion,
with the proviso that the compounds contain a Vb group.

Still further preferred compounds of formula Ib are the compounds of formula Ib''',

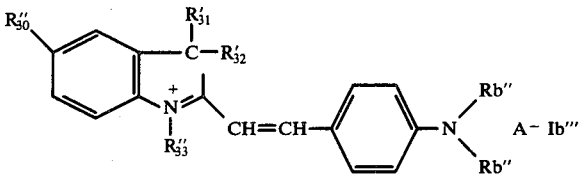

in which
R''$_{30}$ signifies hydrogen or chlorine, or a group of the formula —CH$_2$—O—Qb in which Qb is as defined above,
R'$_{31}$ and R'$_{32}$ are as defined above,
R''$_{33}$ signifies a methyl radical,
and the
Rb''' 's, which are the same or different, each signify a methyl radical, an ethyl radical, a cyanoethyl radical or a methyl radical substituted by a group of the formula —CHRs—O—Qb, in which Qb is as defined above, and Rs signifies a hydrogen atom or a methyl radical,
A$^-$ is as defined above, preferably a Cl$_-$, ZnCl$_{3-}$, methylsulfate or acetate ion, more preferably a Cl$_-$ ion,
with the proviso that the compounds contain one —CHRs—O—Qb or —CH$_2$—O—Qb radical.

The methine and azo azomethine dyes provided by the invention may, for example, be represented by the formula Ic,

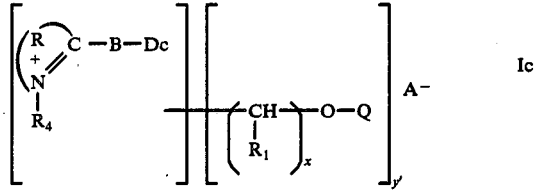

in which
R, R$_1$, R$_4$, x, y', Q and A$^-$ are as defined above,
B signifies a linkage (a)

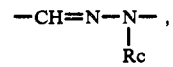

or a linkage (b)

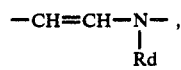

Rc signifies hydrogen, C$_{1-4}$ alkyl preferably methyl, unsubstituted or substituted by hydroxy,
Rd signifies hydrogen, C$_{1-4}$ alkyl or a C$_{2-3}$, preferably C$_3$, alkylene bridge, linked to Dc to form a ring, which alkylene bridge is unsubstituted or substituted by 1 to 3, preferably 1, C$_{1-4}$alkyl groups, preferably methyl,
Dc signifies the radical of a diazo component, the —CHR$_1$)$_x$O—Q
group(s) being bound to the residue Dc and/or to the radical

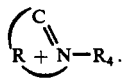

In the compounds of formula Ic, the preferred significances of $R_1$, $x$, Q, and $A^-$ are as given above for the compounds of formula I and Ia. Rd preferably signifies hydrogen.

Suitable significances of Dc will suggest themselves to those skilled in the art, and, as will be appreciated, the particular significances of Dc is of minor consequence in the invention, provided that, where required, it can bear the group $-(CHR_1)_x Q-Q$.

Preferred compounds of formula Ic are the compounds of formula Ic'.

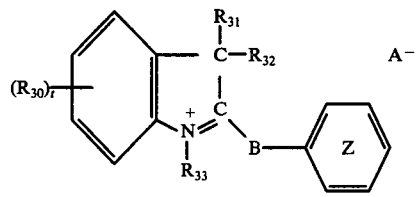

in which
$R_{30}$, $R_{31}$, $R_{32}$, $R_{33}$, $t$ and B are as defined above, and
Z is further unsubstituted or further substituted by up to 2 substituents selected from $C_{1-4}$ alkoxy, $C_{1-4}$ alkyl, halogen, the group V, or methoxy substituted by V, or, where B signifies

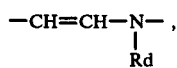

the group Rd may be linked to Z, at the o-position, to form a $C_3$ alkylene bridge, unsubstituted or substituted by a $C_{1-4}$ alkyl, preferably methyl, group.

Representative further preferred compounds of formula Ic are the compounds of formula Ica',

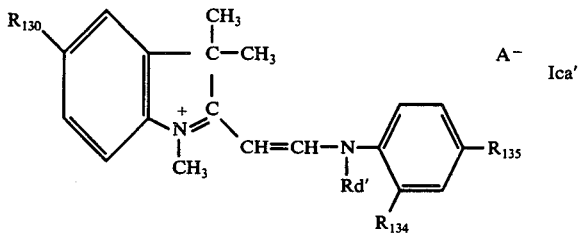

in which
$R_{130}$ signifies hydrogen or chlorine, or a radical of the formula $-(CHRca)_{n''}OQca$,
in which Rca signifies hydrogen or methyl, preferably hydrogen, $n''$ signifies 1 or 2, preferably 1, and Qca signifies an unsubstituted o- or p-biphenylyl or 3-dibenzofuranyl radical,
either
R'd signifies hydrogen or methyl, preferably hydrogen, and
$R_{134}$ signifies hydrogen, methoxy or methyl,
or R'd and $R_{134}$ are linked to form a

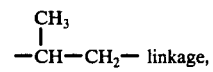

and
$R_{135}$ signifies methoxy, unsubstituted or substituted by a radical of the formula $-(CHRca)_{n''}O-Qca$,
in which Rca, $n''$ and Qca are as defined above, Qca preferably signifing an unsubstituted o- or pi-biphenylyl or 3-dibenzofuranyl radical,
the compounds containing one $-(CHRca)_{n''}OQca$ radical,
$A^-$ is as defined above, preferably a $Cl^-$, $ZnCl_3^-$, methylsulfate or acetate ion.

The preferred compounds of formula Ica' are the compounds of formula Ica'',

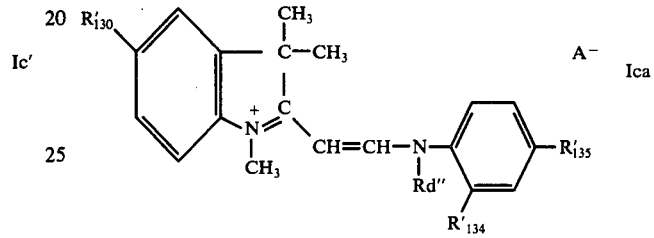

in which either
Rd'' and $R'_{134}$ each signify hydrogen,
or Rd'' and $R'_{134}$ are joined to form a $-CH(CH_3)-CH_2-$ linkage,
$R'_{130}$ signifies hydrogen or $-CH_2-O-Qca'$, in which Qca' signifies an unsubstituted o- or p-biphenylyl radical, and
$R'_{135}$ signifies hydrogen, methoxy, the group $-CHRca'-O-Qca'$, in which Rca' signifies hydrogen or methyl and Qca' is as defined above, or a methoxy radical substituted by a group $-CH_2-O-Qca'$, in which Qca' is as defined above, the compounds containing one $-CH_2-O-Qca'$ or $-CHRca'-O-Qca'$ group,
$A^-$ is as defined above, preferably a $Cl^-$, $ZnCl_3^-$, methylsulphate or acetate ion, more preferably a $Cl^-$ ion.

Other representative compounds of formula Ic' are the compounds of formula Icb',

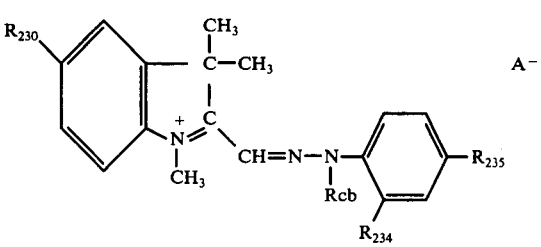

in which
$R_{230}$ signifies hydrogen; chlorine; dimethylaminosulphonyl; methoxycarbonyl; or a radical of the formula $-(CHRca)_{n''}O-Qca$, in which $n''$ and Qca are as defined above,
Rcb signifies hydrogen, methyl or $C_{1-3}$ alkyl substituted by hydroxy,
$R_{234}$ signifies hydrogen, methyl or methoxy, $R_{235}$ signifies methyl; methoxy, unsubstituted or substituted by a radical of the formula $-(CHRca)_{n''}$ O—Qca, in which $n''$ and Qca are as defined above; or a $-(CHRca)_{n''}$O—Qca radical, A⁻ being as defined above, preferably a Cl⁻, ZnCl₃⁻, acetate or methylsulphate ion, the compounds containing one $-(CHRca)_{n''}$ O—Qca radical.

The preferred compounds of formula Icb' are the compounds of formula Icb'',

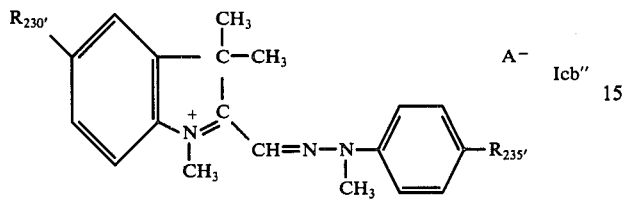

in which
$R_{230'}$ signifies hydrogen or a radical —CH₂—O—Qcb, in which Qcb signifies an o- or p-biphenylyl radical, and $R_{235'}$ signifies a methoxy group, unsubstituted or substituted by a group —CH₂—O—Qcb, in which Qcb is as defined above; or a group $-(CH_2)_{n''}$O—Qcb, in which $n''$ and Qcb are as defined above, A⁻ is as defined above, preferably a Cl⁻, ZnCl₃⁻, methylsulphate or acetate ion, more preferably a Cl⁻ or methylsulphate ion, the compounds containing one —CH₂—OQcb or $-(CH_2)_{n''}$ OQcb radical.

The anthraquinone dyes of the invention may be represented by the formula Id,

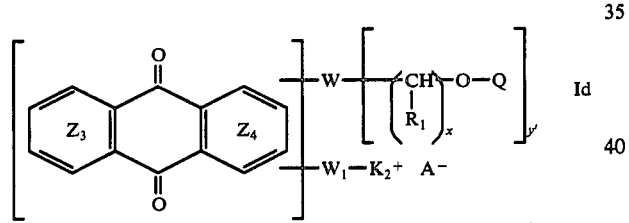

in which $R_1$, $x$, $Q$, $Y'$ and $A^-$ are as defined above,
W signifies a direct bond or a $Y' + 1$ valent bridging radical
$W_1$ signifies a divalent bridging radical,
$K_2^+$ signifies an ammonium, hydrazinium, etherified hydroxylammonium or cycloimmonium group,
W and $W_1$ being bound, independently, to ring $Z_3$ or $Z_4$, and
rings $Z_3$ and $Z_4$ are optionally further substituted.

Representative of the compounds of formula Id are the compounds of formula Id',

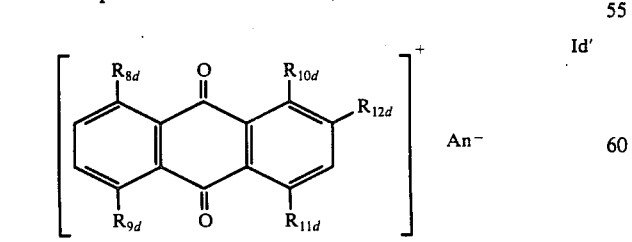

in which
$R_{8d}$ and $R_{9d}$, independently, signify hydrogen, halogen, —NO₂, —NH₂ or —OH, a mono($C_{1-4}$) alkylamino or di-($C_{1-4}$) alkylamino radical, a mono- phenylamino (anilino) radical, a phenoxy radical or a monocyclohexylamino radical, $R_{10d}$ and $R_{11d}$ each signify a substituent selected from —O—T, —NH—T or —S—T, in which T signifies (a) hydrogen; (b) $C_{1-4}$ alkyl, unsubstituted or substituted by hydroxy and/or chlorine; (c) cyclohexyl; (d) phenyl; (e) —CH₂Vd, or (f) a group

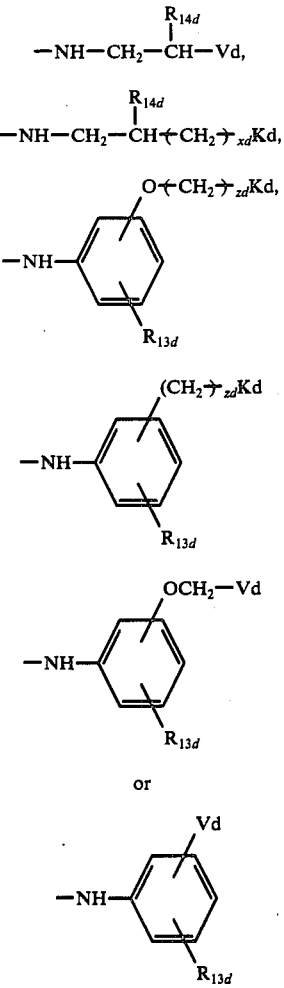

in which
Vd signifies $-(CH_2)_{nd}$—O—Qd, where nd signifies 1, 2 or 3 and Qd signifies an unsubstituted o- or p-biphenylyl or 1—, 2—, 3—, preferably 3—, dibenzofuranyl radical
$R_{13d}$ signifies hydrogen, $C_{1-4}$ alkyl, preferably methyl, halogen, preferably chlorine, or $C_{1-4}$ alkoxy, preferably methoxy,
$R_{41d}$ signifies hydrogen, hydroxy or methoxy,
xd signifies 0, 1 or 2,
zd signifies 1 or 2,
Kd signifies a pyridinium radical or a radical

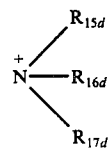

in which $R_{15d}$ signifies hydrogen, —$NH_2$ or alkyl of 1 to 4 carbon atoms $R_{16d}$ signifies a $C_{1-4}$ alkyl radical, and $R_{17d}$ signifies a $C_{1-4}$ alkyl radical, a cyclohexyl radical or a phenyl radical, or $R_{15d}$ and $R_{16d}$ are joined to form a heterocyclic ring of 5 or 6 ring atoms, such as a pyrolidino, piperidino or morpholino ring, or $R_{15d}$, $R_{16d}$, and $R_{17d}$ together with the nitrogen atom form

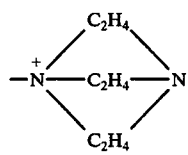

$R_{12d}$ signifies hydrogen, cyano, halogen, preferably bromine, $C_{1-4}$ alkyl, preferably methyl, $C_{1-4}$ alkoxy, preferably methoxy, phenoxy or a radical —CONH—$CH_2$-(-$CH_2$-)$_t$OQd where t signifies 1, 2 or 3, or

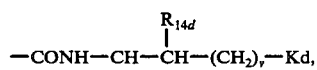

where v signifies 0, 1, 2 or 3, and $A^-$ is as defined above, preferably a $Cl^-$, $ZnCl_3^-$, methylsulphate or acetate ion, with the proviso that the compounds contain one Qd group and one Kd group.

Preferred compounds or formula Id' are the compounds of formula Id",

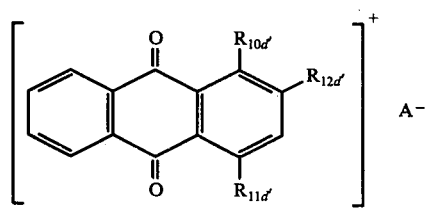

in which $R_{10d'}$ signifies —$NH_2$, —NH—$CH_2$—Vd',

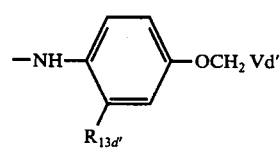

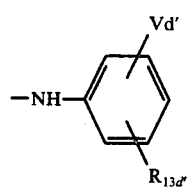

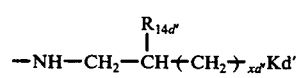

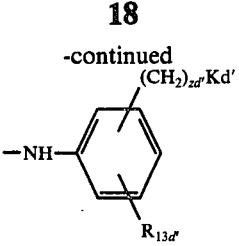

or

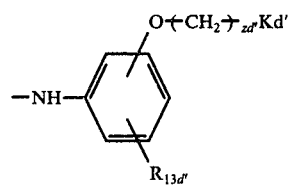

in which

Vd' signifies -(-$CH_2$-)$_{nd'}$O-Qd' in which nd' signifies 1 or 2 and Qd' signifies an unsubstituted o-or p-biphenylyl or 3-dibenzofuranyl radical, $R_{13d}$ signifies hydrogen or methyl, $R_{14d}$ signifies hydrogen, hydroxy or methoxy, xd' signifies 0, 1 or 2, zd' signifies 1 or 2, and Kd' signifies pyridinium or

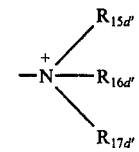

in which $R_{15d'}$ signifies hydrogen, —$NH_2$, or alkyl of 1 to 4, preferably 1 or 2, carbon atoms, $R_{16d'}$ and $R_{17'}$, which may be the same or different, each signify a $C_{1-4}$, preferably $C_{1-2}$, alkyl radical, $R_{11d'}$ signifies one of the above significances of $R_{10d}$, other than —$NH_2$, $R_{12d'}$ signifies hydrogen, halogen, preferably bromine, the group —CONH—$CH_2$—Vd', in which Vd' is as defined above, or —CONH-(-$CH_2$-)$_{yd'}$ Kd', in which Kd' is as defined above, and yd' signifies 2 or 3, preferably 3, and $A^-$ is as defined above, preferably a $Cl^-$, $ZnCl_3^-$, methylsulfate or acetate ion, with the proviso that the compounds contain one Vd' group and one Kd' group.

Further preferred compounds of formula Id are the compounds of formula Id''',

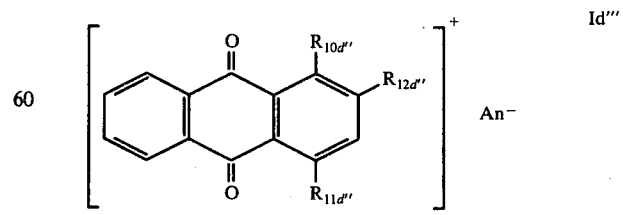

in which $R_{12d''}$ signifies hydrogen or —CONH-(-$CH_2$-)$_3$$N^+$($CH_3$)$_3$ $R_{10d''}$ signifies —NH$_2$, a group —NH—C$_2$H$_4$—O—Qd',

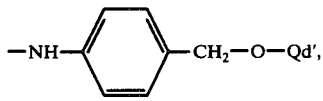

in which

Qd' is as defined above; a group

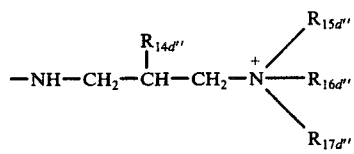

or a group

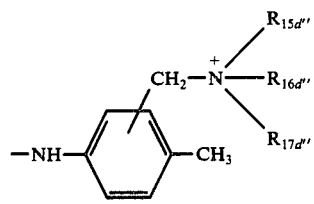

in which $R_{14d}$ signifies hydrogen or hydroxy, preferably hydrogen;

$R_{15''}$, $R_{16''}$ and $R_{17''}$, each independently, signify an alkyl radical of 1 or 2 carbon atoms, preferably —CH$_3$, $R_{11d''}$ signifies one of the above significances of $R_{10d''}$, other than —NH$_2$, A$^-$ is as defined above, preferably a Cl$^-$, ZnCl$_3^-$, methylsulfate or acetate ion, more preferably a methylsulfate ion, with the proviso that the compounds contain one Qd' group and one quaternary ammonium group.

The compounds of formula I may be produced in conventional manner from available starting materials using conventional techniques such as quaternisation, condensation, protonisation and diazo coupling reactions, depending on the type of compound of formula I desired.

Thus, for example, where it is desired to obtain a compound of formula Ip,

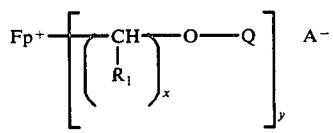

in which $R_1$, x, y, Q and A$^-$ are as defined above, and

Fp$^+$ signifies a dye residue containing a quaternary ammonium group, such may be obtained by quaternishing a compound of formula IIp,

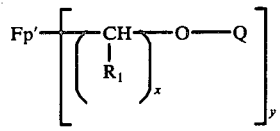

in which Fp" signifies a dye residue containing a quaternisable amine group.

The quaternisation may be carried out in conventional manner.

In particular, the invention provides a process for the production of compounds of formulae Iaa, Ib and Ic, characterised by quaternising, using an R$_4$ yielding quaternising agent, corresponding compounds of formulae IIaa, IIb and IIc,

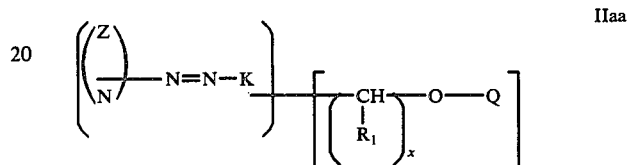

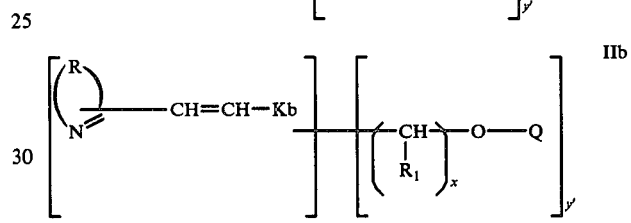

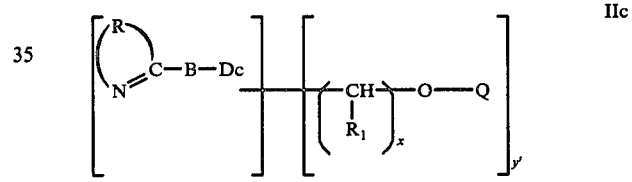

The quaternisation may suitably be carried out by reaction with a compound of formula III, $$R_4 - A \qquad \text{III}$$

in which

R$_4$ is as defined above, and A corresponds to A$^-$, above, or by addition reaction of an R$_4$ yielding epoxide or vinyl compound with a compound of formula II, in the presence of water and with neutralization employing an acid HA.

The quaternisation with a compound of formula III may be carried out in conventional manner. Suitably, the reaction is carried out in an inert solvent, in an aqueous suspension or, where liquid under the reaction conditions, in an excess of the compound of formula III. Where necessary, the reaction can be carried out at elevated temperatures and in a buffered medium. As examples of preferred quaternising agents of formula III may be given methyl or ethyl chloride, bromide or iodide, alkyl sulphates, such as dimethyl sulphate, or benzyl chloride. As examples of other quaternising agents may be given acrylic acid amide hydrochloride, such as CH$_2$=CH—CO—NH$_2$/HCl, chloroacetic acid amide, or epoxides such as ethylene oxide and propylene oxide, and epichlorohydrins, in the presence of an acid of the formula HA.

The compounds of formula Ia, above, may be produced by reacting the diazo derivative of a compound of formula IV,

D — NH$_2$     IV with a coupling component of formula VI,

H — K     VI

The coupling reaction can be carried out in conventional manner, for example in an aqueous medium at a temperature of from −10° to 20° C. The reaction medium may be bufferred, acid, neutral or alkaline.

The compounds of formula Ib, stated above, may alternatively be produced by condensing a compound of formula VII,

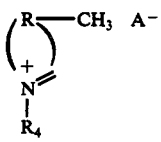

with an aldehyde of formula VIII,

Kb — CHO     VIII

The condensation may be carried out in conventional manner.

The methine compounds of the invention may be produced by reacting a compound of the formula IX,

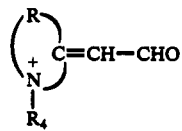

with a compound of formula

Dc — NH — Rd     X in the presence of a salt.

The reaction is carried out in conventional manner.

The compunds of formula Id may be produced, for example, by reacting a compound of formula IId,

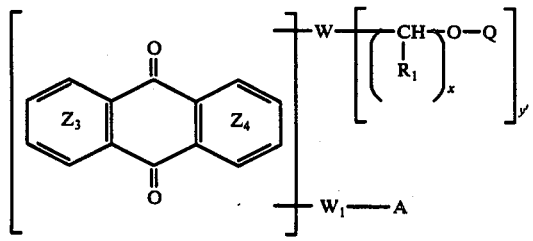

in which

A signifies an A$^-$ yielding radical, with a compound K$_2$, i.e. a K$_2$$^+$ yielding compound.

The reaction may be carried out in conventional manner.

Suitable examples of K$_2$ include pyridine and compunds of the formula

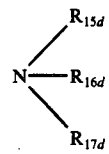

in which

R$_{15d}$, R$_{16d}$ and R$_{17d}$ are as defined above.

As examples of alkyl and alkoxy radicals of 1 to 4 carbon atoms, as used herein, may be given methyl, ethyl, n-propyl, isopropyl and n-butyl and the corresponding alkoxy radicals. Unless otherwise stated, the prefered such radicals are methyl, ethyl, methoxy and ethoxy, methyl and methoxy being most preferred. By the term halogen, as used herein, is meant chlorine, bromine and iodine; chlorine an bromine being preferred, chlorine being most preferred.

The compounds of formula I are useful as dyes. They may be converted into dyeing preparations, e.g. into stable, liquid or solid dyeing preparations, in conventional manner, e.g. by grinding or granulating or dissolving in conventional dyestuff solvents, if necessary with the addition of assistants such as stabilizers. Such preparations may be produced, for example, in accordance with Frensh Pat. No. 1,572,030 and 1,581,900.

The compounds of formula I may be used in the dyeing or printing of textile substrates, whether in fibre, yarn or fabric form, which consist of or comprise homopolymers or co-polymers of acrylonitrile or asymmetrical dicyanoethylene. The dyeing of such substrates may be carried out in conventional manner.

The compounds of formula I may also be used for dyeing or printing substrates of synthetic polyamide or synthetic polyester fibres, modified by the introduction of acid groups. Polyamides of this type are described in Belgian Pat. No. 706,104 and polyester fibres of this type are described in U.S. Pat. No. 3,379,723. The dyeing of such substrates may be carried out in conventional manner. It is advantageous to dye in an aqueous, neutral, or acid medium, at from 60° C to the boil or at temperatures above 100° C under pressure.

The dyeings obtained with the compounds of formula I are level, have stable light fastness as well as good wet fastness properties, e.g. to washing, perspiration, sublimation, pleating, decatizing, pressing, steam, water, sea water, dry cleaning, crossdyeing and solvents. The dyes are well soluble in water, show good compatibility with salt, good stability to boiling, good pH stability and partly reserve fibres other than those on which they are dyeable. Further, they possess good power of build-up in combination with other basic dyes.

The compounds, which have good solubility in organic solvents, may also be used for the dyeing of natural or synthetic resins in the mass, being incorporated therein in conventional manner, e.g. by intimate admixture therein, for example by milling, optionally with the use of a solvent.

It has been found that mixtures of two or more of the compounds of the present invention or of one of the compounds of the present invention and other cationic dyes can be used with advantage.

The following Examples, in which parts and percentages are by weight and temperatures are in degrees centigrade, illustrate the invention.

EXAMPLE 1

26.6 Parts of 3-para-diphenoxymethyl-5-amino-1,2,4-triazole are dissolved at 70° in 150 parts of glacial acetic acid and diluted with 10 parts of propionic acid and 18 parts of phosphoric acid. The solution is cooled to −5° -0° and 21 parts of 4/normal sodium nitrite solution are added dropwise. The diazo solution is added dropwise over the course of 30 minutes to a solution consisting of 15 parts of N,N-diethylaniline, 5 parts of aminosulphonic acid, 50 parts of glacial acetic acid, and 25 parts of water. 100 parts of ice are added simultaneously to keep the temperature at 0 to 5°. The solution is diluted with 160 parts of isopropanol and 100 parts of ice and the pH is adjusted to 5 by the addition of 110 parts of sodium acetate. Stirring is effected and a crystalline dye obtained. The dye is filtered with suction, washed twice, each time with 100 parts of water, and dried at 50° under vacuum.

30.5 parts of the dried and finely ground dye are added to 300 parts of butanol, the mixture is stirred and 3.5 parts of magnesium oxide and 25 parts of dimethyl sulphate are added. The suspension is subsequently heated to 45°–50° over the course of 3 hours. After cooling to room temperature, the dye solution is shaken twice, each time with 150 parts of 26% brine and concentrated by vacuum evaporation of 50°–60°. The residue is dissolved in 300 parts of water at 80°, 15 parts of "Hyflo" and 10 parts of "Norit Supra" are added and after 15 minutes it is filtered by means of a talc filter. The filtrate is washed with 750 parts of water of 50° and the dye is salted out with 70 parts of sodium chloride. Stirring is effected and the crystalline dye is filtered with suction and washed with 100 parts of 5% aqueous sodium chloride solution. After drying at 40° in a vacuum, there are obtained 30.8 parts of the dye of the formula

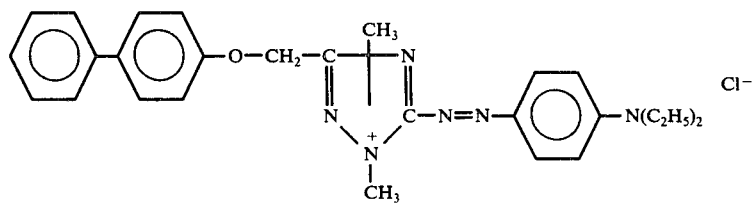

Applied on polyacrylonitrile fibres and polyester fibres, modified by the introduction of acid groups, this dye gives fast bluish red dyeings.

Using 26.6 parts of 3-(ortho-diphenoxy)-methyl-5-amino-1,2,4-triazole instead of the above diazo component, a dye of the formula

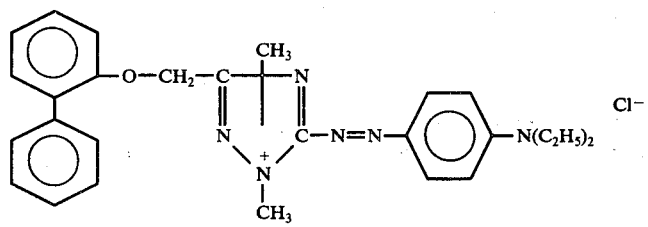

is obtained in accordance with the same process. Applied on polyacrylonitrile fibres and polyester fibres, modified by the introduction of acid groups, this dye gives fast bluish red dyeings.

EXAMPLE 1a

Using 28.0 parts of 3-(3'-dibenzofuranoxy)-methyl-5-amino-1,2,4-triazole instead of the above diazo component, a dye of the formula

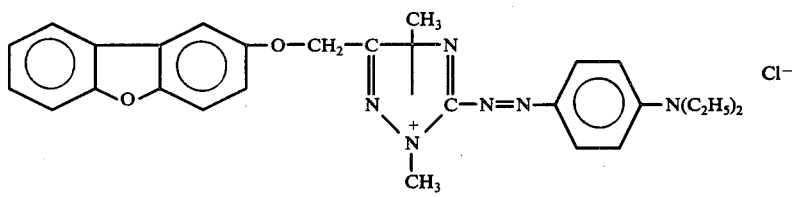

is obtained in accordance with the same process. Applied on polyacrylonitrile fibres and polyester fibres, modified by the introduction of acid groups, this dye gives fast bluish red dyeings. The above diazo components 3-P-diphenoxymethyl-5-amino-1,2,4-triazole or 3-ortho-diphenoxymethyl-5-amino-1,2,4-triazole or 3-(3'-dibenzofuranoxy)-methyl-5-amino-1,2,4-triazole may be obtained, for example, by melting the corresponding diplenoxyacetic acetic acids or dibenzofuranoxyacetic acetic acid with aminoguanidine bicarbonate at 170°–190°. The diphenoxyacetic acetic acids may be obtained by reaction of monochloroacetic acid with the sodium salt of the corresponding diphenol or 3-hydroxydibenzofuran.

EXAMPLE 2

8.4 parts of 3-amino-1,2,4-triazole are dissolved in 22 parts of 62% nitric acid and 18 parts of water, 20 Parts of ice are added and 20.8 parts of an aqueous 4/normal sodium nitrite solution are subsequently added dropwise over the course of 20 minutes. After 30 minutes the excess nitrite is decomposed with 0.4 parts of aminosulphonic acid. The diazo solution is added dropwise over the course of 20 minutes to a solution consisting of 31.7 parts of the coupling component of the formula

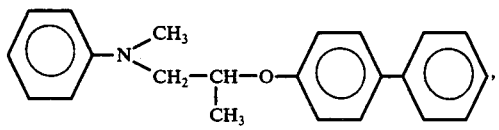

100 parts of glacial acetic acid, 50 parts of dimethylformamide and 2 parts of aminosulphonic acid. The pH is adjusted to 4.0–4.5 by the addition of sodium hydroxide and the suspension is stirred over the course of 20 hours and the precipitated dye is filtered 23 Parts of the dried and ground dye are dissolved in 110 parts of chloroform at 50° and 4 parts of magnesium oxide are added. 16.5 Parts of dimethyl sulphate are added dropwise over the course of 15 minutes and the mixture is stirred at 50°–55° over the course of 3 hours. After cooling to room temperature, the suspension is diluted with 150 parts of chloroform and filtered over Hyflo. The solvent is removed in a vacuum and the oily residue is taken up in 300 parts of water and 90 parts of ethanol and salted out with 15 parts of common salt. After stirring for 2 hours, the precipitated dye is filtered off and dried at 50° in a vacuum. Thus, 23.7 parts of the dye of the formula

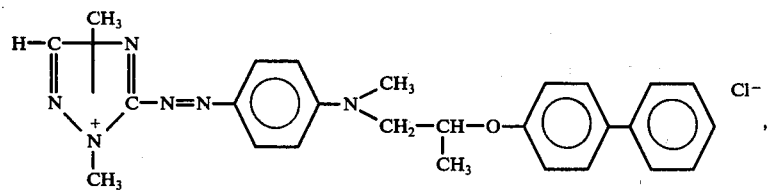

are obtained. Applied on polyacrylonitrile fibres and polyester fibres, modified by the introduction of acid groups, this dye gives fast bluish red dyeings. Using 31.7 parts of the compound of the formula

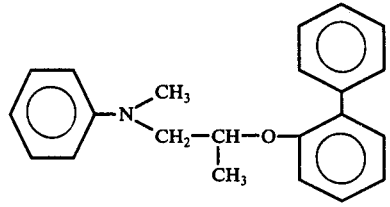

instead of the above-mentioned coupling component, a dye of the formula

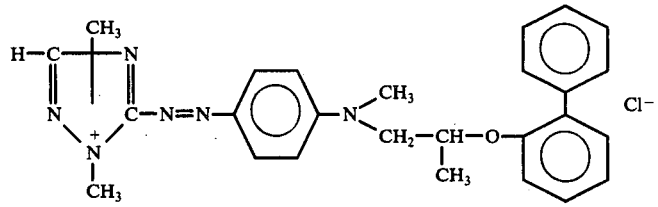

is obtained in accordance with the same process. Applied to polyacrylonitrile fibres or polyester fibres, modified by the introduction of acid groups, this dye gives fast bluish red dyeings.

EXAMPLE 2a

Replacing the above coupling component by 33.1 parts of the compound of the formula

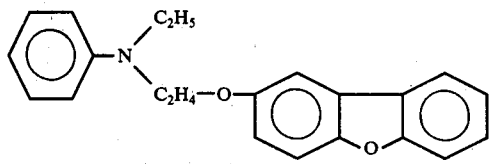

a dye of formula

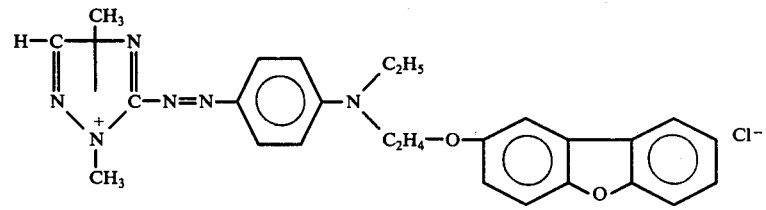

is obtained in accordance with the same process. Applied on polyacrylonitrile fibres or polyester fibres, modified by the introduction of acid groups, this dye gives fast bluish red dyeings. The above-mentioned coupling components N-methyl-N-2'-methyl-2'-(p-diphenoxy)-ethylaniline, N-methyl-N-2'-methyl-2'-(o-diphenoxy)-ethylaniline or N-ethyl-N-2'-(3''-dibenzofuranoxy)-ethylaniline may be obtained by condensation of N-ethyl-N-2'-chloroethylaniline with p-phenylphenol, o-phenylphenol or 3-hydroxydibenzofuran at 110–130° in the presence of an equivalent of sodium hydroxide and a catalytic amount of potassium iodide. Yield: 95%, M.P.: 93°–94°, 83°–84° or 76°–77°.

The structural composition of further dyes is shown in the following Table I. They can be produced in accordance with the procedure of Example 1 and agree with the formula

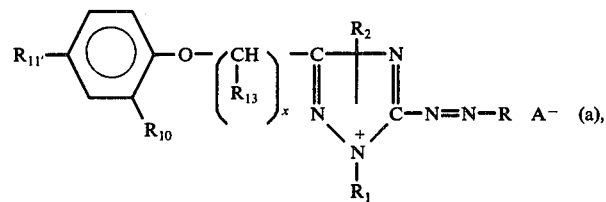

in which R, $R_1$, $R_2$, $R_{10}$, $R_{11'}$, $R_{13}$ and x have the significances as shown in the columns. A further column (I) indicates the dye shade on polyacrylonitrile.

The anion $A^-$ may be any one of those named in the foregoing description.

| Ex. | $R_1$ | $R_2$ | $R_{13}$ | x | R | $R_{10}$ | $R'_{11}$ | (I) |
|---|---|---|---|---|---|---|---|---|
| 3 | —CH₃ | —CH₃ | H | 1 | 3-methyl-9-ethylcarbazole | H | phenyl | brownish-red |
| 4 | —CH₃ | —CH₃ | H | 1 | " | phenyl | H | brownish-red |
| 5 | —CH₃ | —CH₃ | —CH₃ | 1 | " | " | H | brownish-red |
| 6 | —CH₃ | —CH₃ | —CH₃ | 1 | " | H | phenyl | brownish-red |
| 7 | —CH₃ | —CH₃ | H | 1 | 2-hydroxynaphthyl | H | " | orange |
| 8 | —CH₃ | —CH₃ | H | 1 | " | phenyl | H | orange |
| 9 | —CH₃ | —CH₃ | H | 1 | 2-hydroxybiphenyl | " | H | reddish-yellow |
| 10 | —CH₃ | —CH₃ | H | 1 | " | H | phenyl | reddish-yellow |

-continued

| Ex. | $R_1$ | $R_2$ | $R_{13}$ | x | R | $R_{10}$ | $R'_{11}$ | (I) |
|---|---|---|---|---|---|---|---|---|
| 11 | —$CH_3$ | —$CH_3$ | H | 1 | 3-methyl-5-hydroxy-1-phenylpyrazol-4-yl | H | " | greenish-yellow |
| 12 | —$CH_3$ | —$CH_3$ | H | 1 | " | phenyl | H | greenish-yellow |
| 13 | —$CH_3$ | —$CH_3$ | H | 1 | 3-cyano-4,5-dimethyl-6-hydroxy-1-methyl-2-oxo-1,2-dihydropyridin-yl | " | H | yellow |
| 14 | —$CH_3$ | —$CH_3$ | H | 1 | " | H | phenyl | yellow |
| 15 | —$CH_3$ | —$CH_3$ | H | 2 | " | H | " | " |
| 16 | —$CH_3$ | —$CH_3$ | H | 2 | " | phenyl | H | yellow |
| 17 | —$CH_3$ | —$CH_3$ | H | 1 | 3-cyano-4,5-dimethyl-6-hydroxy-2-imino-1,2-dihydropyridin-yl | " | H | yellow |
| 18 | —$CH_3$ | —$CH_3$ | H | 1 | " | H | phenyl | yellow |
| 19 | —$CH_3$ | —$CH_3$ | —$CH_3$ | 1 | 3-cyano-4,5-dimethyl-6-hydroxy-1-(3-methoxypropyl)-2-oxo-1,2-dihydropyridin-yl | H | " | yellow |
| 20 | —$CH_3$ | —$CH_3$ | —$CH_3$ | 1 | " | phenyl | H | yellow |
| 21 | —$CH_3$ | —$CH_3$ | H | 1 | 3-amino-4-methylnaphthyl | H | phenyl | scarlet |

-continued
| Ex. | R₁ | R₂ | R₁₃ | x | R | R₁₀ | R'₁₁ | (I) |
|---|---|---|---|---|---|---|---|---|
| 22 | —CH₃ | —CH₃ | H | 1 | " | 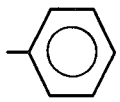 | H | scarlet |
| 23 | —CH₃ | —CH₃ | H | 1 | 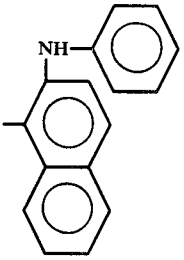 | " | H | bluish-red |
| 24 | —CH₃ | —CH₃ | H | 1 | " | H | 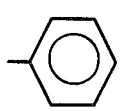 | bluish-red |
| 25 | —CH₃ | —CH₃ | H | 2 | " | H | 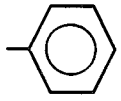 | bluish-red |
| 26 | —CH₃ | —CH₃ | H | 2 | " | 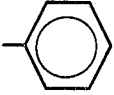 | H | bluish-red |
| 27 | —CH₃ | —CH₃ | H | 1 | 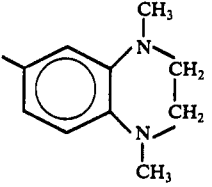 | " | H | reddish-violet |
| 28 | —CH₃ | —CH₃ | H | 1 | " | H | 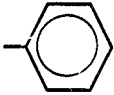 | reddish-violet |
| 29 | —CH₃ | —CH₃ | H | 1 | 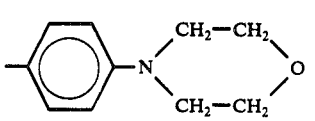 | H | " | bluish-red |
| 30 | —CH₃ | —CH₃ | H | 1 | " | 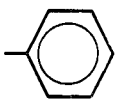 | H | bluish-red |
| 31 | —CH₃ | —CH₃ | H | 1 | 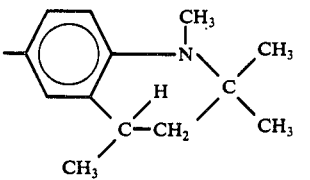 | H | 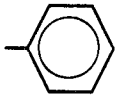 | reddish-violet |
| 32 | —CH₃ | —CH₃ | H | 1 | " | H | 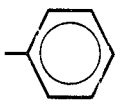 | reddish-violet |

-continued

| Ex. | $R_1$ | $R_2$ | $R_{13}$ | x | R | $R_{10}$ | $R'_{11}$ | (I) |
|---|---|---|---|---|---|---|---|---|
| 33 | —$CH_3$ | —$CH_3$ | —$CH_3$ | 1 | 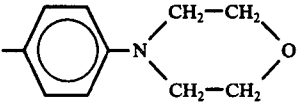 | H | 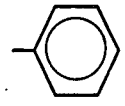 | bluish-red |
| 34 | —$CH_3$ | —$CH_3$ | —$CH_3$ | 1 | " | H | 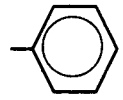 | bluish-red |
| 35 | —$CH_3$ | —$CH_3$ | H | 2 | 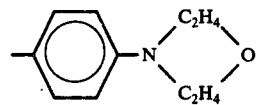 | H | 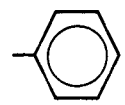 | bluish-red |
| 36 | —$CH_3$ | —$CH_3$ | H | 2 | " | H | 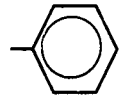 | bluish-red |
| 37 | —$CH_3$ | —$CH_3$ | H | 2 | 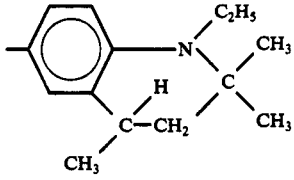 | H |  | reddish-violet |
| 38 | —$CH_3$ | —$CH_3$ | H | 2 | " | H | 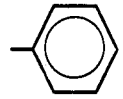 | reddish-violet |

The structural composition of further dyes is shown in the following Table II. The dyes can be produced in accordance with the procedure of Example I, and they correspond to the formula

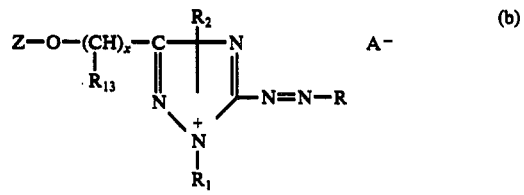

(b)

in which Z, R, $R_1$, $R_2$, $R_{13}$ and x have the significances as shown in the columns of the Table. In a further column I, the dye shade on polyacrylonitrile is shown.

The anion $A^-$ may be one of those named in the foregoing description.

| Ex. | $R_1$ | $R_2$ | $R_{13}$ | x | Z | R | (I) |
|---|---|---|---|---|---|---|---|
| 39 | —$CH_3$ | —$CH_3$ | H | 1 | 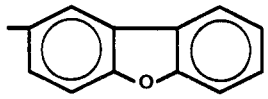 | 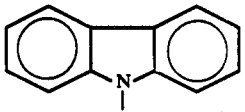 | brownish-red |
| 40 | " | " | —$CH_3$ | 1 | " | " | " |
| 41 | " | " | H | 2 | " | " | " |
| 42 | " | " | H | 1 | " | 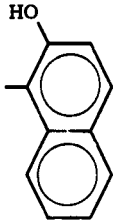 | orange |

-continued

| Ex. | R₁ | R₂ | R₁₃ | x | Z | R | (I) |
|---|---|---|---|---|---|---|---|
| 43 | " | " | H | 1 | " | [biphenyl with OH and CH₃] | " |
| 44 | " | " | H | 2 | " | " | greenish-yellow |
| 45 | " | " | H | 1 | " | [pyrazolone with CH₃, HO, N-phenyl] | " |
| 46 | " | " | H | 2 | " | " | " |
| 47 | " | " | H | 1 | " | [hydroxypyridone with CH₃, CN, HO] | yellow |
| 48 | " | " | —CH₃ | 1 | " | " | " |
| 49 | " | " | H | 2 | " | " | " |
| 50 | " | " | H | 1 | [dibenzofuran with CH₃] | " | " |
| 51 | " | " | H | 1 | [dibenzofuran with CH₃] | [methylnaphthylamine with NH₂] | scarlet |
| 52 | " | " | H | 2 | " | " | " |
| 53 | " | " | H | 1 | " | [methylnaphthyl-NH-phenyl] | brownish-red |
| 54 | " | " | H | 1 | " | [N,N'-dimethyl tetrahydroquinoxaline with CH₃] | reddish-violet |
| 55 | " | " | H | 1 | " | [aniline with isopropyl and N(tBu)(CH₃)] | " |
| 56 | " | " | —CH₃ | 1 | " | " | " |
| 57 | " | " | H | 2 | " | [aniline with isopropyl CH₂C(CH₃)₂ and N-C₂H₅] | " |
| 58 | " | " | H | 1 | " | [p-tolyl morpholine] | bluish-red |
| 59 | " | " | —CH₃ | 1 | " | " | " |
| 60 | " | " | H | 2 | " | " | " |

-continued

| Ex. | R₁ | R₂ | R₁₃ | x | Z | R | (I) |
|---|---|---|---|---|---|---|---|
| 61 | " | " | H | 1 | (dibenzofuran with CH₃) | | |
| 62 | " | " | H | 1 | (dibenzofuran with CH₃) | (2-methyl-3-methylindole, NH) | yellow |
| 63 | " | " | H | 1 | " | (2-phenyl-3-methylindole, NH) | reddish-yellow |
| 64 | " | " | —CH₃ | 1 | " | " | " |
| 65 | " | " | H | 2 | " | " | " |
| 66 | " | " | H | 1 | " | (2-phenyl-3-methyl-N-methylindole) | " |
| 67 | " | " | —CH₃ | 1 | " | " | " |
| 68 | " | " | H | 2 | " | " | " |
| 69 | " | " | H | 1 | " | (naphthyl-N(CH₃)(C₂H₅)) | bluish-red |
| 70 | " | " | H | 1 | " | (naphthyl-N(CH₃)₂) | " |
| 71 | " | " | H | 2 | " | " | " |
| 72 | " | " | H | 1 | " | (naphthyl-N(CH₃)(C₂H₄—COOC₄H₉)) | bluish-violet |
| 73 | " | " | —CH₃ | 2 | " | " | " |
| 74 | " | " | H | 1 | " | " | " |

The structural composition of further dyes is shown in Table III. They may be prepared in accordance with the procedure in Example 1, and correspond to the formula

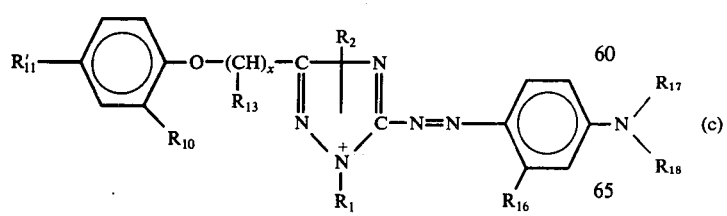

in which $R_1$, $R_2$, $R_{10}$, $R_{11'}$, $R_{13}$, $R_{16}$, $R_{17}$, $R_{18}$ and x have the significances as shown in the columns of the Table. A further column (I) indicates the dye-shade on polyacrylonitrile. The anion $A^\ominus$ may be any one of those named in the foregoing description.

| Ex. | R₁ | R₂ | R₁₃ | R₁₆ | X | R₁₀ | R'₁₁ | R₁₇ | R₁₈ | (I) |
|---|---|---|---|---|---|---|---|---|---|---|
| 75 | —CH₃ | —CH₃ | H | H | 1 | H | —Ph | —CH₃ | —CH₃ | bluish-red |
| 76 | " | " | H | H | 1 | —Ph | H | " | " | " |
| 77 | " | " | H | H | 1 | " | H | " | —CH₂—Ph | " |
| 78 | " | " | H | H | 1 | H | —Ph | " | " | " |
| 79 | " | " | H | H | 1 | H | " | " | —Ph | reddish-violet |
| 80 | " | " | H | H | 1 | —Ph | H | " | " | " |
| 81 | " | " | H | H | 1 | " | H | —C₂H₅ | —CH₂—Ph | bluish-red |
| 82 | " | " | H | H | 1 | H | —Ph | " | " | " |
| 83 | " | " | H | H | 1 | " | H | " | —C₂H₄OH | " |
| 84 | " | " | H | H | 1 | —Ph | H | " | " | " |
| 85 | " | " | H | H | 1 | " | H | " | —C₂H₄Cl | " |
| 86 | " | " | H | H | 1 | H | —Ph | " | " | " |
| 87 | " | " | H | H | 1 | " | H | " | —C₂H₄CN | " |
| 88 | " | " | H | H | 1 | H | —Ph | " | " | " |
| 89 | " | " | H | H | 1 | " | H | " | —C₂H₄—O—Ph | " |
| 90 | " | " | H | H | 1 | H | —Ph | " | " | " |
| 91 | " | " | H | H | 1 | H | " | " | —C₂H₄O—C(=O)—Ph | " |
| 92 | " | " | H | H | 1 | —Ph | H | " | " | " |
| 93 | " | " | H | H | 1 | H | —Ph | H | H | red |
| 94 | " | " | H | H | 1 | —Ph | H | H | H | " |
| 95 | " | " | H | —CH₃ | 1 | " | H | —CH₃ | —CH₃ | bluish-red |
| 96 | " | " | H | " | 1 | H | —Ph | " | " | " |
| 97 | " | " | H | " | 1 | " | H | —C₂H₅ | —C₂H₅ | " |
| 98 | " | " | H | " | 1 | H | —Ph | " | " | " |
| 99 | " | " | H | —OCH₃ | 1 | " | H | " | " | " |
| 100 | " | " | H | " | 1 | H | —Ph | " | " | " |
| 101 | " | " | H | Cl | 1 | H | " | " | " | red |
| 102 | " | " | H | " | 1 | H | —Ph | " | " | " |
| 103 | —C₂H₅ | —C₂H₅ | H | H | 1 | " | H | " | " | bluish-red |
| 104 | " | " | H | H | 1 | H | —Ph | " | " | " |
| 105 | " | " | H | H | 1 | H | " | —CH₃ | —CH₂—Ph | " |
| 106 | " | " | H | H | 1 | H | —Ph | " | " | " |
| 107 | " | " | H | H | 1 | " | H | —C₂H₅ | " | bluish-red rot |

-continued

| Ex. | $R_1$ | $R_2$ | $R_{13}$ | $R_{16}$ | X | $R_{10}$ | $R'_{11}$ | $R_{17}$ | $R_{18}$ | (I) |
|---|---|---|---|---|---|---|---|---|---|---|
| 108 | " | " | H | H | 1 | H | ⌬ | " | " | " |
| 109 | —C$_2$H$_4$CONH$_2$ | —C$_2$H$_4$CONH$_2$ | H | H | 1 | H | " | " | —C$_2$H$_5$ | " |
| 110 | " | " | H | H | 1 | ⌬ | H | " | " | " |
| 111 | —C$_2$H$_4$OH | —C$_2$H$_4$OH | H | H | 1 | H | ⌬ | " | " | rubine |
| 112 | " | " | H | H | 1 | ⌬ | H | " | " | " |
| 113 | —CH$_2$—CH(OH)—CH$_3$ | —CH$_2$—CH(OH)—CH$_3$ | H | H | 1 | " | H | " | " | " |
| 114 | " | " | H | H | 1 | H | ⌬ | " | " | " |
| 115 | —CH$_2$—⌬ | —CH$_3$ | H | H | 1 | H | " | " | " | bluish-red |
| 116 | " | " | H | H | 1 | ⌬ | H | " | " | " |
| 117 | —CH$_3$ | " | H | H | 1 | —CH$_3$ | ⌬ | " | " | " |
| 118 | " | " | H | H | 1 | —OCH$_3$ | " | " | " | " |
| 119 | " | " | H | H | 1 | —Cl | " | " | " | " |
| 120 | " | " | H | H | 1 | H | CH$_3$—⌬— | " | " | " |
| 121 | " | " | H | H | 1 | H | CH$_3$O—⌬— | " | " | " |
| 122 | " | " | H | H | 1 | H | NC—⌬— | " | " | " |
| 123 | " | " | H | H | 1 | H | CH$_3$—CO—⌬— | " | " | " |
| 124 | " | " | H | H | 1 | H | O$_2$N—⌬— | " | " | " |
| 125 | " | " | H | H | 1 | ⌬—CO— | —O—CH$_3$ | " | " | " |
| 126 | " | " | H | H | 1 | H | ⌬—SO$_2$—, —CH$_3$ | " | " | " |
| 127 | " | " | H | H | 1 | H | Cl—⌬— | " | " | " |
| 128 | " | " | H | H | 1 | H | CF$_3$—⌬— | " | " | " |
| 129 | " | " | —CH$_3$ | H | 1 | H | ⌬ | H | H | red |
| 130 | " | " | " | H | 1 | ⌬ | H | H | H | " |
| 131 | " | " | " | H | 1 | " | H | —CH$_3$ | —CH$_3$ | bluish-red |
| 132 | " | " | " | H | 1 | H | ⌬ | " | " | " |
| 133 | " | " | " | H | 1 | " | " | —C$_2$H$_5$ | —C$_2$H$_5$ | " |
| 134 | " | " | " | H | 1 | ⌬ | H | " | " | " |
| 135 | " | " | " | H | 1 | " | H | " | —CH$_2$—⌬ | " |
| 136 | " | " | " | H | 1 | H | ⌬ | " | " | " |
| 137 | " | " | " | " | 1 | H | " | —CH$_3$ | " | " |

-continued

| Ex. | R₁ | R₂ | R₁₃ | R₁₆ | X | R₁₀ | R'₁₁ | R₁₇ | R₁₈ | (I) |
|---|---|---|---|---|---|---|---|---|---|---|
| 138 | " | " | " | H | 1 | ⌬ | H | " | " | " |
| 139 | " | " | " | H | 1 | " | H | " | —CH₂⌬ | reddish-violet |
| 140 | " | " | " | H | 1 | H | ⌬ | " | ⌬ | " |
| 141 | " | " | " | —CH₃ | 1 | H | " | —C₂H₅ | —C₂H₅ | bluish-red |
| 142 | " | " | " | " | 1 | ⌬ | H | " | " | " |
| 143 | —C₂H₅ | —C₂H₅ | " | " | 1 | " | H | " | " | " |
| 144 | " | " | " | " | 1 | H | ⌬ | " | " | " |
| 145 | " | " | " | " | 1 | H | " | —CH₃ | —CH₂⌬ | " |
| 146 | " | " | " | " | 1 | ⌬ | H | " | " | " |
| 147 | " | " | H | H | 2 | H | " | H | H | scarlet |
| 148 | " | " | H | H | 2 | ⌬ | H | H | H | " |
| 149 | " | " | H | H | 2 | " | H | —CH₃ | —CH₃ | bluish-red |
| 150 | " | " | H | H | 2 | H | ⌬ | " | " | " |
| 151 | —CH₃ | —CH₃ | H | H | 2 | H | " | —C₂H₅ | —C₂H₅ | " |
| 152 | " | " | H | H | 2 | ⌬ | H | " | " | " |
| 153 | " | " | H | H | 2 | " | H | —CH₃ | —CH₂⌬ | " |
| 154 | " | " | H | H | 2 | H | ⌬ | " | " | " |
| 155 | " | " | H | H | 2 | " | H | —C₂H₅ | " | " |
| 156 | " | " | H | H | 2 | ⌬ | H | " | " | " |
| 157 | " | " | H | —CH₃ | 2 | " | H | " | —C₂H₅ | " |
| 158 | " | " | H | " | 2 | H | ⌬ | " | " | " |
| 159 | " | " | H | H | 2 | H | " | —CH₃ | ⌬ | rubine |
| 160 | " | " | H | H | 2 | ⌬ | H | " | " | " |
| 161 | —C₂H₅ | " | H | H | 2 | " | H | —C₂H₅ | —C₂H₅ | bluish-red |
| 162 | " | " | H | H | 2 | H | ⌬ | " | " | " |
| 163 | " | " | H | H | 2 | H | " | —CH₃ | —CH₂⌬ | " |
| 164 | " | " | H | H | 2 | ⌬ | H | " | " | " |
| 165 | —C₂H₄CONH₂ | —C₂H₄CONH₂ | H | H | 2 | H | " | —C₂H₅ | —C₂H₅ | " |
| 166 | " | " | H | H | 2 | ⌬ | H | " | " | " |
| 167 | —C₂H₄OH | —C₂H₄OH | H | H | 2 | " | H | " | " | " |
| 168 | " | " | H | H | 2 | H | ⌬ | " | " | " |
| 169 | —CH₂⌬ | —CH₃ | H | H | 2 | H | " | " | " | " |
| 170 | " | " | H | H | 2 | ⌬ | H | " | " | " |
| 171 | —CH₃ | " | H | H | 3 | " | H | " | " | " |

-continued

| Ex. | R₁ | R₂ | R₁₃ | R₁₆ | X | R₁₀ | R'₁₁ | R₁₇ | R₁₈ | (I) |
|---|---|---|---|---|---|---|---|---|---|---|
| 172 | " | " | H | H | 3 | H | –⟨phenyl⟩ | " | " | " |
| 173 | " | " | H | H | 3 | H | " | –CH₃ | –CH₂–⟨phenyl⟩ | " |
| 174 | " | " | H | H | 3 | –⟨phenyl⟩ | H | " | " | " |
| 175 | " | " | H | H | 3 | " | H | –C₂H₅ | " | " |
| 176 | " | " | H | H | 3 | H | –⟨phenyl⟩ | " | " | " |
| 177 | " | " | H | H | 3 | H | " | –CH₃ | –⟨phenyl⟩ | rubin |
| 178 | " | " | H | H | 3 | –⟨phenyl⟩ | H | " | " | " |
| 179 | –C₂H₅ | –C₂H₅ | H | H | 3 | " | H | –C₂H₅ | –C₂H₅ | bluish-red |
| 180 | " | " | H | H | 3 | H | –⟨phenyl⟩ | " | " | " |
| 181 | –C₂H₄CONH₂ | –C₂H₄CONH₂ | H | H | 3 | H | " | " | " | " |
| 182 | " | " | H | H | 3 | –⟨phenyl⟩ | H | " | " | " |
| 183 | –CH₃ | –CH₃ | H | H | 1 | H | –⟨phenyl⟩–OC(O)CH₃ | " | " | " |
| 184 | " | " | H | H | 1 | H | –⟨phenyl⟩–SO₂N(CH₃)₂ | " | " | " |
| 185 | " | " | H | H | 1 | H | –⟨phenyl⟩–NHCOCH₃ | " | " | " |
| 186 | " | " | H | H | 1 | H | –⟨phenyl⟩–SO₂NH–CH₃ | " | " | " |
| 187 | " | " | H | H | 1 | H | –⟨phenyl⟩–CONHCH₃ | " | " | " |
| 188 | ⟨C₆H₁₁⟩– | ⟨C₆H₁₁⟩– | H | H | 1 | H | –⟨phenyl⟩ | " | " | " |
| 189 | ⟨C₆H₄CH₃⟩– | –CH₃ | H | H | 1 | H | " | " | " | reddish-violet |
| 190 | –CH₃ | " | H | H | 1 | H | " | " | –C₂H₄–OCH₃ | bluish-red |
| 191 | " | " | H | H | 1 | –⟨phenyl⟩ | H | " | –C₂H₄COOCH₃ | " |
| 192 | " | " | H | H | 1 | " | H | " | –C₂H₄–OC(O)–N(CH₃)₂ | " |

The structural composition of further dyes is shown in the following Table IV. The dyes may be produced in accordance with the method of Example 1 and correspond to the formula

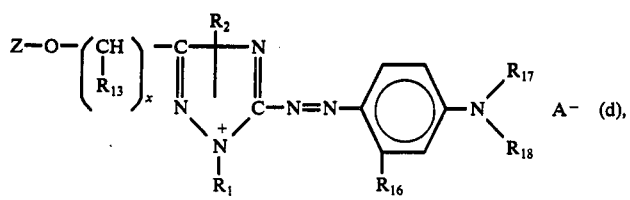

in which Z, x, R₁, R₂, R₁₃ and R₁₆ to R₁₈ have the significances as shown in the columns of the Table. A further column I, indicates the dye shade on polyacrylonitrile. The anion A⁻ may be any one of those named in the foregoing description.

Table IV

| Ex. | $R_1$ | $R_2$ | $R_{13}$ | $R_{16}$ | X | Z | $R_{17}$ | $R_{18}$ | I |
|---|---|---|---|---|---|---|---|---|---|
| 193 | —CH$_3$ | —CH$_3$ | H | H | 1 | dibenzofuran | —CH$_3$ | —CH$_3$ | bluish-red |
| 194 | " | " | H | H | 1 | dibenzofuran | —C$_2$H$_5$ | —C$_2$H$_5$ | " |
| 195 | " | " | —CH$_3$ | H | 1 | methyl-dibenzofuran | " | " | " |
| 196 | " | " | H | H | 2 | " | " | " | " |
| 197 | " | " | H | —CH$_3$ | 1 | " | " | " | " |
| 198 | " | " | H | —OCH$_3$ | 1 | " | " | " | " |
| 199 | " | " | H | Cl | 1 | " | " | " | " |
| 200 | " | " | H | H | 3 | " | " | " | " |
| 201 | " | " | H | H | 1 | " | —CH$_2$—C$_6$H$_5$ | —CH$_3$ | " |
| 202 | " | " | H | H | 1 | " | —C$_2$H$_4$OH | —C$_2$H$_5$ | strong bluish-red |
| 203 | " | " | H | H | 1 | " | —C$_2$H$_4$Cl | " | bluish-red |
| 204 | " | " | H | H | 1 | " | —C$_2$H$_4$CN | " | " |
| 205 | " | " | H | H | 1 | " | —C$_2$H$_4$COOC$_2$H$_5$ | " | " |
| 206 | " | " | H | H | 1 | " | —C$_6$H$_5$ | —CH$_3$ | reddish-violet |
| 207 | " | " | —CH$_3$ | H | 1 | " | —C$_2$H$_4$OC(=O)—N(CH$_3$)$_2$ | —C$_2$H$_5$ | bluish-red |
| 208 | " | " | " | H | 1 | " | —C$_2$H$_4$—O—CH$_3$ | " | " |
| 209 | " | " | " | H | 1 | " | —C$_2$H$_4$—O—C$_6$H$_5$ | " | " |
| 210 | " | " | H | H | 1 | " | —C$_2$H$_4$Cl | —C$_2$H$_4$Cl | red |

The structural composition of further dyes is shown in Table V. They can be produced in accordance with the procedure of Example 1 and correspond to the formula

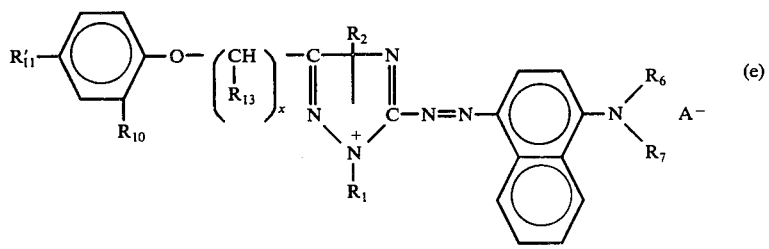

in which $R_1$, $R_2$, $R_6$, $R_7$, $R_{10}$, $R_{11'}$, $R_{13}$ and x have the significances as shown in the columns of the Table. A further column I, indicates the dye shade on polyacrylonitrile. The anion A$^-$ can be any one of those named in the foregoing description.

Table V

| Ex. | $R_1$ | $R_2$ | $R_{13}$ | X | $R_6$ | $R_7$ | $R_{10}$ | $R'_{11}$ | I |
|---|---|---|---|---|---|---|---|---|---|
| 211 | —CH$_3$ | —CH$_3$ | H | 1 | —CH$_3$ | —CH$_3$ | H | —C$_6$H$_5$ | bluish-violet |
| 212 | " | " | H | 1 | " | " | —C$_6$H$_5$ | H | " |
| 213 | " | " | H | 1 | " | —C$_2$H$_5$ | " | H | " |
| 214 | " | " | H | 1 | " | " | H | —C$_6$H$_5$ | " |
| 215 | " | " | H | 1 | " | —C$_2$H$_4$—COOC$_2$H$_5$ | " | H | " |
| 216 | " | " | H | 1 | " | " | H | —C$_6$H$_5$ | " |
| 217 | " | " | H | 1 | " | —C$_2$H$_4$—COOC$_4$H$_9$ | " | H | " |
| 218 | " | " | H | 1 | " | " | H | —C$_6$H$_5$ | " |
| 219 | " | " | —CH$_3$ | 1 | " | " | H | " | " |
| 220 | " | " | " | 1 | —CH$_3$ | —C$_2$H$_4$—COOC$_4$H$_9$ | —C$_6$H$_5$ | H | bluish-red |
| 221 | " | " | H | 2 | " | " | " | H | " |
| 222 | " | " | H | 2 | " | " | H | —C$_6$H$_5$ | " |

Table V-continued

| Ex. | $R_1$ | $R_2$ | $R_{13}$ | X | $R_6$ | $R_7$ | $R_{10}$ | $R'_{11}$ | I |
|---|---|---|---|---|---|---|---|---|---|
| 223 | " | " | H | 2 | " | —CH₃ | H | " | " |
| 224 | " | " | H | 2 | " | " |  | H | " |
| 225 | " | " | H | 2 | $R_6$ together with $R_7$ —C₂H₄O—C₂H₄— | " | / " | H | ". |
| 226 | " | " | H | 2 | " | " | H |  | " |
| 227 | " | " | H | 3 | " | —C₂H₄—COOC₄H₉ | H | " | " |
| 228 | " | " | H | 3 | " | " |  | H | " |

The structural composition of further dyes is given in the following Table VI. The dyes can be produced in accordance with the procedure of Example 1 and they correspond to the formula

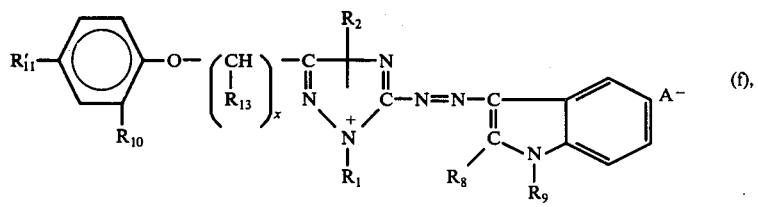

(f), in which $R_1$, $R_2$, $R_8$, $R_9$, $R_{10}$, $R_{11'}$, $R_{13}$ and x have the significances as shown in the columns of the Table. A further column I, indicates the dye shade on polyacrylonitrile. The anion A⁻ may be any one of those named in the foregoing description.

Table VI

| Ex. | $R_1$ | $R_2$ | $R_{13}$ | $R_9$ | x | $R_8$ | $R_{10}$ | $R'_{11}$ | I |
|---|---|---|---|---|---|---|---|---|---|
| 229 | —CH₃ | —CH₃ | H | H | 1 | —CH₃ | H |  | yellow |
| 230 | " | " | H | H | 1 | " |  | H | " |
| 231 | " | " | H | H | 1 | " | " | H | reddish-yellow |
| 232 | " | " | H | H | 1 | " | H |  | " |
| 233 | " | " | H | —CH₃ | 1 | " | H | " | " |
| 234 | " | " | H | " | 1 | " |  | H | " |
| 235 | " | " | H | " | 1 | —CH₃ | " | H | yellow |
| 236 | " | " | H | " | 1 | " | H |  | " |
| 237 | " | " | —CH₃ | H | 1 | " | H | " | " |
| 238 | " | " | " | H | 1 | " |  | H | " |
| 239 | " | " | " | H | 1 | " | " | H | reddish-yellow |
| 240 | " | " | " | H | 1 | " | H |  | " |
| 241 | " | " | " | —CH₃ | 1 | " | H | " | " |
| 242 | " | " | " | " | 1 | " |  | H | " |
| 243 | " | " | H | H | 2 | —CH₂— | " | H | " |
| 244 | " | " | H | H | 2 | " | H |  | " |
| 245 | " | " | H | " | 2 | " | H | " | " |
| 246 | " | " | H | " | 2 | " |  | H | " |

The structural composition of further dyes is shown in the following Table VII. They can be prepared in accordance with the procedure of Example 1 and they correspond to the formula

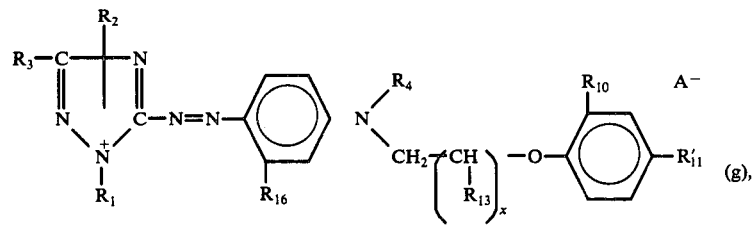

in which $R_1$, $R_2$, $R_3$, $R_4$, $R_{10}$, $R_{11'}$, $R_{13}$, $R_{16}$ and x have the significances as shown in the columns of the table. A further column I, indicates the dye shade on polyacrylonitrile. The anion $A^-$ may be any one of those named in the foregoing description.

Table VII

| Ex. | $R_1$ | $R_2$ | $R_3$ | $R_{13}$ | $R_{16}$ | $R_4$ | $R_{10}$ | x | $R'_{11}$ | I |
|---|---|---|---|---|---|---|---|---|---|---|
| 247 | —CH₃ | —CH₃ | H | H | H | —CH₃ | H | 1 | —⌬ | bluish-red |
| 248 | " | " | H | H | H | " | —⌬ | 1 | H | " |
| 249 | " | " | H | H | H | —C₂H₅ | " | 1 | H | " |
| 250 | " | " | H | H | H | " | —⌬ | 1 | H | " |
| 251 | " | " | H | H | H | —C₄H₉ | H | 1 | " | " |
| 252 | " | " | H | H | H | " | —⌬ | 1 | H | " |
| 253 | " | " | H | H | H | —C₂H₄CN | " | 1 | H | red |
| 254 | " | " | H | H | H | " | —⌬ | 1 | H | " |
| 255 | " | " | H | H | H | —CH₂—⌬ | H | 1 | " | " |
| 256 | " | " | H | H | H | " | —⌬ | 1 | H | bluish-red |
| 257 | " | " | H | H | —CH₃ | —CH₃ | " | 1 | H | " |
| 258 | " | " | H | H | " | " | —⌬ | 1 | H | " |
| 259 | " | " | H | H | " | —C₂H₅ | H | 1 | " | " |
| 260 | " | " | H | H | " | " | —⌬ | 1 | H | " |
| 261 | " | " | H | H | —OCH₃ | —CH₃ | " | 1 | H | " |
| 262 | " | " | H | H | " | " | —⌬ | 1 | H | " |
| 263 | " | " | H | H | —Cl | " | H | 1 | " | scarlet |
| 264 | " | " | H | H | " | " | —⌬ | 1 | H | " |
| 265 | " | " | H | —CH₃ | H | —CH₃ | H | 1 | —⌬ | bluish-red |
| 266 | " | " | H | " | H | " | —⌬ | 1 | H | " |
| 267 | " | " | H | " | H | —C₂H₅ | " | 1 | H | " |
| 268 | " | " | H | " | H | " | —⌬ | 1 | H | " |
| 269 | " | " | H | " | —CH₃ | —CH₃ | H | 1 | " | " |
| 270 | " | " | H | " | " | " | —⌬ | 1 | H | " |
| 271 | " | " | H | " | " | —C₂H₅ | " | 1 | H | " |
| 272 | " | " | H | " | " | " | —⌬ | 1 | H | " |
| 273 | " | " | H | —⌬ | H | —CH₃ | H | 1 | " | " |
| 274 | " | " | H | " | H | " | —⌬ | 1 | H | " |
| 275 | " | " | —CH₃ | H | H | —CH₃ | " | 1 | H | " |

Table VII-continued

| Ex. | R₁ | R₂ | R₃ | R₁₃ | R₁₆ | R₄ | R₁₀ | x | R'₁₁ | I |
|---|---|---|---|---|---|---|---|---|---|---|
| 276 | " | " | " | H | H | " | H | 1 | —C₆H₅ | " |
| 277 | " | " | " | H | H | —C₂H₅ | " | 1 | " | " |
| 278 | " | " | " | H | H | " | —C₆H₅ | 1 | H | " |
| 279 | " | " | " | H | —CH₃ | " | " | 1 | H | " |
| 280 | " | " | " | H | " | " | H | 1 | —C₆H₅ | " |
| 281 | " | " | " | —CH₃ | H | —CH₃ | " | 1 | " | " |
| 282 | " | " | " | " | H | " | —C₆H₅ | 1 | H | " |
| 283 | " | " | —C₆H₅ | H | H | " | H | 1 | —C₆H₅ | " |
| 284 | " | " | " | H | H | " | —C₆H₅ | 1 | H | " |
| 285 | " | " | " | —CH₃ | H | " | " | 1 | H | " |
| 286 | " | " | " | " | H | " | —C₆H₅ | 1 | —C₆H₅ | " |
| 287 | " | " | " | H | —CH₃ | —C₂H₅ | " | 1 | " | rubine |
| 288 | " | " | " | H | " | " | —C₆H₅ | 1 | H | " |
| 289 | " | " | H | H | H | " | H | 1 | —C₆H₄—CH₃ | bluish-red |
| 290 | " | " | H | H | H | " | H | 1 | —C₆H₄—OCH₃ | " |
| 291 | " | " | H | H | H | " | H | 1 | —C₆H₄—Cl | " |
| 292 | " | " | H | H | H | " | H | 1 | —C₆H₃Cl₂ | " |
| 293 | " | " | H | H | H | " | H | 1 | —C₆H₄—CN | " |
| 294 | " | " | H | H | H | " | H | 1 | —C₆H₄—NO₂ | " |
| 295 | " | " | H | H | H | " | —CH₃ | 1 | —C₆H₄—CH₃ | " |
| 296 | " | " | H | H | H | " | " | 2 | —C₆H₅ | " |
| 297 | " | " | H | H | H | " | —C₆H₅ | 2 | H | " |
| 298 | " | " | H | H | H | " | " | 3 | H | " |
| 299 | " | " | H | H | H | " | H | 3 | —C₆H₅ | " |
| 300 | —CH₂—C₆H₅ | " | H | H | H | " | H | 1 | —C₆H₅ | red |
| 301 | " | " | H | H | H | " | —C₆H₅ | 1 | H | " |
| 302 | —C₂H₅ | —C₂H₅ | H | H | H | —CH₃ | H | 1 | —C₆H₅ | bluish-red |
| 303 | " | " | H | H | H | " | —C₆H₅ | 1 | H | " |
| 304 | " | " | H | H | H | —C₂H₅ | " | 1 | H | " |
| 305 | " | " | H | H | H | " | H | 1 | —C₆H₅ | " |
| 306 | " | " | H | —CH₃ | H | —CH₃ | H | 1 | " | " |
| 307 | " | " | H | " | H | " | " | 1 | H | " |
| 308 | " | " | H | H | —CH₃ | —C₂H₅ | " | 1 | H | " |

Table VII-continued

| Ex. | R₁ | R₂ | R₃ | R₁₃ | R₁₆ | R₄ | R₁₀ | x | R'₁₁ | I |
|---|---|---|---|---|---|---|---|---|---|---|
| 309 | " | " | H | H | " | " | H | 1 | —⌬ | " |
| 310 | —C₂H₄CONH₂ | —C₂H₄CONH₂ | H | H | H | " | H | 1 | " | red |
| 311 | " | " | H | H | H | " | —⌬ | 1 | H | " |
| 312 | —CH₂—⌬ | " | H | H | H | —CH₃ | " | 1 | H | " |
| 313 | " | —C₂H₄CONH₂ | H | H | H | " | H | 1 | —⌬ | " |
| 314 | —C₂H₄CONH₂ | " | H | H | —CH₃ | —C₂H₅ | H | 1 | " | " |
| 315 | " | " | H | H | " | " | —⌬ | 1 | H | " |
| 316 | —CH₂—CH(OH)—CH₃ | —CH₂—CH(OH)—CH₃ | H | H | H | " | " | 1 | H | bluish-red |
| 317 | " | " | H | H | H | " | H | 1 | —⌬ | " |
| 318 | " | " | H | —CH₃ | H | —CH₃ | H | 1 | " | " |
| 319 | " | " | H | " | H | " | —⌬ | 1 | H | " |
| 320 | —CH₃ | —CH₃ | H | H | —C₂H₅ | H | 1 | —⌬—CF₃ | " |
| 321 | " | " | H | H | " | H | 1 | —⌬—C(O)CH₃ | " |
| 322 | " | " | H | H | " | H | 1 | —⌬—SO₂CH₃ | " |
| 323 | " | " | H | H | " | H | 1 | —⌬—OCOCH₃ | " |
| 324 | " | " | H | H | " | H | 1 | —⌬—COOCH₃ | " |
| 325 | " | " | H | H | " | H | 1 | —⌬—CONH—CH₃ | " |
| 326 | " | " | H | H | " | H | 1 | —⌬—SO₂NH—CH₃ | " |
| 327 | " | " | H | H | " | H | 1 | —⌬—SO₂N(CH₃)₂ | " |
| 328 | —CH₂—⌬ | —C₂H₄OH | H | H | " | " | 1 | —⌬ | " |
| 329 | " | " | H | H | " | —⌬ | 1 | " | " |

The structural composition of further dyes is shown in the following Table VIII. The dyes may be prepared in accordance with the procedure of Example 2 and correspond with the formula

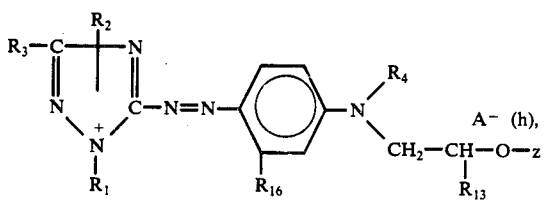

(h), in which Z, R₁, R₂, R₃, R₄, R₁₃ and R₁₆ have the significances as shown in the columns. A further column I, indicates the shade of dyeing on polyacrylonitrile.
The anion A⁻ may be any one of those named in the foregoing description.

Table VIII

| Ex. | $R_3$ | $R_1$ | $R_2$ | $R_{16}$ | $R_{13}$ | $R_4$ | Z | I |
|---|---|---|---|---|---|---|---|---|
| 330 | H | —CH₃ | —CH₃ | H | H | —CH₃ | 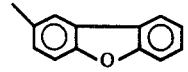 | bluish-red |
| 331 | H | " | " | H | H | " | 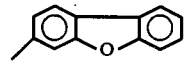 | " |
| 332 | H | " | " | H | —CH₃ | " | 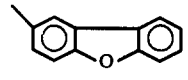 | " |
| 333 | H | " | " | H | " | " | 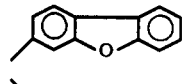 | " |
| 334 | H | " | " | —CH₃ | H | —C₂H₅ | 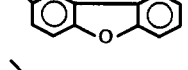 | " |
| 335 | H | " | " | " | —CH₃ | " | 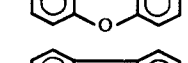 | " |
| 336 | H | " | " | H | H | —CH₂—⌬ | 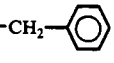 | " |
| 337 | H | " | " | H | H | —C₄H₉ | 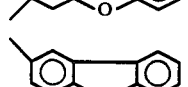 | " |
| 338 | H | " | " | —Cl | H | —C₂H₅ | 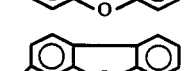 | scarlet |
| 339 | H | —C₂H₅ | —C₂H₅ | H | H | —C₂H₅ | 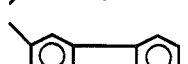 | bluish-red |
| 340 | H | " | " | H | —CH₃ | —CH₃ | 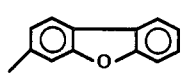 | " |
| 341 | H | " | " | —CH₃ | " | —C₂H₅ | 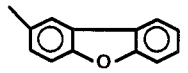 | " |
| 342 | H | " | " | H | H | —CH₂—⌬ | 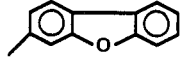 | red |
| 343 | H | —CH₃ | —CH₂—⌬ | H | H | —C₂H₅ | 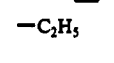 | " |
| 344 | H | —CH₃ | " | H | —CH₃ | —CH₃ | 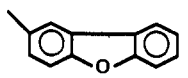 | " |
| 345 | —CH₃ | " | —CH₃ | H | H | —C₂H₅ | 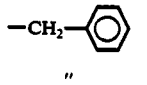 | bluish-red |
| 346 | " | " | " | —CH₃ | H | " | 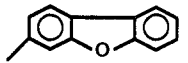 | " |
| 347 | ⌬— | " | " | H | H | " | 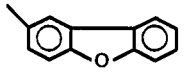 | " |
| 348 | " | " | " | H | —CH₃ | " | | " |
| 349 | " | " | " | —CH₃ | " | " | 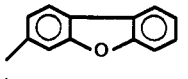 | " |
| 350 | " | " | " | " | H | " | 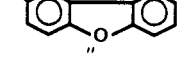 | " |
| 351 | " | —C₂H₅ | —C₂H₅ | H | H | " |  | " |
| 352 | H | —CH₃ | —CH₃ | H | H | " | 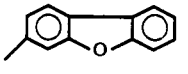 | " |

Table VIII-continued
| Ex. | R₃ | R₁ | R₂ | R₁₆ | R₁₃ | R₄ | Z | I |
|---|---|---|---|---|---|---|---|---|
| 353 | H | " | " | H | H | " | 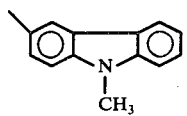 | " |
| 354 | H | " | " | H | H | " | 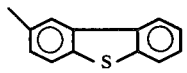 | " |
| 355 | H | " | " | H | H | " | 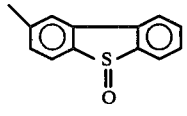 | " |
| 356 | H | " | " | H | H | " | 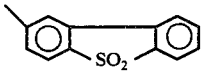 | " |
| 357 | H | " | " | H | H | " | 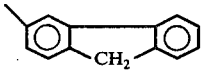 | " |
| 358 | H | " | " | H | H | " | 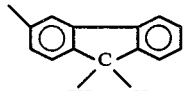 | " |
| 359 | H | " | " | H | H | " | 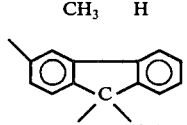 | " |
| 360 | H | " | " | H | H | " | 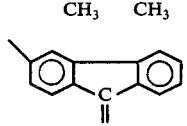 | " |
| 361 | H | " | " | H | H | " | 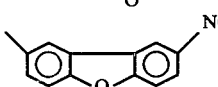 | " |
| 362 | H | " | " | H | H | " | 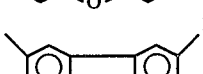 | " |
| 363 | H | " | " | H | H | " | 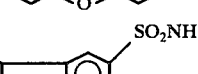 | " |
| 364 | H | " | " | H | H | " | 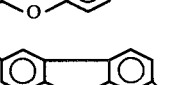 | " |
| 365 | H | " | " | H | H | " | 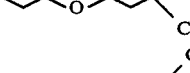 | " |
| 366 | H | " | " | H | H | " | 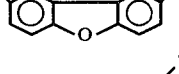 | " |
| 367 | H | " | " | H | H | " | 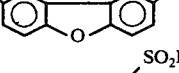 | " |
| 368 | H | " | " | H | H | " | 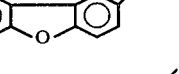 | " |
| 369 | H | " | " | H | H | " | 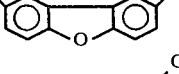 | " |
| 370 | H | " | " | H | H | " | 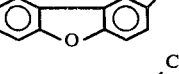 | " |

Table VIII-continued

| Ex. | R₃ | R₁ | R₂ | R₁₆ | R₁₃ | R₄ | Z | I |
|---|---|---|---|---|---|---|---|---|
| 371 | H | " | " | H | H | " | 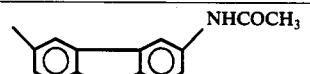 NHCOCH₃ | " |
| 372 | H | " | " | H | H | " | 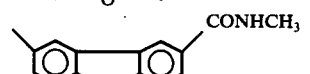 CONHCH₃ | " |
| 373 | H | —C₂H₅ | " | H | H | " | 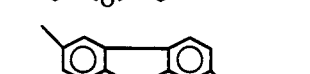 CH₃ | " |
| 374 | H | —CH₃ | " | H | H | " |  Cl, Cl | " |
| 375 | H | " | " | H | H | " | 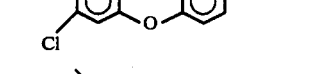 CH₃ | " |
| 376 | H | " | " | H | H | " | 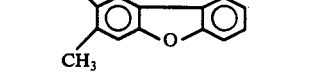 OCH₃, OCH₃ | " |

EXAMPLE 377

18 Parts of 2-amino-6-methoxybenzothiazole are dissolved in 100 parts of glacial acetic acid and 90 parts of sulphuric acid are added while cooling with ice so that the temperature does not exceed 35°–40°. 100 Parts of ice are subsequently added and a solution consisting of 7.3 parts of sodium nitrite and 25 parts of water is then added dropwise at −5° to 0°. The mixture is stirred for 1 hour with cooling and a solution consisting of 31.7 parts of the coupling component of the formula

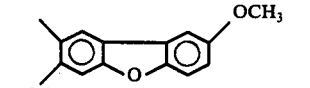

dissolved in 100 parts of glacial acetic acid and 50 parts of dimethylformamide, is added. The reaction mixture is stirred for 3 hours at room temperature and the pH is then adjusted to 3 with 170 parts of a 30% aqueous sodium hydroxide solution. The temperature is kept below 35° by cooling. The precipitated dye is filtered and well washed with water and dried at 50° in a vacuum. 25.5 Parts of the dried and ground dye are mixed while stirring with 200 parts of glacial acetic acid, 2.2 parts of magnesium oxide are added and the mixture is heated to 60°–70°. 14 Parts of dimethyl sulphate are added dropwise over the course of 15 minutes and the mixture is subsequently sitrred at 70°–75° for 3 hours. The reaction mixture is diluted with 2000 parts of water and the dye salted out by the addition of 15 parts of zinc chloride and 80 parts of sodium chloride. The dye is filtered with suction, washed with 100 parts of a 55% aqueous common salt solution and dried at 50° in a vacuum. 27.8 Parts of the dye of the formula

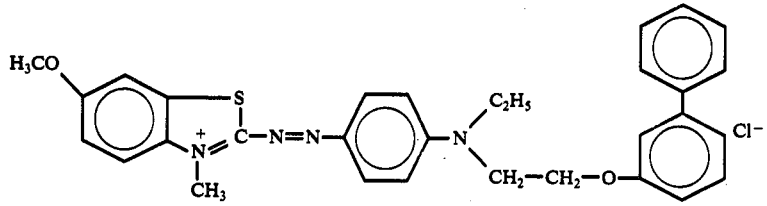

are obtained. Applied on polyacrylonitrile fibres and polyester fibres, modified by the introduction of acid groups, this dye gives fast blue dyeings. Replacing the above coupling component by 31.7 parts of the compound of the formula

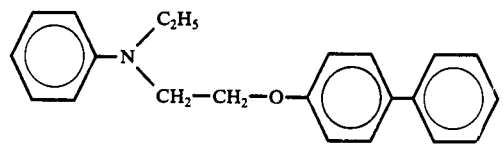

a dye of the formula

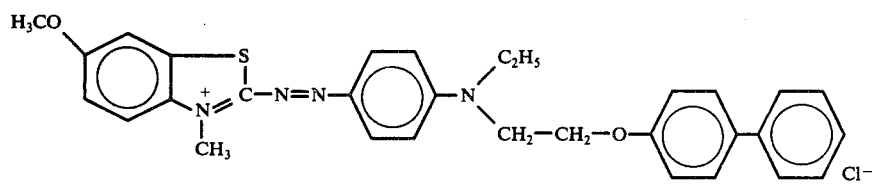

is obtained in accordance with the same process, which likewise on polyacrylonitrile and acid-modified polyester fibres gives fast blue dyeings.

In place of the above coupling component 33.1 parts of the compound of the formula is used, employing the same process, to yield the dye of the formula

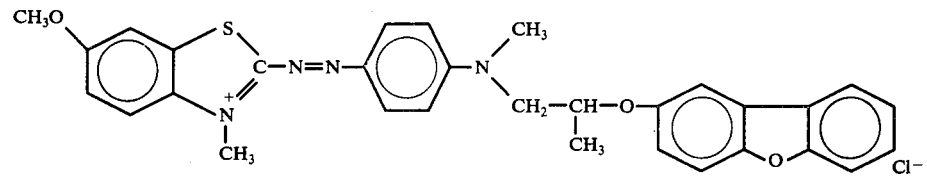

which likewise gives fast blue dyeings on polyacrylonitrile and acid-modified polyester fibres.

The structural composition of further dyes is shown in the following Table IX. They can be prepared in accordance with the process of Example 377 and correspond to the formula

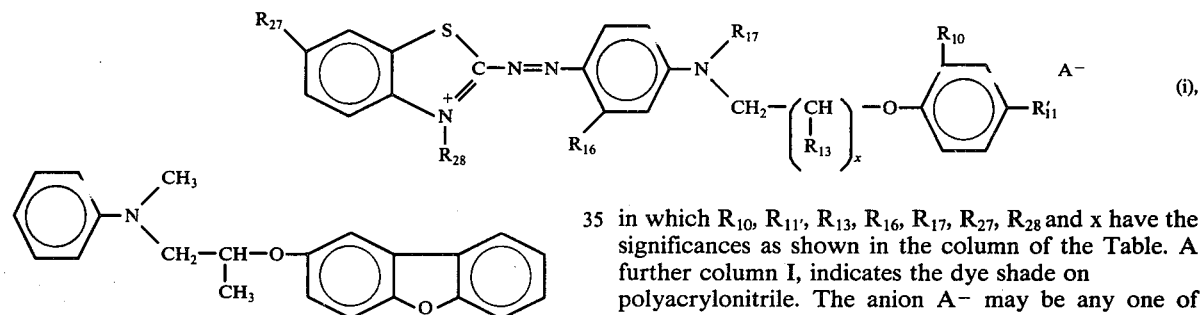

in which $R_{10}$, $R_{11'}$, $R_{13}$, $R_{16}$, $R_{17}$, $R_{27}$, $R_{28}$ and x have the significances as shown in the column of the Table. A further column I, indicates the dye shade on polyacrylonitrile. The anion $A^-$ may be any one of those named in the foregoing description.

Table IX

| Ex. | $R_{27}$ | $R_{28}$ | $R_{13}$ | $R_{16}$ | x | $R_{17}$ | $R_{10}$ | $R'_{11}$ | I |
|---|---|---|---|---|---|---|---|---|---|
| 378 | H | —CH₃ | H | H | 1 | —C₂H₅ | H | —⟨Ph⟩ | blue |
| 379 | H | " | H | H | 1 | " | —⟨Ph⟩ | H | " |
| 380 | H | " | H | —CH₃ | 1 | " | " | H | " |
| 381 | H | " | H | " | 1 | " | —⟨Ph⟩ | H | " |
| 382 | H | " | —CH₃ | H | 1 | —CH₃ | " | H | " |
| 383 | H | " | " | H | 1 | " | —⟨Ph⟩ | H | " |
| 384 | CH₃O— | " | H | H | 1 | " | " | H | greenish-blue |
| 385 | " | " | H | H | 1 | " | —⟨Ph⟩ | H | " |
| 386 | " | " | H | —CH₃ | 1 | " | " | H | " |
| 387 | " | " | H | " | 1 | C₂H₅ | —⟨Ph⟩ | H | blue |
| 388 | " | " | H | " | 1 | " | " | H | " |
| 389 | " | " | —CH₃ | H | 1 | —CH₃ | " | H | greenish-blue |
| 390 | " | " | " | H | 1 | " | —⟨Ph⟩ | H | " |
| 391 | " | —C₂H₄CONH₂ | H | H | 1 | —C₂H₅ | " | H | " |
| 392 | " | " | H | H | 1 | " | —⟨Ph⟩ | H | " |
| 393 | " | " | —CH₃ | H | 1 | —CH₃ | " | H | " |

Table IX-continued

| | | | | | | | | |
|---|---|---|---|---|---|---|---|---|
| 394 | " | " | " | H | 1 | " |  | H | " |
| 395 |  | —CH₃ | " | H | 1 | " | " | H | " |
| 396 |  | " | " | H | 1 | " | " | H | " |
| 397 |  | " | " | H | 1 | " | " | H | blue |
| 398 |  | " | " | H | 1 | " | " | H | " |
| 399 | Br— | " | " | H | 1 | " | " | H | " |
| 400 |  | " | " | H | 1 | " | " | H | " |
| 401 | CH₃O— | " | " | H | 1 | —C₂H₄OH | " | H | greenish-blue |
| 402 | " | " | " | H | 1 | " | H |  | " |
| 403 | " | " | " | H | 1 | —C₂H₄CN | H | " | blue |
| 404 | " | " | " | H | 1 | —C₂H₄Cl |  | H | " |

| Ex. | | | Dye-shade on polyacrylonitrile |
|---|---|---|---|
| 405 | 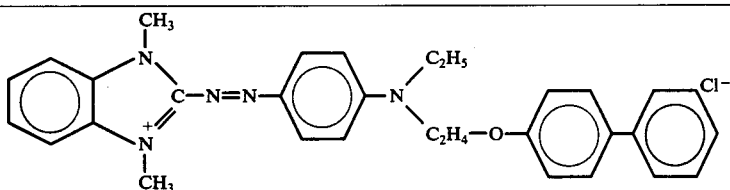 | | yellowish-red |
| 406 | 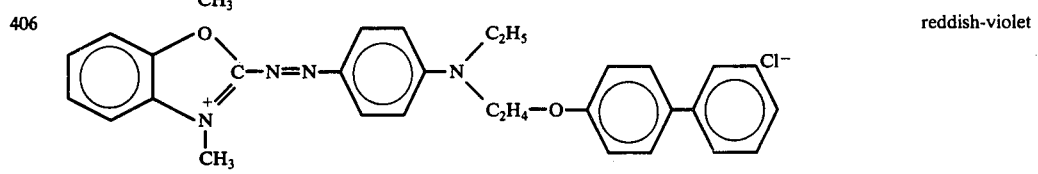 | | reddish-violet |

The structural composition of further dyes is shown in the following Table X. They can be produced in accordance with the methods of the foregoing Examples and correspond to the formula in which Z, $R_{13}$, $R_{16}$, $R_{17}$, $R_{27}$, $R_{28}$ and x have the significances as shown in the columns. A further column I, indicates the dye-shade on polyacrylonitrile. The anion $A^-$ may be any one of those named in the foregoing description.

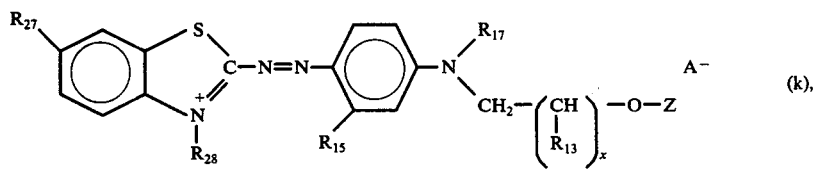

(k),

Table X

| Ex. | $R_{27}$ | x | $R_{28}$ | $R_{16}$ | $R_{13}$ | $R_{17}$ | Z | I |
|---|---|---|---|---|---|---|---|---|
| 407 | H | 1 | —CH₃ | H | H | —C₂H₅ |  | blue |
| 408 | H | 1 | " | —CH₃ | H | " |  | " |
| 409 | CH₃O— | 1 | " | H | H | " |  | greenish-blue |
| 410 | " | 1 | " | H | H | " |  | " |

Table X-continued

| Ex. | R27 | x | R28 | R16 | R13 | R17 | Z | I |
|---|---|---|---|---|---|---|---|---|
| 411 | " | 1 | " | H | H | —CH₃ | (dibenzofuran) | " |
| 412 | " | 1 | —C₂H₅ | H | H | —C₂H₅ | (dibenzofuran) | " |
| 413 | " | 1 | " | H | H | " | (methyl-dibenzofuran) | " |
| 414 | " | 1 | —C₂H₄CONH₂ | H | H | " | " | " |
| 415 | " | 2 | —CH₃ | —CH₃ | H | " | " | blue |
| 416 | " | 2 | " | H | —CH₃ | " | " | " |
| 417 | " | 1 | " | H | H | —C₄H₉ | (methyl-dibenzofuran) | " |
| 418 | " | 1 | " | CH₃O— | H | —C₂H₅ | " | reddish-blue |
| 419 | (C₆H₅—CO—NH—) | 1 | " | H | —CH₃ | —CH₃ | " | greenish-blue |
| 420 | " | 1 | " | H | H | —C₂H₅ | " | " |
| 421 | (C₆H₅—O—) | 1 | " | H | H | " | " | " |
| 422 | " | 1 | " | H | —CH₃ | —CH₃ | " | " |
| 423 | (C₆H₅—CO—) | 1 | " | H | H | —C₂H₅ | " | " |
| 424 | (C₆H₅—SO₂—) | 1 | " | H | H | " | (methyl-dibenzofuran) | " |
| 425 | (C₆H₅—) | 1 | " | H | H | " | " | " |
| 426 | CH₃O— | 1 | " | H | —C₂H₅ | H | (N-ethyl-methyl-carbazole) | " |
| 427 | " | 1 | " | —Cl | H | —C₂H₅ | (methyl-dibenzofuran) | reddish-blue |
| 428 | —Cl | 1 | " | H | H | " | " | greenish-blue |

The structural composition of further dyes is shown in the following Table XI. They can be prepared in accordance with the procedure of the foregoing Examples and correspond to the formula in which $R_1$, $R_4$, $R_{10}$, $R_{11}'$, $R_{31}$ and $R_{16}$ have the significances as shown in columns. A further column I, indicates the dye-shade on polyacrylonitrile. The anion $A^-$ may be any one of those named in the foregoing description.

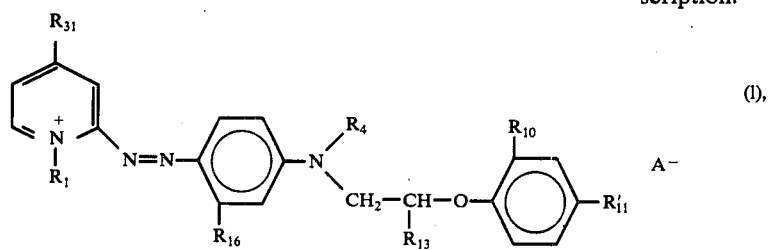

(I),

Table XI

| Ex. | R₁ | R₁₃ | R₁₆ | R₃₁ | R₄ | R₁₀ | R'₁₁ | I |
|---|---|---|---|---|---|---|---|---|
| 429 | —CH₃ | H | H | H | —CH₃ | H | —C₆H₅ | reddish-violet |
| 430 | " | H | H | H | " | —C₆H₅ | H | " |
| 431 | " | H | H | H | —C₂H₅ | " | H | " |

Table XI-continued

| 432 | " | H | H | H | " | H | ⌬ | " |
|---|---|---|---|---|---|---|---|---|
| 433 | " | H | —CH₃ | H | " | H | " | violet |
| 434 | " | H | " | H | " | ⌬ | H | " |
| 435 | " | —CH₃ | H | H | —CH₃ | " | H | reddish-violet |
| 436 | " | " | H | H | " | ⌬ | H | " |
| 437 | —C₂H₅ | H | H | H | —C₂H₅ | " | " | " |
| 438 | " | H | H | H | " | ⌬ | H | " |
| 439 | —OCH₃ | H | H | H | " | " | H | " |
| 440 | " | H | H | H | " | H | ⌬ | " |
| 441 | " | —CH₃ | H | H | —CH₃ | " | " | " |
| 442 | " | " | H | H | " | ⌬ | H | " |
| 443 | " | H | H | —CH₃ | —C₂H₅ | " | H | " |
| 444 | " | H | H | —NO₂ | " | " | H | violet |
| 445 | " | H | H | —CN | " | " | H | " |
| 446 | " | H | H | —Cl | " | " | H | reddish-violet |

| Ex. | | Dye-shade on poly-acrylonitrile |
|---|---|---|
| 447 | 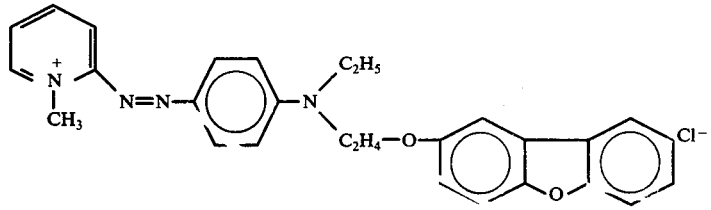 | reddish violet |
| 448 | 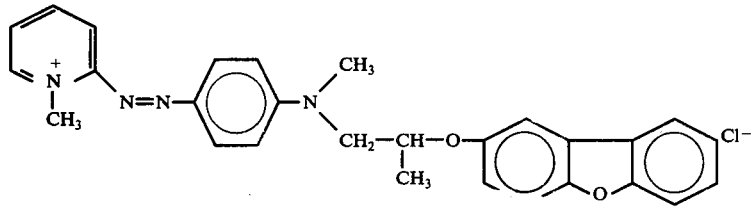 | " |
| 449 | 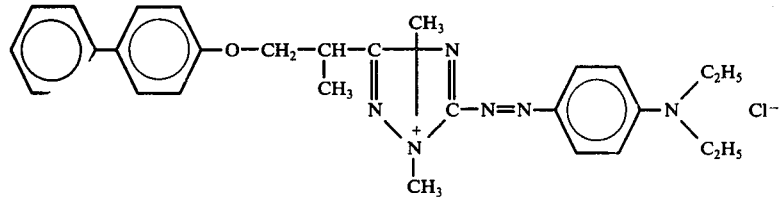 | bluish-red |
| 450 | 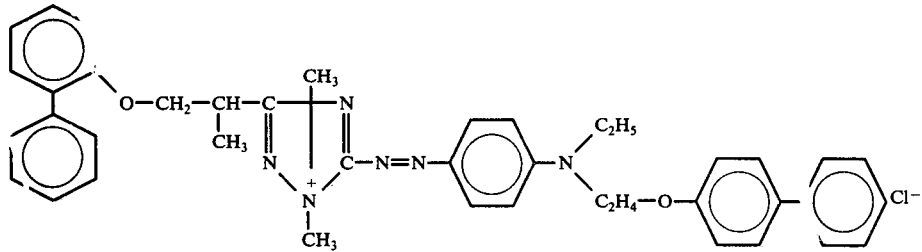 | " |

EXAMPLE 451

22 Parts of dimethyl sulphate are added at 10°-15° to a mixture consisting of 20.5 parts of 5-chloro-2,3,3-trimethylindolenine, 16.8 parts of sodium bicarbonate, 15 parts of water and 5 parts of ice. The mixture is subsequently heated to 60°, kept at this temperature for 30 minutes and then poured on 170 parts of brine. The organic phase is separated and diluted with 25 parts of glacial acetic acid. 33 Parts of 4-(N-ethyl-N-para-diphenoxyethyl)-amino-2-methylbenzaldehyde are added and the solution is heated to 85°-90°. The warm solution is added dropwise to 125 parts of brine, and the dye is filtered and washed with 40 parts of a 55% sodium chloride solution. After drying, 44.2 parts of the dye of the formula

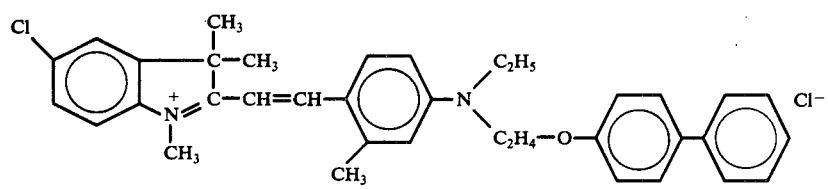

are obtained. Applied to polyacrylonitrile fibres or polyester fibres, modified by the introduction of acid groups, this dye gives bright bluish pink red dyeings. Replacing the above aldehyde component by 33 parts of 4-(N-ethyl-N-o-diphenoxyethyl)-amino-2-methylbenzaldehyde, a dye of the formula

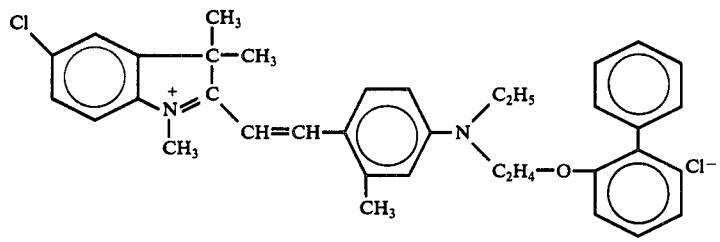

is obtained in accordance with the same process. This dye gives pink red dyeings on the above-mentioned substrates.

The structural composition of further dyes is shown in the following Table XII. They can be produced in accordance with the procedure of Example 451 and agree with the formula

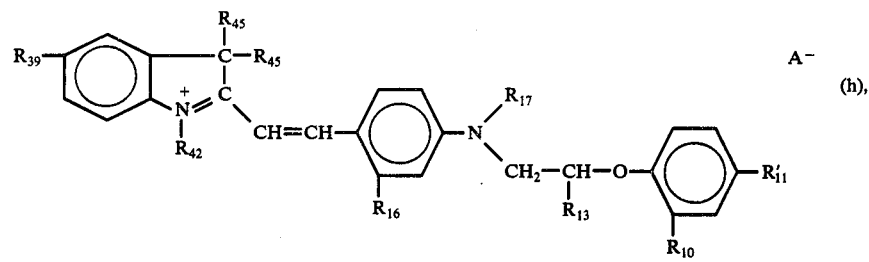

wherein $R_{10}$, $R_{11}'$, $R_{13}$, $R_{16}$, $R_{17}$, $R_{39}$, $R_{42}$, and $R_{45}$ have the significances given in the columns.

A further column I, indicates the shade of dyeing on polyacrylonitrile. The anion $A^-$ may be any one of these named in the foregoing description.

Table XII

| Ex. | $R_{42}$ | $R_{45}$ | $R_{16}$ | $R_{13}$ | $R_{39}$ | $R_{17}$ | $R_{10}$ | $R_{11}'$ | (I) |
|---|---|---|---|---|---|---|---|---|---|
| 453 | —CH₃ | —CH₃ | H | H | H | —CH₃ | H | –⟨O⟩ | bluish-red |
| 454 | " | " | H | H | H | " | –⟨O⟩ | H | " |
| 455 | " | " | H | H | H | —C₂H₅ | " | H | " |
| 456 | " | " | H | H | H | " | " | H | " |
| 457 | " | " | H | H | H | —C₂H₄CN | H | " | " |
| 458 | " | " | H | H | H | " | –⟨O⟩ | H | " |
| 459 | " | " | —CH₃ | H | H | " | " | H | " |
| 460 | " | " | " | H | H | " | " | H | " |
| 461 | " | " | " | H | H | —C₂H₅ | " | H | " |
| 462 | " | " | " | H | H | " | –⟨O⟩ | H | " |
| 463 | " | " | H | H | —Cl | " | " | H | " |
| 464 | " | " | H | H | " | " | " | H | " |
| 465 | " | " | H | H | " | —CH₃ | " | H | " |
| 466 | " | " | H | H | " | " | –⟨O⟩ | H | " |
| 467 | " | " | H | H | " | —C₂H₄CN | " | H | " |

Table XII-continued
| | | | | | | | | | |
|---|---|---|---|---|---|---|---|---|---|
| 468 | " | " | H | H | " | " | H |  | " |
| 469 | " | " | —CH₃ | H | " | " | H | " | " |
| 470 | " | " | " | H | " | " |  | H | |
| 471 | " | " | H | —CH₃ | " | —CH₃ | H |  | " |
| 472 | " | " | H | " | " | " |  | H | " |
| 473 | —CH₂—CH(CH₃)OH | " | H | H | " | —C₂H₅ | " | H | " |
| 474 | " | " | H | H | " | " | H |  | " |
| 475 | " | " | H | H | H | " | H | " | " |
| 476 | " | " | H | H | " | " |  | H | " |
| 477 | —CH₃ | " | H | H | —CH₃ | " | " | H | " |
| 478 | " | " | H | H | —OCH₃ | " | " | H | " |
| 479 | " | " | H | H |  | " | " | H | " |
| 480 | " | " | H | H |  | " | " | H | " |
| 481 | " | " | H | H |  | " | " | H | " |
| 482 | " | " | H | H | —CN | " | " | H | reddish-violet |
| 483 | " | " | H | H | —NO₂ | " | H |  | " |
| 484 | " | " | H | H |  | " | H | " | " |
| 485 | " | " | H | H |  | " | H | " | " |
| 486 | " | " | H | H |  | " | H | " | " |
| 487 | " | " | H | H | —SO₂N(CH₃)₂ | " | H | " | " |
| 488 | " | " | H | H | —CF₃ | " | H | " | " |
| Ex. | | Dye-shade on polyacrylonitrile |
|---|---|---|
| 489 | 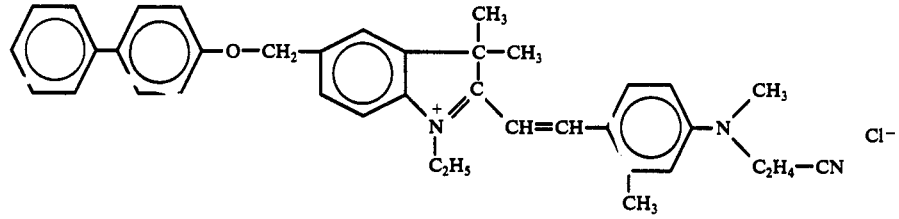 | bluish-red |
| 490 | 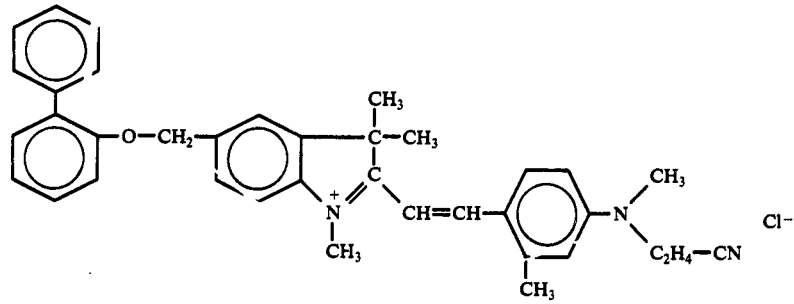 | " |

Table XII-continued

| | | |
|---|---|---|
| 491 |  | " |
| 492 | 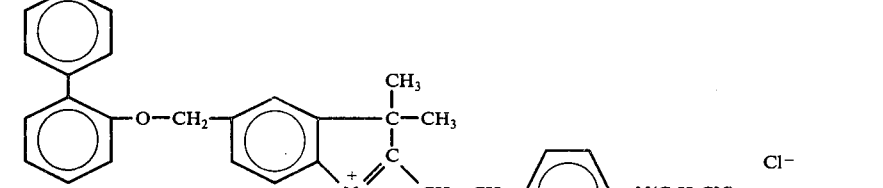 | scarlet |
| 493 | 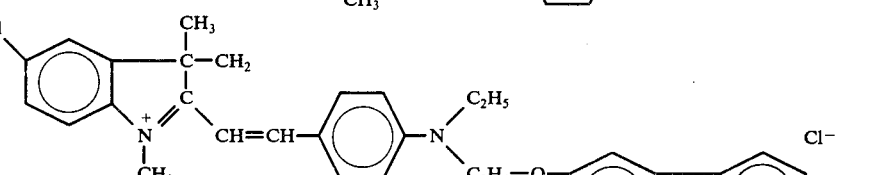 | pinkish-red |
| 494 | 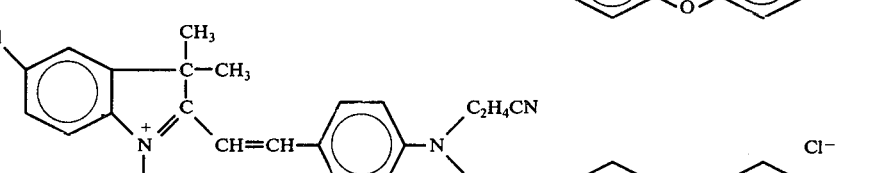 | " |
| 495 | 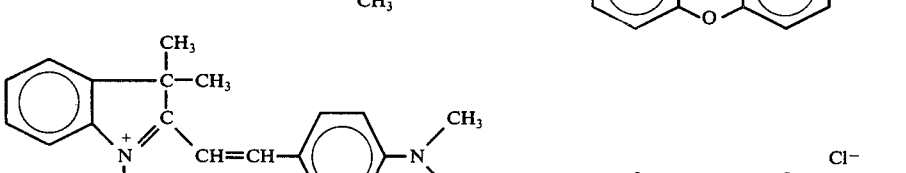 | " |

EXAMPLE 496

27.5 Parts of 4-p-diphenoxymethylaniline are diazotized in the presence of 25 parts of 36% hydrochloric acid in 300 parts of water at 0°-3° C with 21 parts of 4/normal nitrite solution. The excess nitrite is decomposed after 30 minutes by the addition of amidosulphonic acid and the resulting diazonium solution clear filtered. 17.7 Parts of 1,3,3-trimethyl-2-methylen-2,3-dihydroindole are added dropwise at 3°-5° and then 150 cc of a 20% sodium acetate solution are added while cooling simultaneously in the course of 2 hours. The reaction mixture is heated to 10°-15°, 20 parts of 30% sodium hydroxide solution are added and the coupling product is stirred for one hour. The red dye (azo base) is filtered with suction, washed with water and dried at 50°-60° at reduced pressure.

The methylation is effected by dissolving 36 parts of the azo base in 220 parts of chlorobenzene by the addition of 3.5 parts of triisopropanolamine. 40 Parts of the chlorobenzene are distilled off at 80°-85° under reduced pressure and 11.9 parts of dimethyl sulphate are subsequently added dropwise. The mixture is stirred at this temperature until the methylation is complete in accordance with thin layer chromatography. The mixture is cooled and the dye crystallizes, is suction filtered and washed with chlorobenzene. The dye agrees with the formula

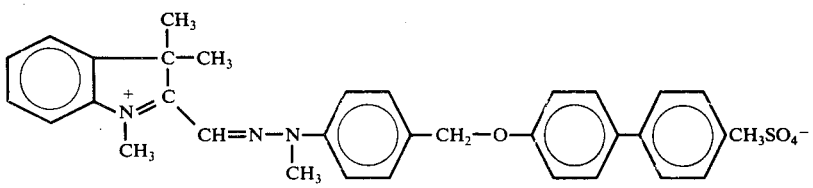

and dyes polyacrylonitrile fibres and polyester of polyamide fibres, modified by the introduction of acid groups, in golden-yellow shades. Replacing the above diazo component by 27.5 parts of 4-o-diphenoxymethylaniline, the dye of the formula The structural composition of further dyes is shown in the following Table XIII. They can be produced in accordance with the procedure of Example 496 and agree with the formula

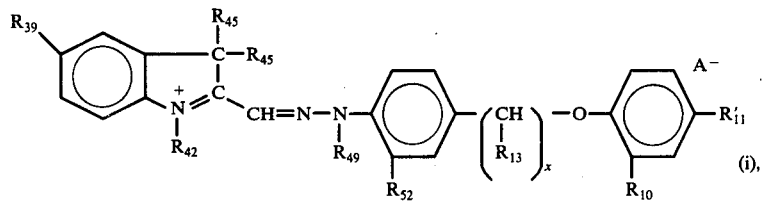

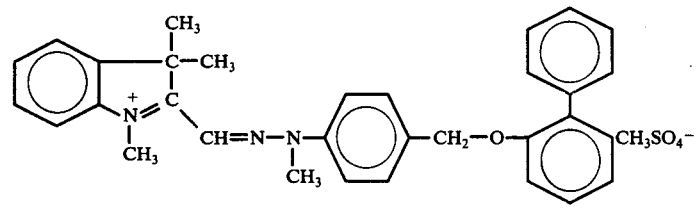

is obtained in accordance with the same process. Applied on polyacrylonitrile fibres and polyester or polyamide fibres, modified by the introduction of acid groups, this dye gives golden-yellow dyeings.

wherein $R_{10}$, $R_{11}'$, $R_{13}$, $R_{39}$, $R_{42}$, $R_{45}$, $R_{52}$ and x have the significances given in the columns.

A further column I indicates the shade of dyeing on polyacrylonitrile. The anion $A^-$ may be any one of these named in the foregoing description.

Table XIII

| Ex. | $R_{39}$ | $R_{42}$ | $R_{45}$ | $R_{49}$ | $R_{13}$ | $R_{52}$ | $R_{10}$ | x | $R_{11}'$ | I |
|---|---|---|---|---|---|---|---|---|---|---|
| 498 | H | —CH₃ | —CH₃ | —CH₃ | H | H | H | 2 | —C₆H₅ | reddish-yellow |
| 499 | H | " | " | " | H | H | —C₆H₅ | 2 | H | " |
| 500 | H | " | " | " | H | —CH₃ | " | 1 | H | " |
| 501 | H | " | " | " | H | " | H | 1 | —C₆H₅ | " |
| 502 | H | " | " | " | H | —OCH₃ | H | 1 | " | yellowish-orange |
| 503 | H | " | " | " | H | " | —C₆H₅ | 1 | H | " |
| 504 | —Cl | " | " | " | H | H | " | 1 | H | reddish-yellow |
| 505 | " | " | " | " | H | H | H | 1 | —C₆H₅ | " |
| 506 | " | " | " | " | H | H | H | 2 | " | " |
| 507 | " | " | " | " | H | H | —C₆H₅ | 2 | H | " |
| 508 | " | " | " | " | —CH₃ | H | " | 2 | H | " |
| 509 | " | " | " | " | " | H | H | 2 | —C₆H₅ | " |
| 510 | (CH₃)₂N—SO₂— | " | " | " | " | H | H | 1 | " | orange |
| 511 | " | " | " | " | " | H | —C₆H₅ | 1 | H | " |
| 512 | CH₃—O—C(=O)— | " | " | " | " | H | " | 1 | H | " |
| 513 | " | " | " | " | " | H | H | 1 | —C₆H₅ | " |
| 514 | —CH₂—CH(CH₃)OH | " | " | " | " | H | H | 1 | " | reddish-yellow |

Table XIII-continued

| Ex. | | Dye-shade on polyacrylonitrile |
|---|---|---|
| 516 | | golden yellow |
| 517 | | " |
| 518 | | " |
| 519 | | golden yellow |
| 520 | | " |

Example 521

20.1 parts of 1,3,3-trimethyl-2-methylene-2,3-dihydroindolaldehyde and 27.5 parts of 4-o-diphenoxymethylaniline are added to 100 parts of glacial acetic acid and 20 parts of water. The mixture is stirred at 40°–50° for 4 hours, is diluted with 500 parts of water and the dye is salted out with sodium chloride. The precipitated dye is suction filtered and washed with 200 parts of 5% common salt solution. After drying, 41.2 parts of the dye of the formula

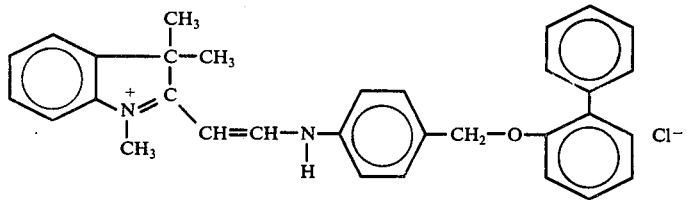

are obtained. Applied on polyacrylonitrile fibres and polyester and polyamide fibres, modified by the introduction of acid groups, this dye gives greenish yellow dyeings. Replacing the above amine by 4-(3'-dibenzofuranoxy)-methylaniline, a dye of the formula

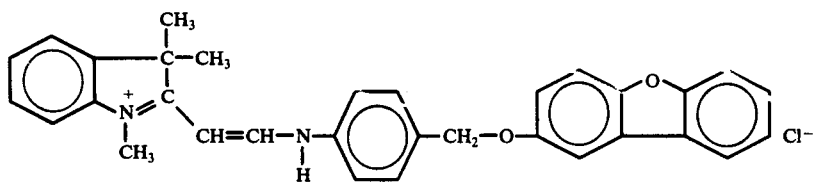

is obtained according to the same process. Applied on polyacrylonitrile fibres and polyester or polyamide fibres, modified by the introduction of acid groups, this dye gives greenish yellow dyeings.

The structural composition of further dyes which can be prepared according to the procedure of Example 521 is shown in the following Table XIV. They correspond to the formula

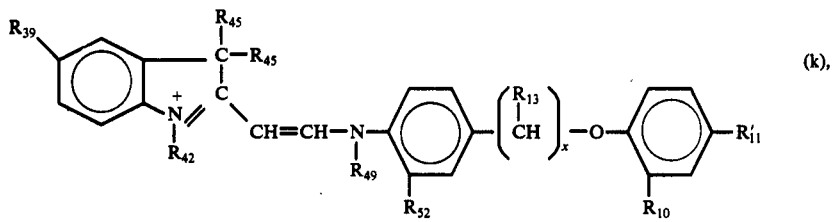

in which $R_{10}$, $R_{11}'$, $R_{13}$, $R_{39}$, $R_{42}$, $R_{42}$, $R_{45}$, $R_{49}$, $R_{52}$ and $x$ have the significances as shown in the columns. A further column I indicates the dye shade on polyacrylonitrile. The anion $A^-$ may be any one of those named in the foregoing description.

Table XIV

| Ex. | $R_{42}$ | $R_{45}$ | $R_{49}$ | $R_{13}$ | X | $R_{39}$ | $R_{52}$ | $R_{10}$ | $R_{11}'$ | I |
|---|---|---|---|---|---|---|---|---|---|---|
| 523 | —CH₃ | —CH₃ | H | —CH₃ | 1 | H | H | H | –⌬ | greenish-yellow |
| 524 | " | " | H | " | 1 | H | H | –⌬ | H | " |
| 525 | " | " | —CH₃ | H | 1 | H | H | " | H | " |
| 526 | " | " | " | H | 1 | H | H | H | –⌬ | " |
| 527 | " | " | H | H | 1 | H | —OCH₃ | H | " | yellow |
| 528 | " | " | H | H | 1 | H | " | –⌬ | H | " |
| 529 | " | " | H | H | 2 | H | H | " | H | greenish-yellow |
| 530 | " | " | H | H | 2 | H | H | H | –⌬ | " |
| 531 | " | " | H | —CH₃ | 2 | H | H | " | H | " |
| 532 | " | " | H | " | 2 | H | H | –⌬ | H | " |
| 533 | " | " | —CH₃ | H | 1 | O₂N— | H | " | H | " |
| 534 | " | " | " | H | 1 | " | H | –⌬ | H | " |
| 535 | " | " | H | H | 1 | H | —CH₃ | " | H | " |
| 536 | " | " | H | H | 1 | H | " | –⌬ | H | " |
| 537 | " | " | —CH₃ | H | 1 | —Cl | H | " | H | " |
| 538 | " | " | " | H | 1 | " | H | –⌬ | H | " |

| Ex. | Dye-shade on polyacrylonitrile |
|---|---|
| 539 | greenish-yellow |

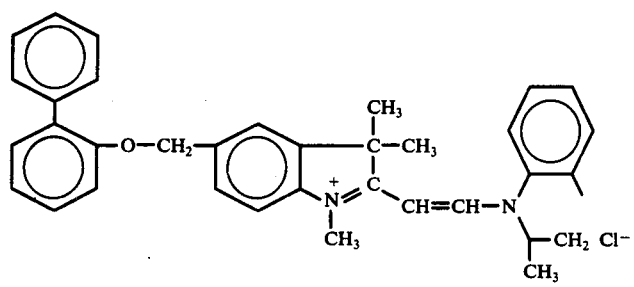

Table XIV-continued

| | | |
|---|---|---|
| 540 | [structure] | |
| 541 | [structure] | yellow |
| 542 | [structure] | greenish-yellow |
| 543 | [structure] | " |

EXAMPLE 544

57.2 parts of the monochloromethylated reaction product of 1-p-diphenoxyethylamino-4-para-toluidinoanthraquinone, obtained by reaction of the latter with dichlorodimethyl ether, are dissolved in 750 parts of methanol at 60° and a solution consisting of 9.4 parts of diethyl amine in 40 parts of methanol is added dropwise at the same temperature. The mixture is heated to the boil, then cooled to 50° and 14 parts of dimethyl sulphate are subsequently added dropwise. The mixture is heated to the boil and then cooled. The precipitated dye is filtered and washed with 50 parts of methanol. After drying, 58.7 parts of the dye of the formula

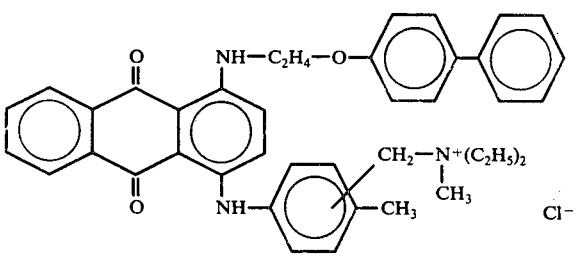

are obtained. Applied on polyacrylonitrile fibres and polyester or polyamide fibres, modified by the introduction of acid groups, this dye gives bright greenish blue dyeings. Using chloromethylated 1-orthodiphenoxymethyl-amino-4-para-toluidinoanthraquinone as starting material, a dye of the formula

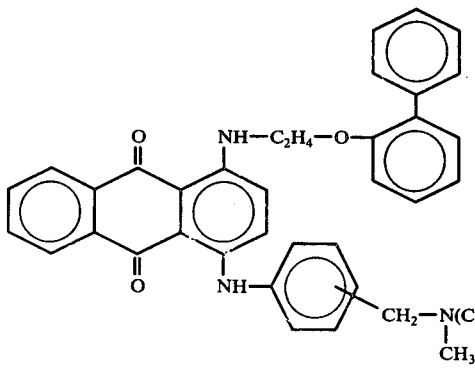

is obtained in accordance with the same process, which dye gives bright greenish-blue dyeings on polyacrylonitrile and acid-modified polyester and polyamide fibres.

The structural composition of further dyes which can be prepared in accordance with the procedure of Example 544 is shown in the following Table XV; they correspond to the formula

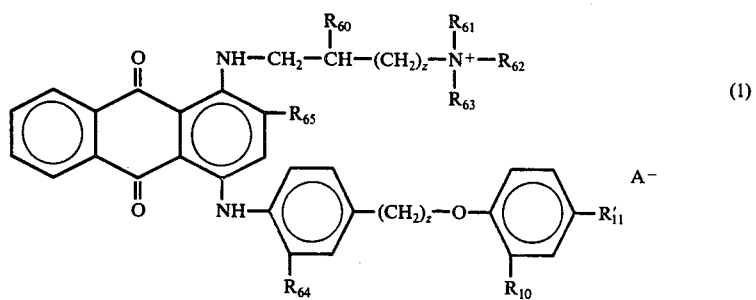

(1)

in which $R_{60}$ to $R_{65}$, $R_{10}$, $R_{11}'$ and Z have the significances as shown in the columns. A further column I indicates the dye shade on polyacrylonitrile. The anion $A^-$ can be any of those named in the foregoing description.

Table XV

| Ex. | $R_{60}$ | $R_{61}$ | $R_{62}$ | z | $R_{63}$ | $R_{64}$ | $R_{65}$ | $R_{10}$ | $R'_{11}$ | I |
|---|---|---|---|---|---|---|---|---|---|---|
| 545 | H | —CH₃ | —CH₃ | 1 | —CH₃ | H | H | H | —C₆H₅ | greenish-blue |
| 546 | H | " | " | 1 | " | H | H | —C₆H₅ | H | " |
| 547 | H | " | " | 1 | H | H | H | " | H | " |
| 548 | H | " | " | 1 | H | H | H | —C₆H₅ | H | " |
| 549 | H | —C₂H₅ | —C₂H₅ | 1 | —CH₃ | H | H | H | " | " |
| 550 | H | " | " | 1 | " | H | H | —C₆H₅ | H | " |
| 551 | —OH | —CH₃ | —CH₃ | 1 | " | H | H | H | " | " |
| 552 | " | " | " | 1 | " | H | H | —C₆H₅ | H | " |
| 553 | H | " | " | 1 | —NH₂ | H | H | H | " | " |
| 554 | H | " | " | 1 | " | H | H | —C₆H₅ | H | " |
| 555 | H | " | " | 1 | " | H | H | H | " | " |
| 556 | H | " | " | 1 | " | H | H | —C₆H₅ | H | " |
| 557 | H | " | " | 1 | —CH₃ | —CH₃ | Br | H | " | " |
| 558 | H | " | " | 1 | " | " | " | —C₆H₅ | H | " |
| 559 | H | " | " | 2 | " | H | H | —C₆H₅ | H | " |
| 560 | H | " | " | 1 | " | H | —CN | H | " | " |
| 561 | H | " | " | 1 | " | H | " | —C₆H₅ | H | " |
| 562 | H | " | " | 1 | " | H | H | H | " | " |

| Ex. | | Dye-shade on polyacrylonitrile |
|---|---|---|
| 563 | | blue |

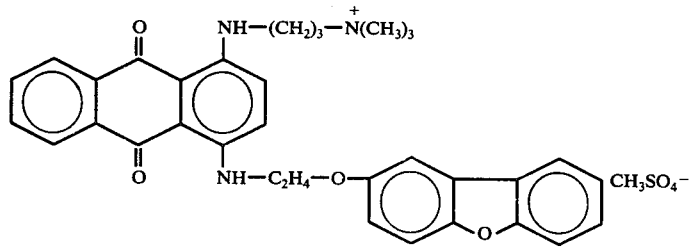

| 564 | | " |

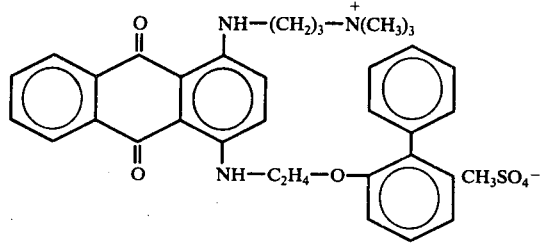

Table XV-continued

565 [anthraquinone structure with NH₂, CONH—(CH₂)₂—O—dibenzofuran, NH—(CH₂)₃—$\overset{+}{N}(CH_3)_3$, $CH_3SO_4^-$] — greenish-blue 566 [anthraquinone structure with NH₂, CONH—C₂H₄—O—biphenyl, NH—(CH₂)₃—$\overset{+}{N}(CH_3)_3$, $CH_3SO_4^-$] — "

567 [anthraquinone structure with NH₂, CONH—(CH₂)₃—$\overset{+}{N}(CH_3)_3$ $CH_3SO_4^-$, NH—C₂H₄—O—dibenzofuran] — "

568 [anthraquinone structure with NH₂, CONH—(CH₂)₃—$\overset{+}{N}(CH_3)_3$ $CH_3SO_4^-$, NH—C₂H₄—O—biphenyl] — "

The structural composition of further dyes is shown in the following Table XVI. They can be prepared in accordance with the procedure of Example 544 and correspond to the formula in which $R_{10}$, $R_{11}'$, $R_{61}$ to $R_{65}$ and Z have the signficances as shown in the column. A further column I indicates the dye shade on polyacrylonitrile. The anion $A^-$ may be any one of those named in the foregoing description.

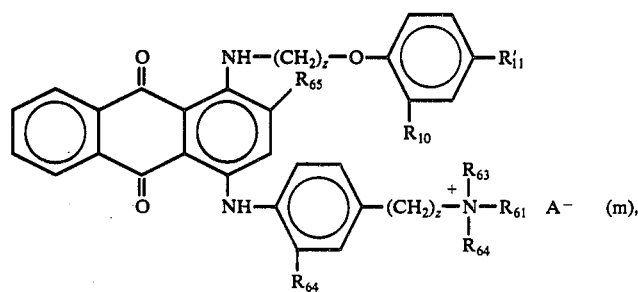

Table XVI

| Ex. | $R_{64}$ | $R_{65}$ | $R_{61}$ | $R_{62}$ | z | $R_{63}$ | $R_{10}$ | $R_{11}'$ | I |
|---|---|---|---|---|---|---|---|---|---|
| 569 | H | H | —CH₃ | —CH₃ | 1 | —CH₃ | H | —C₆H₅ | reddish-blue |
| 570 | H | H | " | " | 1 | " | —C₆H₅ | H | " |
| 571 | H | H | —C₂H₅ | —C₂H₅ | 1 | " | " | H | " |
| 572 | H | H | " | " | 1 | " | H | —C₆H₅ | " |

Table XVI-continued
| | | | | | | | | | |
|---|---|---|---|---|---|---|---|---|---|
| 573 | H | H | " | " | 1 | H | H | " | " |
| 574 | H | H | " | " | 1 | H | ⌬ | H | " |
| 575 | H | H | " | " | 2 | H | " | H | " |
| 576 | H | H | " | " | 2 | H | ⌬ | H | " |
| 577 | H | H | " | " | 1 | —NH₂ | H | " | " |
| 578 | H | H | " | " | 1 | " | ⌬ | H | " |
| 579 | —CH₃ | H | " | " | 1 | —CH₃ | " | H | greenish-blue |
| 580 | " | H | " | " | 1 | " | ⌬ | H | " |
| 581 | H | —CH₃ | " | " | 1 | " | H | " | reddish-blue |
| 582 | H | " | " | " | 1 | " | ⌬ | H | " |
| 583 | H | —Br | " | " | 1 | " | " | H | " |
| 584 | H | " | " | " | 1 | " | ⌬ | H | " |
| 585 | H | —CN | " | " | 1 | " | H | " | greenish-blue |
| 586 | H | " | " | " | 1 | " | ⌬ | H | " |
| Ex. | | Dye-shade on poly acrylonitrile |
|---|---|---|
| 587 | 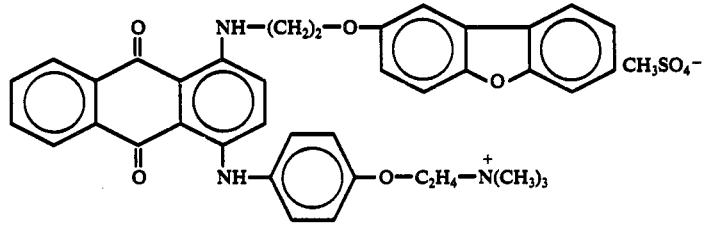 | greenish-blue |
| 588 | 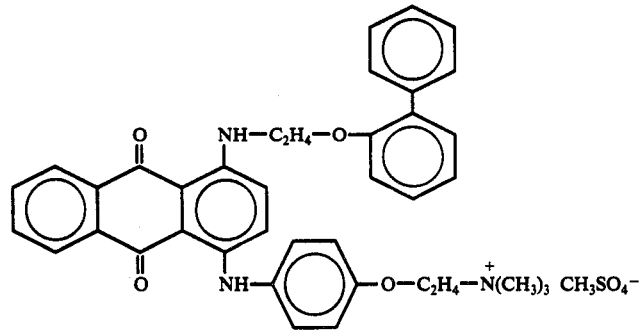 | " |
| 589 | 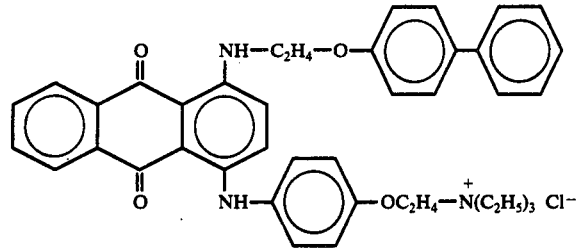 | " |

Table XVI-continued
| 590 | 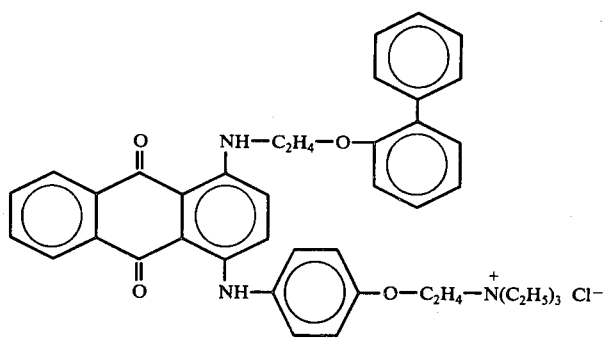 | " |
| 591 | 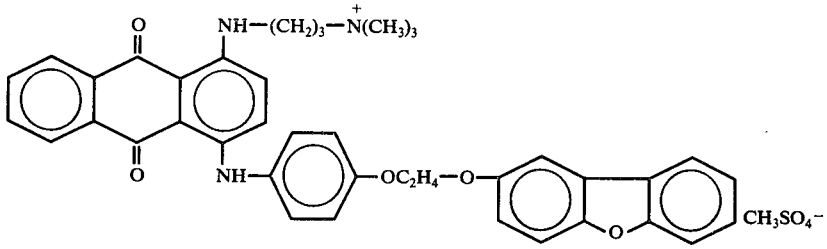 | " |
| 592 | 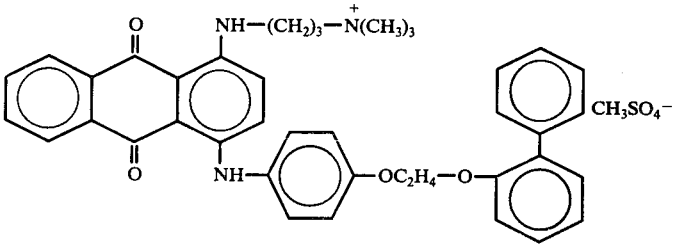 | " |
| 593 | 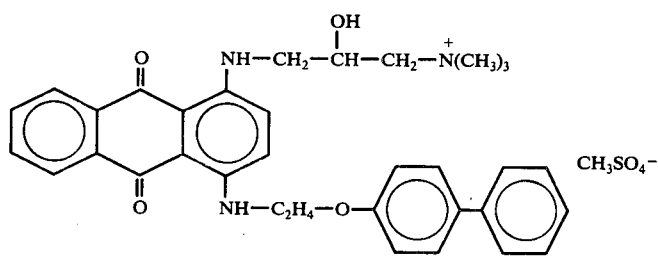 | " |
| 594 | 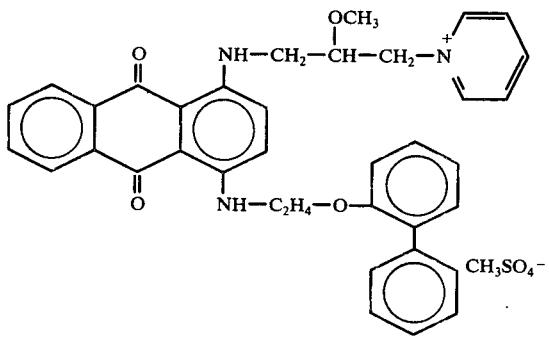 | " |
| 595 | 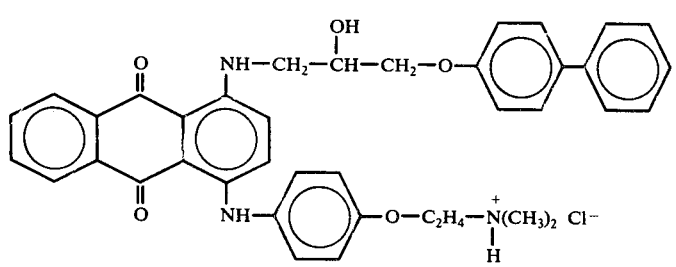 | " |

Table XVI-continued

596 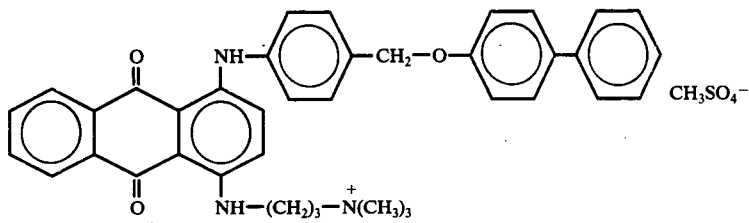 "

Application Example A

20 Parts of the salt of the dye described in Example 1 and 80 parts dextrin are ground for 4 hours in a powder mill. 1 Part of the preparation so obtained is made into a paste with 1 part 40% acetic acid, then 200 parts demineralized water are poured onto the paste and the mixture is boiled for a short time. (The same dye and dextrin mixture can also be formed into a paste with 100 parts water and finally be spray dried). The mixture is then diluted with 7000 parts demineralized water, mixed with 2 parts glacial acetic acid and is put into a bath at 60° with 100 parts polyacrylonitrile fabric. The fabric may be pre-treated for 10 to 15 minutes at 60° in a bath consisting of 8000 parts water and 2 parts glacial acetic acid.

The dyebath is raised to 98° to 100° over a period of 30 minutes, boiled for 1 ½ hours and the fabric is rinsed. A bluish-red dyeing with good light and wet fastness properties is obtained.

10 Parts of the dye mentioned in Example 1 are dissolved in 60 parts glacial acetic acid and 30 parts water. A stable concentrated solution, with a dye content of about 10%, is obtained, which solution can be used to dye polyacrylonitrile according to the above-mentioned process.

Application Example B

20 Parts of the dye from Example 1 are mixed with 80 parts dextrin in a ball-mill for 48 hours; 1 part of the preparation so obtained is made into a paste with 1 part 40% acetic acid, 200 parts demineralized water are poured onto the paste and the mixture is boiled for a short time. With this solution the following dyeings are made:

a. The solution is diluted with 7000 parts of demineralized water and mixed with 21 parts of anhydrous sodium sulphate, 14 parts of ammonium sulphate, 14 parts of formic acid and 15 parts of a carrier, based on the reaction product of ethylene oxide with dichlorophenolene are put into a bath at 60° with 100 parts of a polyester fabric, which fabric has been modified with acid groups. The fabric may be pretreated for 10 to 15 minutes at 60° in a bath consisting of 8000 parts of water and 2 parts of glacial acetic acid.

The dyebath is raised to 98°–100° over a period of 30 minutes, boiled for 1½ hours and the fabric rinsed. A similar bluish-red dyeing with good wet fastness is obtained.

b. The solution is diluted with 3000 parts of demineralized water and mixed with 18 parts of anhydrous sodium sulphate, together with 6 parts of ammonium sulphate and formic acid and put into the bath at 60° with 100 parts of a polyester fabric, which fabric has been modified with acid groups. The closed vessel is heated to 110° over a period of 45 minutes, kept at this temperature for one hour with shaking, cooled to 60° within 25 minutes and the dyed fabric rinsed. A similar bluish-red dyeing with good wet fastness is obtained.

c. The same procedure as described in paragraph b) above is carried out except that the closed vessel is heated for one hour at 120°.

Formulae of representative dyes of the foregoing Examples are as follows:

EXAMPLE 1

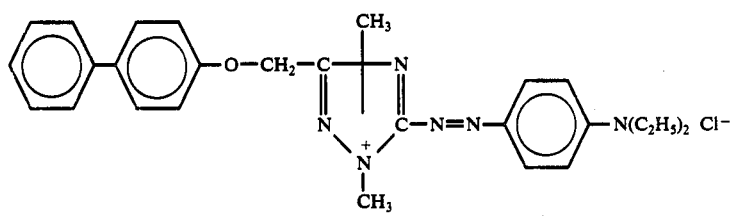

and

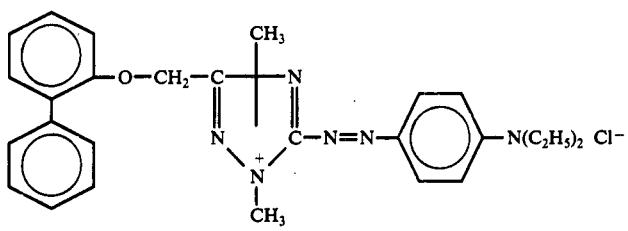

EXAMPLE 2a
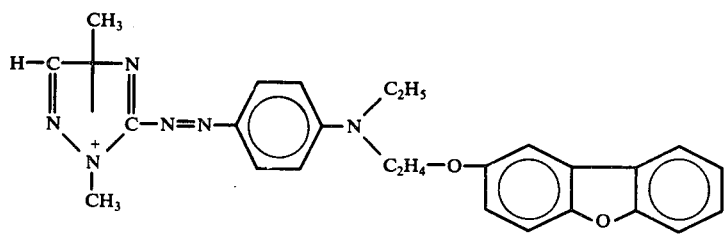
EXAMPLE 133
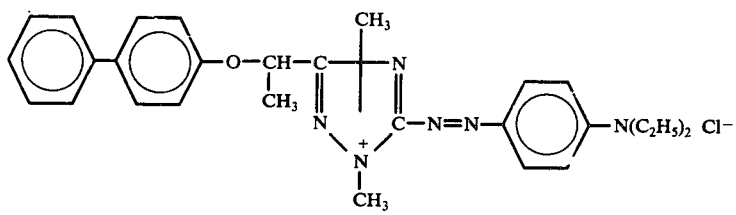
EXAMPLE 151
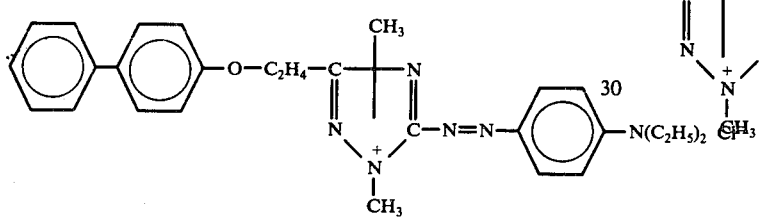
EXAMPLE 249
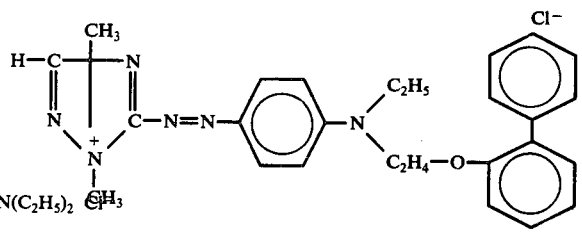
EXAMPLE 250
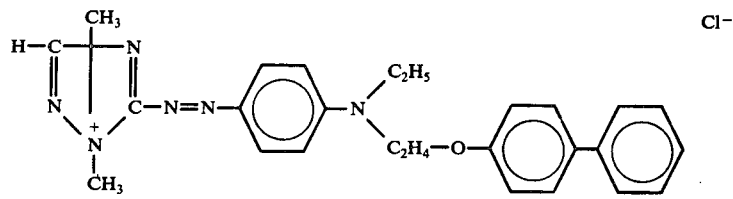
EXAMPLE 152
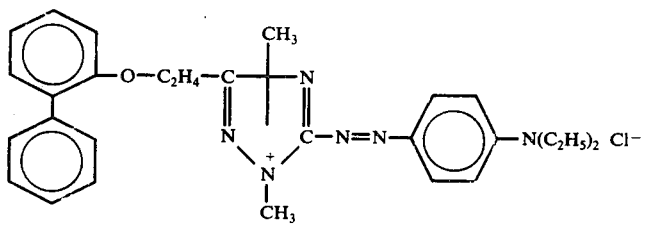
EXAMPLE 332
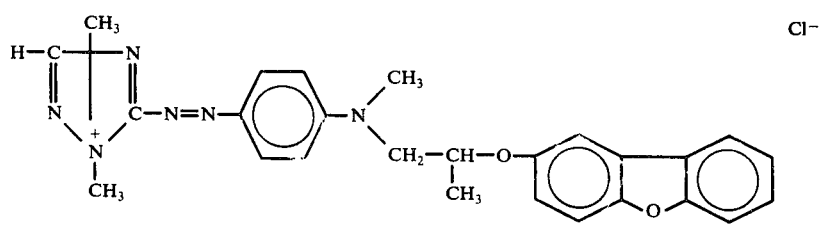

EXAMPLE 389
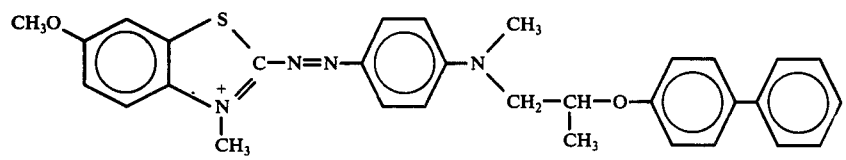
EXAMPLE 465
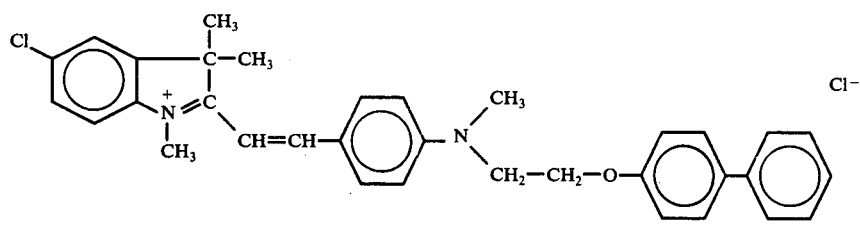
EXAMPLE 447
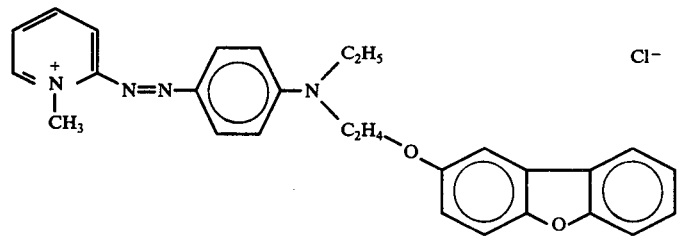
EXAMPLE 490
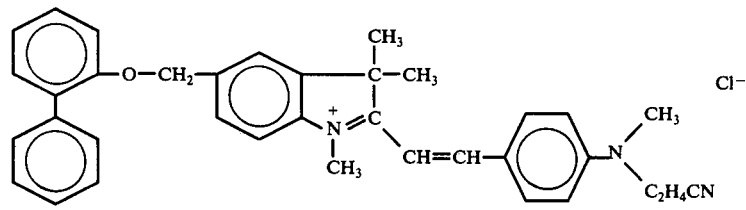
EXAMPLE 451
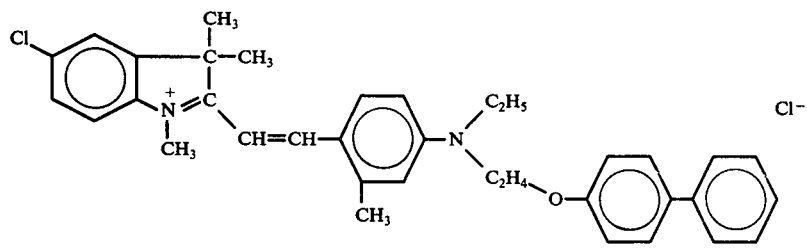
EXAMPLE 492
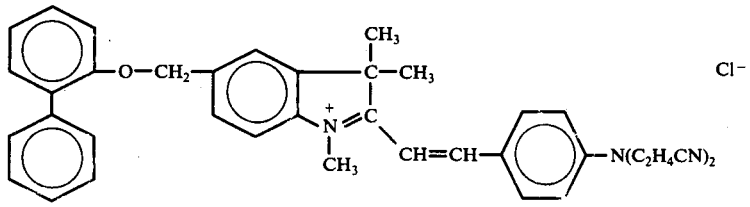

EXAMPLE 495
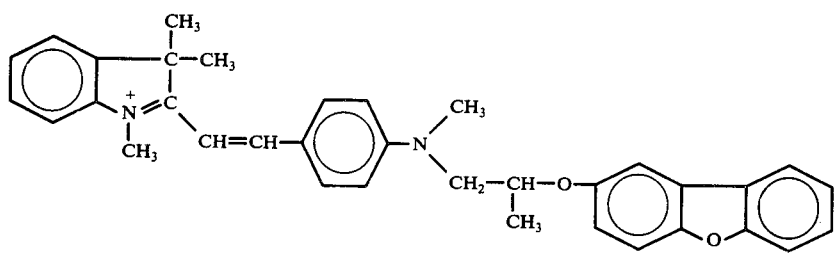
EXAMPLE 496
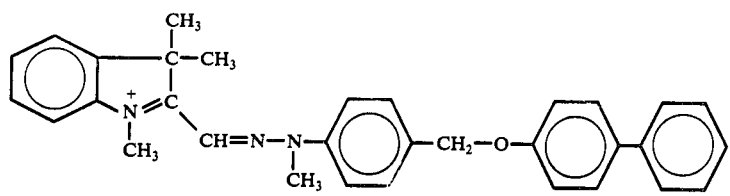
EXAMPLE 496
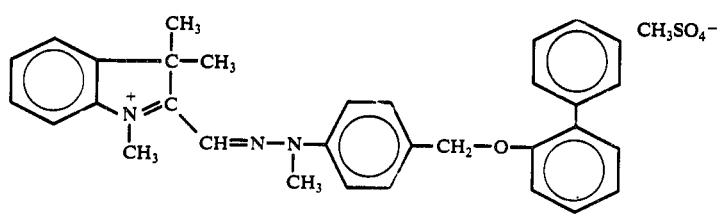
EXAMPLE 498
Cl⁻
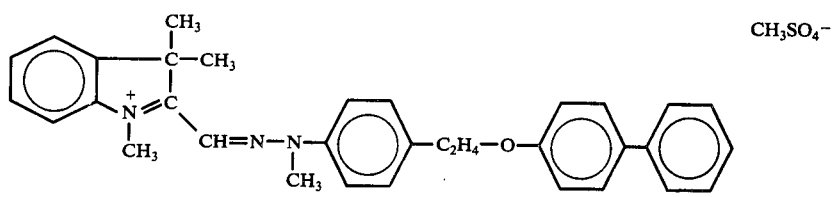
EXAMPLE 516
CH₃SO₄⁻
EXAMPLE 518
CH₃SO₄⁻
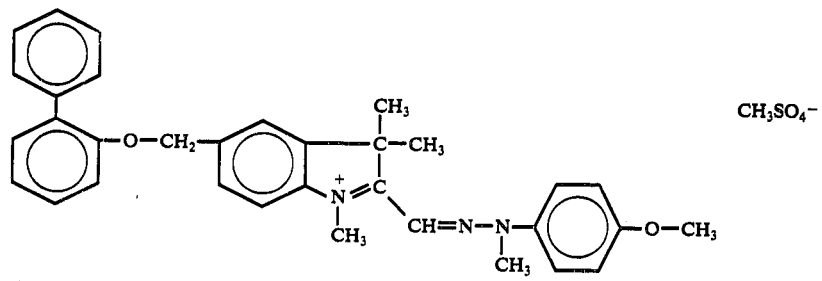
CH₃SO₄⁻
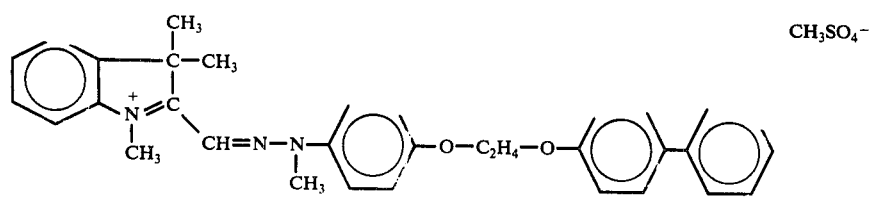

EXAMPLE 521
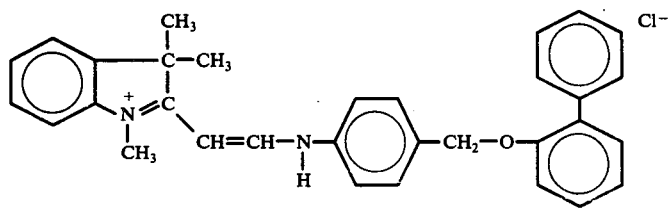
EXAMPLE 524
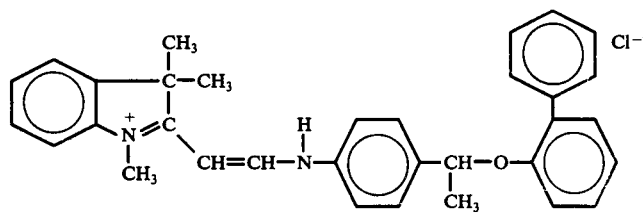
EXAMPLE 539
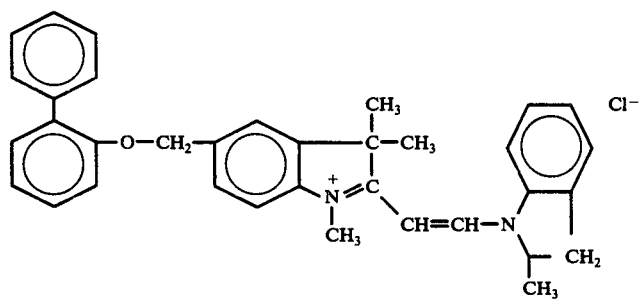
EXAMPLE 540
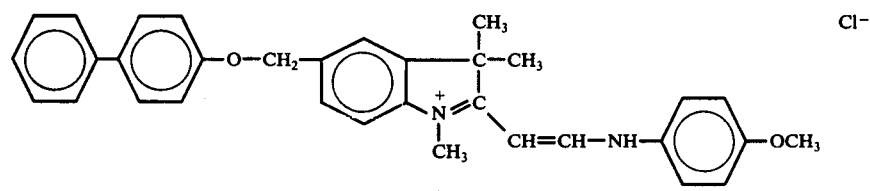
EXAMPLE 541
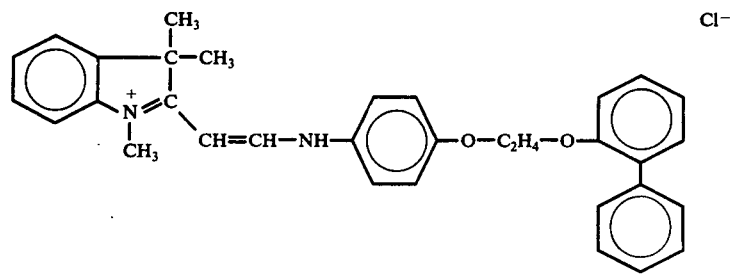

EXAMPLE 543
EXAMPLE 568
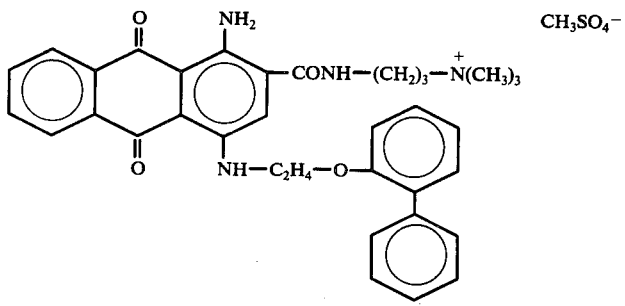
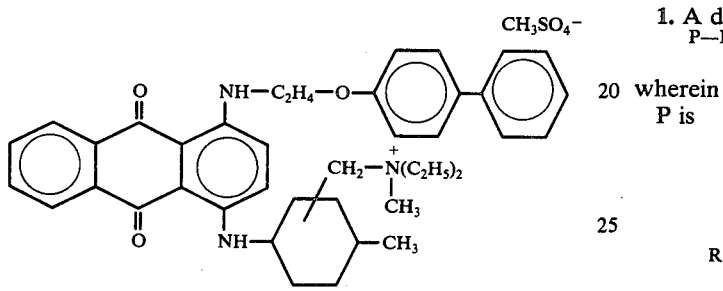
EXAMPLE 546
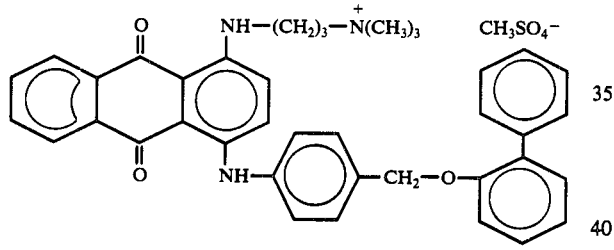
EXAMPLE 552
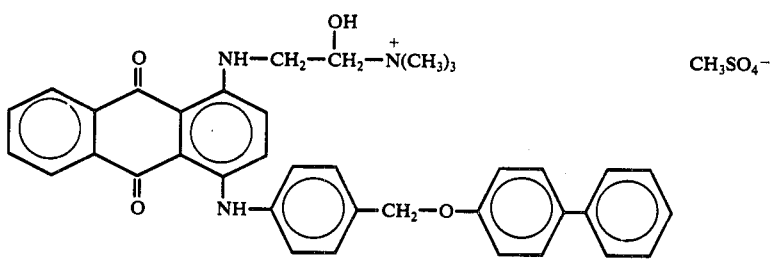
EXAMPLE 563
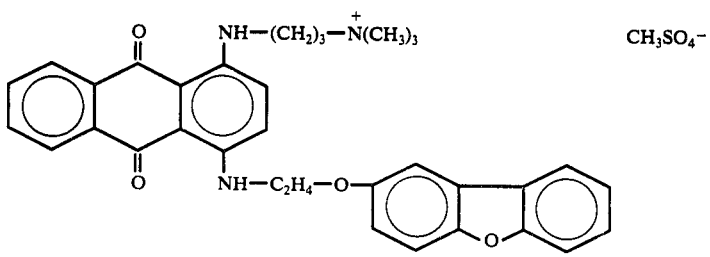
What is claimed is:
1. A dye of the formula
$$P-N=N-K'\quad A^-,$$
wherein
P is
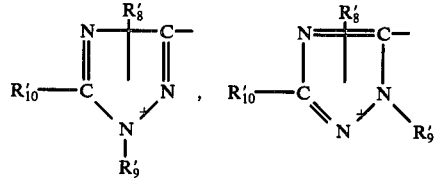
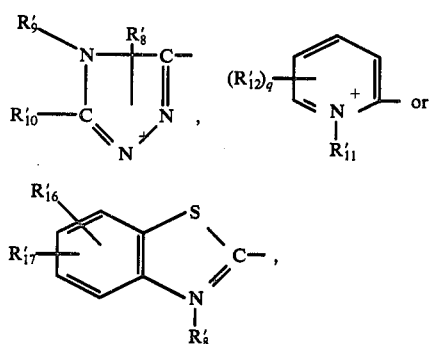
wherein R'₈ is alkyl of 1 to 4 carbon atoms; alkyl of 1 to 4 carbon atoms substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; cyclohexyl; cyclohexyl substituted by alkyl of 1 to 4 carbon atoms; or

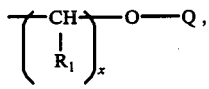

R'₉ is alkyl of 1 to 4 carbon atoms; alkyl of 1 to 4 carbon atoms substituted by hydroxy, halo, cyano, phenyl or carbamoyl; cyclohexyl; cyclohexyl substituted by alkyl of 1 to 4 carbon atoms; phenyl; phenyl substituted by halo, alkyl of 1 to 4 carbon atoms or alkoxy of 1 to 4 carbon atoms; or

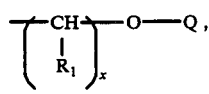

R'₁₀ is hydrogen or R'₉,
R'₁₁ is alkoxy of 1 to 4 carbon atoms; alkoxy of 1 to 4 carbon atoms substituted by hydroxy, halo, cyano, phenyl or carbamoyl; alkyl of 1 to 4 carbon atoms; alkyl of 1 to 4 carbon atoms substituted by hydroxy, halo, cyano, phenyl or carbamoyl; alkenyl of 2 to 4 carbon atoms; alkenyl of 2 to 4 carbon atoms substituted by hydroxy, halo, cyano, phenyl or carbamoyl; or

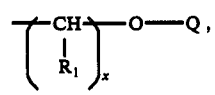

each
R'₁₂ is independently phenyl, halo, nitro, cyano, alkyl of 1 to 4 carbon atoms, alkoxy of 1 to 4 carbon atoms or

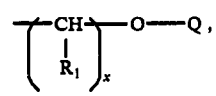

each of
R'₁₆ and R'₁₇ is independently hydrogen; halo; alkyl of 1 to 4 carbon atoms; alkyl of 1 to 4 carbon atoms substituted by phenyl, hydroxy, carbamoyl, cycloalkyl of 5 or 6 carbon atoms, cyano or halo; alkoxy of 1 to 4 carbon atoms; alkoxy of 1 to 4 carbon atoms substituted by phenyl, hydroxy, carbamoyl, cycloalkyl of 5 or 6 carbon atoms, cyano or halo; phenoxy; —CO—Ro; —CO—O—Ro; —CO—NH—Ro; —CO—N(Ro)₂; —NH—CO—Ro; —SO₂—Ro; —SO₂—NH—Ro; —SO₂—N(Ro)₂; —NH—SO₂—Ro or

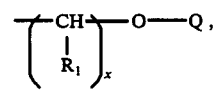

wherein each
Ro is independently alkyl of 1 to 4 carbon atoms or phenyl, or
R'₁₆ and R' are on adjacent carbon atoms and taken together are —CH=CH—CH=CH—, and
q is 0, 1 or 2,

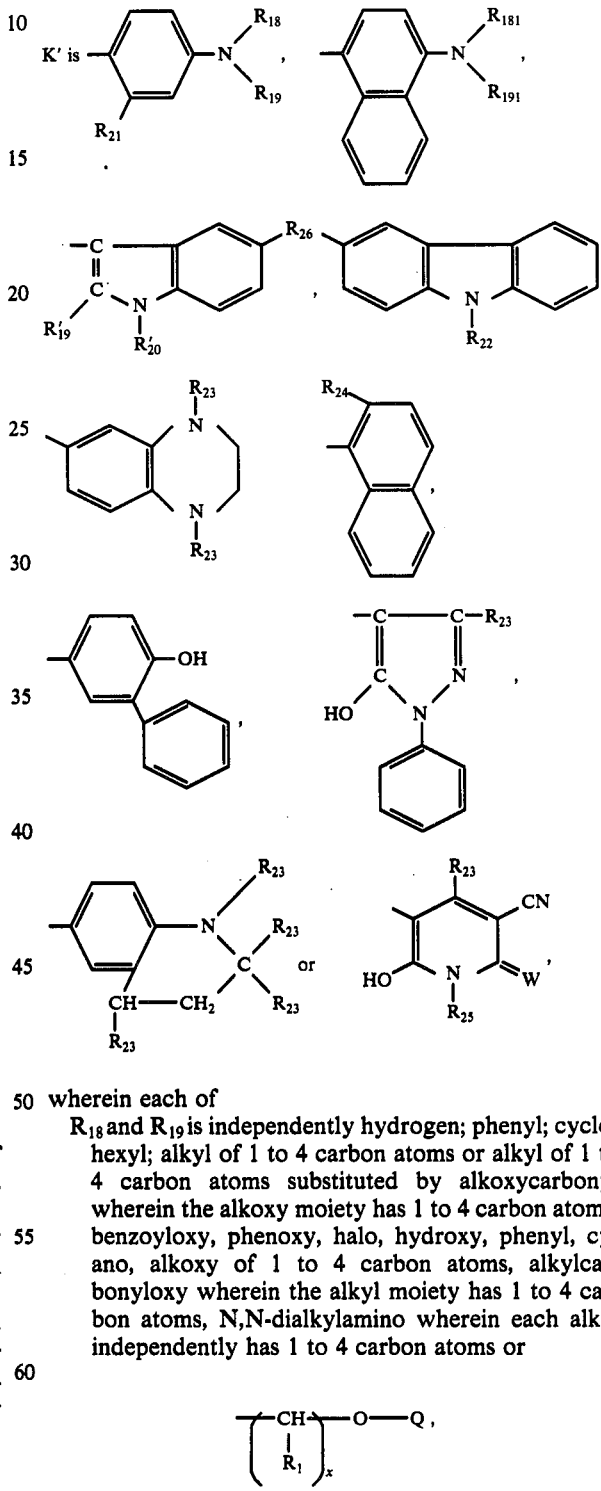

wherein each of
R₁₈ and R₁₉ is independently hydrogen; phenyl; cyclohexyl; alkyl of 1 to 4 carbon atoms or alkyl of 1 to 4 carbon atoms substituted by alkoxycarbonyl wherein the alkoxy moiety has 1 to 4 carbon atoms, benzoyloxy, phenoxy, halo, hydroxy, phenyl, cyano, alkoxy of 1 to 4 carbon atoms, alkylcarbonyloxy wherein the alkyl moiety has 1 to 4 carbon atoms, N,N-dialkylamino wherein each alkyl independently has 1 to 4 carbon atoms or with the proviso that when one of R₁₈ and R₁₉ is phenyl or cyclohexyl, the other is other than phenyl or cyclohexyl, or $R_{18}$ and $R_{19}$ taken together and with the nitrogen atom to which they are joined are

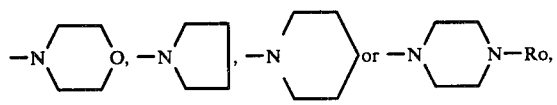

wherein
Ro is alkyl of 1 to 4 carbon atoms or phenyl,
$R'_{19}$ is phenyl, alkyl of 1 to 4 carbon atoms or alkyl of 1 to 4 carbon atoms substituted by phenyl,
$R'_{20}$ is hydrogen, phenyl or alkyl of 1 to 4 carbon atoms,
$R_{21}$ is hyrogen, alkyl of 1 to 4 carbon atoms, alkoxy of 1 to 4 carbon atoms or halo,
$R_{22}$ is alkyl of 1 to 4 carbon atoms,
each
$R_{23}$ is independently alkyl of 1 to 4 carbon atoms,
$R_{24}$ is hydroxy, amino or anilino,
$R_{25}$ is hydrogen, alkyl of 1 to 4 carbon atoms or alkyl of 1 to 4 carbon atoms substituted by alkoxy of 1 to 4 carbon atoms,
$R_{26}$ is hydrogen, halo, alkyl of 1 to 4 carbon atoms or alkoxy of 1 to 4 carbon atoms,
each of
$R_{181}$ and $R_{191}$ is independently hydrogen; phenyl; cyclohexyl; alkyl of 1 to 4 carbon atoms or alkyl of 1 to 4carbon atoms substituted by alkoxycarbonyl wherein the alkoxy moiety has 1 to 4 carbon atoms, benzoyloxy, phenoxy, halo, hydroxy, phenyl, cyano, alkoxy of 1 to 4 carbon atoms, alkylcarboxyloxy wherein the alkyl moiety has 1 to 4 carbon atoms, N,N-dialkylamino wherein each alkyl independently has 1 to 4 carbon atoms or

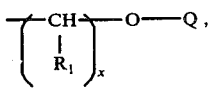

with the proviso that at least one of $R_{181}$ and $R_{191}$ is hydrogen or alkyl of 1 to 4 carbon atoms, and
W is =O or =NH, and
$A^-$ is an anion, with the proviso that each molecule contains 1 to 3 groups of the formula

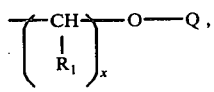

each of which is independently a significance of $R'_8$, $R'_9$, $R'_{10}$, $R'_{11}$, $R'_{12}$, $R'_{16}$ or $R'_{17}$ or is attached to $R_{18}$, $R_{19}$, $R_{181}$ or $R_{191}$,
wherein each
Q is biphenylyl, dibenzofuranyl, carbazolyl, dibenzothienyl, dibenzothiophendioxydyl, dibenzothiophenmonoxydyl, fluorenyl or fluorenonyl, or a substituted derivative thereof having 1 or 2 substituents, wherein each substituent is independently hydroxy; halo; alkyl of 1 to 4 carbon atoms; alkyl of 1 to 4 carbon atoms substituted by halo, hydroxy, cyano, phenyl or phenoxy; alkoxy of 1 to 4 carbon atoms; alkoxy of 1 to 4 carbon atoms substituted by halo, hydroxy, cyano, phenyl or phenoxy; cycloalkyl of 5 or 6 carbon atoms; cycloalkyl of 5 or 6 carbon atoms substituted by alkyl of 1 to 4 carbon atoms; trifluoromethyl; cyano; nitro; phenoxy; phenylazo; —CO—Ro; —CO—O—Ro; —O—CO—Ro; —CO—NH—Ro; —CO—N(Ro)$_2$; —NH—CO—Ro; —SO$_2$—Ro, —SO$_2$—NH—Ro, —SO$_2$—N(Ro)$_2$; —O—SO$_2$—N(Ro)$_2$;

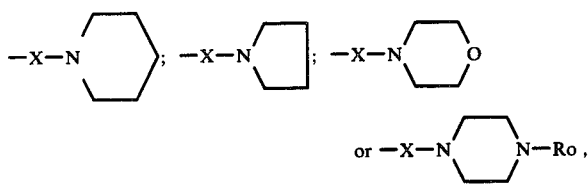

wherein each
Ro is independently alkyl of 1 to 4 carbon atoms or phenyl, and
each
X is —CO— or —SO$_2$—,
each
$R_1$ is independently hydrogen, phenyl, cycloalkyl of 5 to 6 carbon atoms, alkyl of 1 to 4 carbon atoms or alkyl of 1 to 4 carbon atoms substituted by halo, alkoxy of 1 to 4 carbon atoms or phenoxy, and each
$x$ is 1, 2 or 3,
wherein each halo is independently chloro, bromo or iodo.

2. A dye according to claim 1 wherein each $x$ is 1 or 2.

3. A dye according to claim 2 wherein K' is

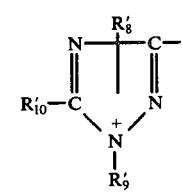

4. A dye according to claim 1 wherein P is

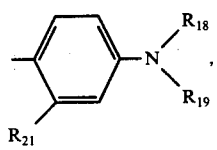

5. A dye according to claim 4 wherein K' is

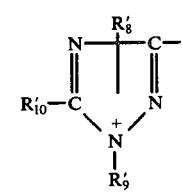

each
$R_1$ is hydrogen or alkyl of 1 to 4 carbon atoms,
each
$x$ is 1 or 2, and
each
Q is biphenylyl or dibenzofuranyl.

6. A dye according to claim 1 wherein each

R₁ is hydrogen, alkyl of 1 to 4 carbon atoms or phenyl.

7. A dye according to claim 6 wherein each

R₁ is hydrogen or methyl.

8. A dye according to claim 6 wherin each

R₁ is hydrogen or alkyl of 1 to 4 carbon atoms, each x is 1 or 2, and each

Q is biphenylyl or dibenzofuranyl.

9. A dye according to claim 8 wherein each

R₁ is hydrogen or methyl.

10. A dye according to claim 6 having the formula

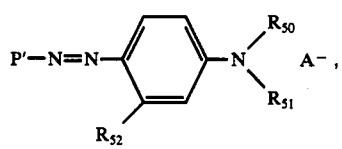

wherein P' is

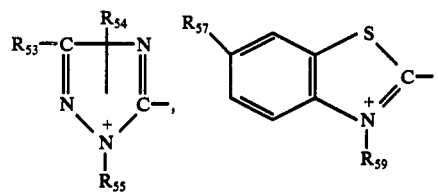

or

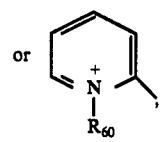

wherein

R₅₃ is hydrogen, methyl, phenyl benzyl or

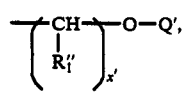

each of

R₅₄ and R₅₅ is independently alkyl of 1 to 4 carbon atoms or alkyl of 1 to 4 carbon atoms substituted by hydroxy or carbamoyl, R₅₇ is hydrogen or alkoxy of 1 to 4 carbon atoms, R₅₉ is alkyl of 1 to 4 carbon atoms or alkyl of 1 to 4 carbon atoms substituted by carbamoyl, and R₆₀ is alkyl of 1 to 4 carbon atoms or alkoxy of 1 to 4 carbon atoms, R₅₀ is alkyl of 1 to 4 carbon atoms or alkyl of 1 to 4 carbon atoms substituted by phenyl, R₅₁ is alkyl of 1 to 4 carbon atoms or

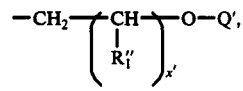

R₅₂ is hydrogen or methyl, and

A⁻ is an anion, wherein

R₁" is hydrogen or methyl, x' is 1 or 2, and

Q' is o-biphenylyl, p-biphenylyl or 3-dibenzofuranyl, with the proviso that the molecule contains

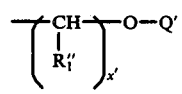

11. A dye according to claim 10 having the formula

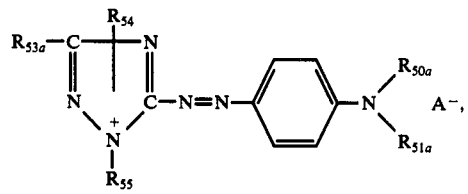

wherein

R₅₀ₐ is alkyl of 1 to 4 carbon atoms,

R₅₁ₐ is alkyl of 1 to 4 carbon atoms or

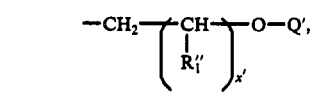

R₅₃ₐ is hydrogen or

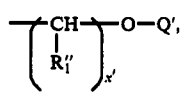

each of

R₅₄ and R₅₅ is independently alkyl of 1 to 4 carbon atoms or alkyl of 1 to 4 carbon atoms substituted by hydroxy or carbamoyl, and A⁻ is an anion, wherein R₁" is hydrogen or methyl, x' is 1 or 2, and Q' is o-biphenylyl, p-biphenylyl or 3-dibenzofuranyl, with the proviso that the molecule contains one

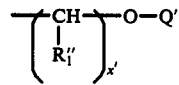

group.

12. A dye according to claim 11 wherein R₅₃ₐ is hydrogen.

13. A dye according to claim 11 having the formula

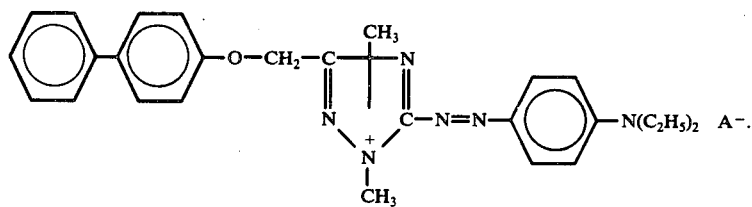
14. A dye according to claim 11 having the formula
15. A dye according to of claim 11 having the formula
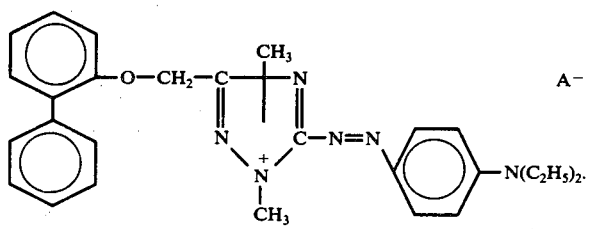
16. A dye according to claim 11 having the formula
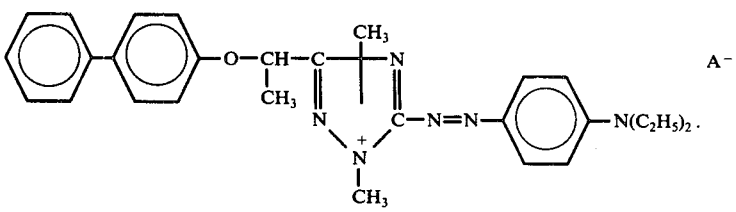
17. A dye according to of claim 11 having the formula
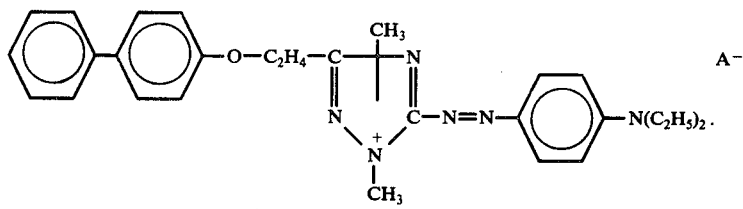
18. A dye according to of claim 11 having the formula
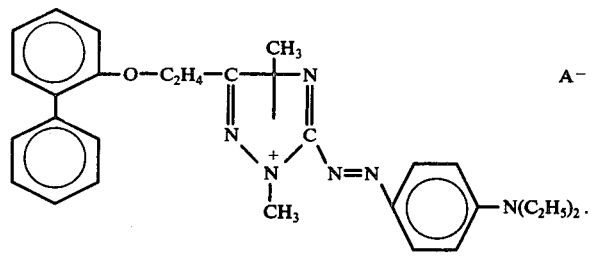
19. A dye according to claim 11 having the formula
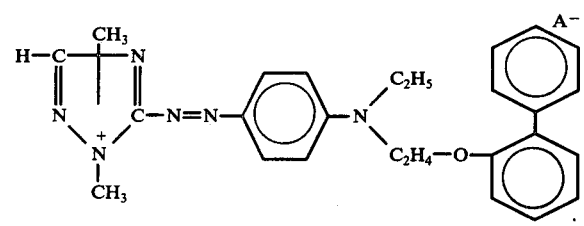
20. A dye according to claim 11 having the formula
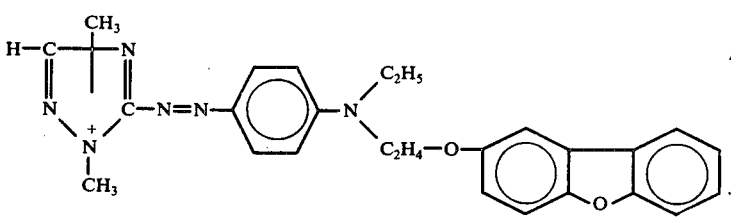

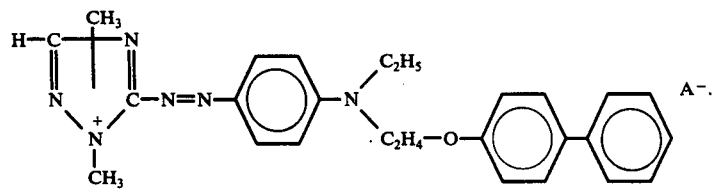
21. A dye according to claim 11 having the formula
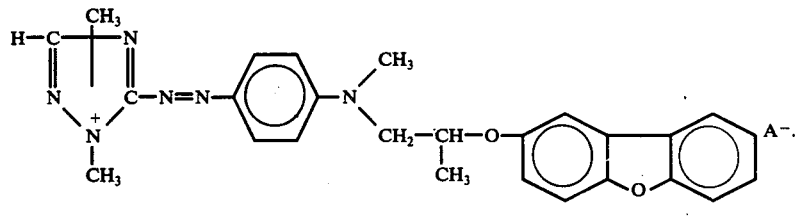
22. A dye according to claim 10 having the formula
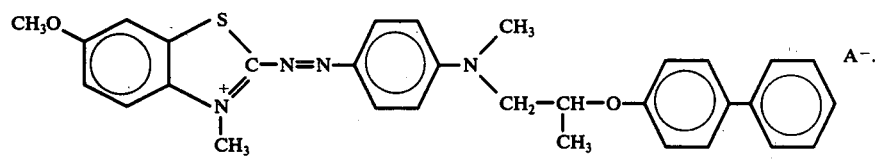
23. A dye according to claim 10 having the formula
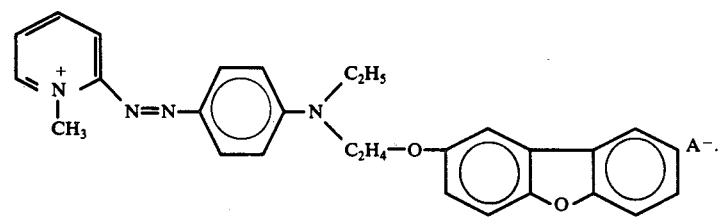
* * * * *